(12) United States Patent
Kratz et al.

(10) Patent No.: US 11,377,473 B2
(45) Date of Patent: Jul. 5, 2022

(54) ALBUMIN-BINDING PRODRUGS OF AURISTATIN E DERIVATIVES

(71) Applicant: CENTURION BIOPHARMA CORPORATION, Los Angeles, CA (US)

(72) Inventors: Felix Kratz, Ehrenkirchen (DE); Khalid Abu Ajaj, Berlin (DE); Anna Warnecke, Freiburg (DE); Friederike I. Nollmann, Freiburg (DE); Stephan David Koester, Gundelfingen (DE); Javier Garcia Fernandez, Freiburg (DE); Lara Pes, Freiburg (DE); Heidi-Kristin Walter, Freiburg (DE); Johannes Pall Magnusson, Freiburg (DE); Serghei Chercheja, Freiburg (DE); Patricia Perez Galan, Freiburg (DE); Federico Medda, Freiburg (DE); Steffen Josef Daum, Emmendingen (DE)

(73) Assignee: CENTURION BIOPHARMA CORPORATION, Los Angeles, CA (US)

( * ) Notice: Subject to any disclaimer, the term of this patent is extended or adjusted under 35 U.S.C. 154(b) by 0 days.

(21) Appl. No.: 16/768,436

(22) PCT Filed: Nov. 30, 2018

(86) PCT No.: PCT/US2018/063376
§ 371 (c)(1),
(2) Date: May 29, 2020

(87) PCT Pub. No.: WO2019/108974
PCT Pub. Date: Jun. 6, 2019

(65) Prior Publication Data
US 2020/0385421 A1 Dec. 10, 2020

Related U.S. Application Data

(60) Provisional application No. 62/592,721, filed on Nov. 30, 2017.

(51) Int. Cl.
*A61K 38/07* (2006.01)
*A61K 47/54* (2017.01)
*A61K 47/64* (2017.01)
*C07K 5/02* (2006.01)
*A61K 47/40* (2006.01)
*A61K 9/00* (2006.01)

(52) U.S. Cl.
CPC .......... *C07K 5/0205* (2013.01); *A61K 38/07* (2013.01); *A61K 47/40* (2013.01); *A61K 47/54* (2017.08); *A61K 47/643* (2017.08); *A61K 9/0019* (2013.01)

(58) Field of Classification Search
CPC ........ A61K 38/07; A61K 47/50; A61K 47/54; A61K 47/643; C07K 5/0205
See application file for complete search history.

(56) References Cited

U.S. PATENT DOCUMENTS

| | | | |
|---|---|---|---|
| 4,125,704 | A | 11/1978 | Henry |
| 4,699,880 | A | 10/1987 | Goldstein |
| 4,816,397 | A | 3/1989 | Boss |
| 4,816,567 | A | 3/1989 | Cabilly |
| 4,946,778 | A | 8/1990 | Ladner |
| 4,966,999 | A | 10/1990 | Coughlin |
| 5,225,539 | A | 7/1993 | Winter |
| 5,476,786 | A | 12/1995 | Huston |
| 5,514,548 | A | 5/1996 | Krebber |
| 6,884,869 | B2 | 4/2005 | Senter |
| 7,387,771 | B1 | 6/2008 | Kratz |
| 8,703,724 | B2 | 4/2014 | Kratz |
| 2012/0195832 | A1 | 8/2012 | Kratz |
| 2014/0221429 | A1 | 8/2014 | Al-Resayes |
| 2020/0385403 | A1 | 12/2020 | Kratz |

FOREIGN PATENT DOCUMENTS

| | | |
|---|---|---|
| EP | 0239400 | 9/1987 |
| EP | 0125023 | 6/1991 |
| EP | 0519596 | 12/1992 |
| EP | 0120694 | 7/1993 |
| EP | 0194276 | 8/1993 |
| EP | 0451216 | 1/1996 |
| EP | 2289558 | 3/2011 |
| WO | WO1986001533 | 3/1986 |
| WO | WO1993006213 | 4/1993 |
| WO | WO2001062726 | 8/2001 |
| WO | WO2002088172 | 11/2002 |
| WO | WO2005055939 | 6/2005 |
| WO | WO2013124068 | 8/2013 |
| WO | WO2016205378 | 12/2016 |
| WO | WO2019108975 | 6/2019 |

OTHER PUBLICATIONS

Berge, et al., "Pharmaceutical Salts", J. Pharm. Sci. 66(1): 1-19 (1977).
Bird, et al., "Single-Chain Antigen-Binding Proteins", Science 242: 423-426 (1988).
Chari, et al., "Antibody-Drug Conjugates: An Emerging Concept in Cancer Therapy", Angewandte Reviews 53: 3796-3827 (2014).
Chen, et al., "Tubulin Inhibitor-Based Antibody-Drug Conjugates for Cancer Therapy," Molecules, 22(8):1281-1309 (2017).
Cross, et al., "Rules for the Nomenclature of Organic Chemistry—Section E: Stereochemistry", Pure and Applied Chemistry 45: 11-30 (1976).
Dao, et al., "Design, synthesis, and initial biological evaluation of a steroidal anti-estrogen-doxorubicin bioconjugate for targeting estrogen receptor-positive breast cancer cells", Bioconjugate Chemistry 23: 785-795 (2012).

(Continued)

*Primary Examiner* — Jeffrey E. Russel
(74) *Attorney, Agent, or Firm* — Haley Guiliano LLP

(57) ABSTRACT

The present disclosure provides for albumin-binding prodrugs of auristatin E derivatives and uses thereof.

55 Claims, 25 Drawing Sheets

(56) References Cited

OTHER PUBLICATIONS

Daugherty, et al., "Polymerase chain reaction facilitates the cloning, CDR-grafting, and rapid expression of a murine monoclonal antibody directed against the CD18 component of leukocyte integrins", Nucleic Acids Research 19(9): 2471-2476 (1991).
Kamman, et al., "Rapid insertional mutagenesis of DNA by polymerase chain reaction (PCR)", Nucleic Acids Research 17(13): 5404 (1989).
Kratz, et al., "Preparation, characterization and in vitro efficacy of albumin conjugates of doxorubicin", Biological & Pharmaceutical Bulletin 21(1): 56-61 (1998).
Kratz, et al., "Prodrug strategies in anticancer chemotherapy", ChemMedChem 3(1): 20-53 (2008).
Kratz, et al., "Transferrin conjugates of doxorubicin: Synthesis, characterization, cellular uptake, and in vitro efficacy", J. Pharm. Sci. 87(3): 338-346 (1998).
Lau, et al., "Novel doxorubincon-monoclonal anti-carcinoembryonic antigen antibody immunoconjugate activity in vitro", Bioorganic & Medicinal Chemistry 3(10): 1305-1312 (1995).
Lewis, et al., "Immunoglobulin complementarity-determining region grafting by recombinant polymerase chain reaction to generate humanized monoclonal antibodies", Gene 101:297-302 (1991).
Newman, et al., ""Primatization" of Recombinant Antibodies for Immunotherapy of Human Diseases: A Macaque/Human Chimeric Antibody Against Human CD4", Biotechnology 10: 1455-1460 (1992).
Nollmann, et al., "Abstract 1657: Structure-activity relationship studies and biological evaluation of novel maytansinoids, a class of highly selective tubulin inhibitors," Cancer Research, 78(13) (2018) (4 pages).
Nollmann, et al., "Abstract 2661: Novel albumin-binding maytansinoids inducing long-term partial and complete tumor regressions in several human cancer xenograft models in nude mice," Cancer Research, 78(13) (2018) (4pages).
Panowski, et al., "Site-specific antibody drug conjugates for cancer therapy", mAbs 6(1):34-45 (2014).
Ponta, et al., "Tumor-preferential sustained drug release enhances antitumor activity of block copolymer micelles", J. Drug Targeting 22(7): 619-628 (2014).
Rea, et al., "Site-specifically radioiodinated antibody for targeting tumors", Cancer Research (Suppl.) 50: 857s-861s (1990).
Rodrigues, et al., "Correlation of the acid-sensitivity of polyethylene glycol daunorubicin conjugates with their invitro antiproliferative activity", Bioorganic & Medicinal Chemistry 14(12): 4110-4117 (2006).
Sato, et al., "Reshaping a Human Antibody to Inhibit the Interleukin 6-dependent Tumor Cell Growth", Cancer Research 53: 851-856 (1993).
Temming, et al., "Evaluation of RGD-targeted albumin earners for specific delivery of auristatin E to tumor blood vessels," Bioconjugate Chemistry, 17(6):1385-1394 (2006).
U.S. Appl. No. 15/735,885, filed Dec. 12, 2017, Felix Kratz, Pending.
U.S. Appl. No. 16/768,418, filed May 29, 2020, Felix Kratz, Pending.
E.A. Perez et al., "Phase II trial of dolastatin-10 in patients with advanced breast cancer," Invest. New Drugs, 23:257-261 (2005).
F. Kratz, "Albumin as a drug carrier: Design of prodrugs, drug conjugates and nanoparticles," J. Control. Release, 132:171-183 (2008).
F. Kratz, U. Beyer, "Serum Proteins as Drug Carriers of Anticancer Agents: A Review," Drug Delivery, 5:281-299 (1998).
M. von Mehren et al., "Phase II trial of dolastatin-10, a novel anti-tubulin agent, in metastatic soft tissue sarcomas," Sarcoma, 8:107-111 (2004).
Pyataev, et al. "Targeted Delivery of Antitumor Chemotherapeutics: Advanced Technologies and Development Prospects," Povolzhskiy Onkologicheskiy Vestnik, 2012, No. 2, pp. 60-71. (English Abstract Only).
R.S. Marks et al., "A Phase II Study of the Dolastatin 15 Analogue LU103793 in the Treatment of Advanced Non-Small-Cell Lung Cancer," Am. J. Clin. Oncol., 26:336-337 (2003).

(a)

(b)

(a)

(b)

(a)

(b)

(a)

(b)

ALBUMIN-BINDING PRODRUGS OF AURISTATIN E DERIVATIVES

This application is a United States National Phase Application filed under 35 U.S.C. § 371 of International Patent Application No. PCT/US2018/063376, filed on Nov. 30, 2018, which claims the benefit of and priority from U.S. Provisional Application 62/592,721 filed Nov. 30, 2017, the disclosures of which are incorporated by reference herein in their entireties.

BACKGROUND

Low-molecular weight anticancer drugs often have a narrow therapeutic window which limits their clinical efficacy. These low-molecular weight compounds show a high tendency to penetrate body tissues by diffusion, resulting in a uniform biodistribution. Therefore, only small quantities of the drug reach the site of action and, due to distribution over healthy tissues of the body, said drugs give rise to problematic side effects.

These disadvantages are particularly critical for those drugs which are highly cytotoxic and have a very narrow therapeutic window. Auristatins are tubulin-binding peptide-based drugs and representative examples such as dolastatin 10, dolastatin 15, auristatin PE, auristatin E or auristatin F exhibit highly cytotoxic effects. In clinical phase 1 and 2 trials dolastatin 10, dolastatin 15, and auristatin PE have resulted in unacceptable systemic toxicity as well as a lack of antitumor activity and were thus discontinued (E. A. Perez et al., Invest. New Drugs, 23:257-261 (2005); M. von Mehren et al., Sarcoma, 8:107-111 (2004); R. S. Marks et al., Am. J. Clin. Oncol., 26:336-337 (2003)).

Drug delivery in oncology is an approach that has the potential of increasing the narrow therapeutic index of highly cytotoxic agents. In most drug delivery systems, the cytotoxic drug is bound to the carrier through a spacer that incorporates a pre-determined breaking point that allows the bound drug to be released at the cellular target site (F. Kratz et al., ChemMedChem, 3:20-53 (2008)).

Albumin or its drug conjugates exhibit a markedly long half-life in the systemic circulation of up to 19 days. An especially attractive approach is to develop prodrugs of highly cytotoxic agents that bind covalently to circulating serum albumin that serves as a macromolecular carrier upon administration. Because of 1.) an elevated permeability of macromolecules through vessel walls of malignant, infected or inflamed tissue combined with an intact lymphatic drainage system and 2.) the expression of albumin-binding proteins on tumor endothelia and within the tumor interstitium, albumin drug conjugates transport the therapeutically effective substance to the target site (i.e. the tumor) where the highly cytotoxic agent is released (U.S. Pat. No. 7,387,771; F. Kratz, J. Control. Release, 132:171-183 (2008); F. Kratz, U. Beyer, Drug Delivery, 5:281-299 (1998)).

However, when designing drug delivery systems with highly cytotoxic agents, a critical balance should be struck between preserving the targeting properties of the drug carrier while enabling a controlled release of the cytotoxic drug and avoiding its premature release in the blood circulation or systemically. Acid-sensitive drug delivery systems should have sufficient stability in the bloodstream, and yet allow effective release of the drug at the tumor site in a pH-dependent manner (F. Kratz et al., ChemMedChem, 3:20-53 (2008)).

For highly cytotoxic drugs with $IC_{50}$ values against tumor cells in the picomolar range, such as the class of low-molecular weight peptide-based auristatins, that cannot be administered due to their water-insolubility and very narrow therapeutic window, there is a need for efficient drug delivery and release systems to achieve more effective and controlled delivery and release of such highly potent drugs. Therefore, the present disclosure provides more efficient and/or more tolerable pharmaceutical compositions of albumin-binding prodrugs of auristatin E derivatives that can be used in the treatment of malignant diseases.

SUMMARY

The present disclosure provides a compound having the structure of Formula I or II:

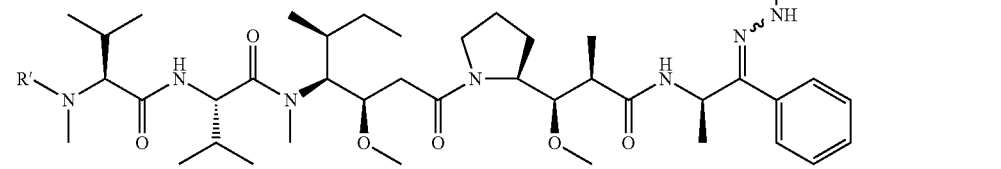

Formula I

-continued

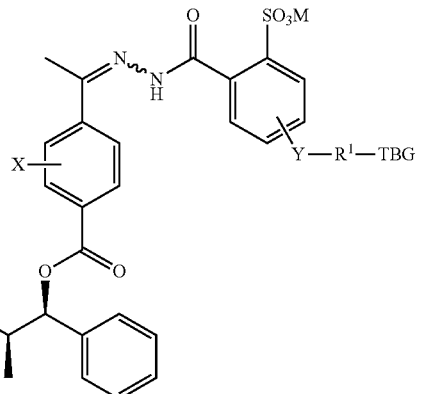
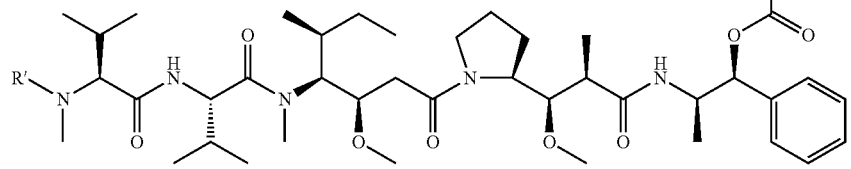

Formula II or a pharmaceutically acceptable salt, hydrate, solvate, or isomer thereof;

wherein:

R' is H or —CH$_3$,

M is H or a pharmaceutically acceptable counterion;

Y is absent or selected from an optionally substituted C$_1$-C$_6$ alkyl, —NH—C(O)—, —C(O)—NH—, —NH—C(O)—NH—, —C(O)—O—, and —O—C(O)—;

R$^1$ is absent or an optionally substituted C$_1$-C$_{18}$ alkyl wherein optionally up to six carbon atoms in said C$_1$-C$_{18}$ alkyl are each independently replaced with —OCH$_2$CH$_2$—;

X is H or selected from halogen (e.g., —F, —Cl, —Br or —I), —NO$_2$, —NR$^2$R$^3$, —OR$^2$, —NHCOR$^2$ and —OCOR$^2$, wherein R$^2$ and R$^3$ are each independently selected from H and C$_1$-C$_4$ alkyl;

TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, and an optionally substituted acetylene group.

In some embodiments, R' is —CH$_3$. In other embodiments, R' is H.

In some embodiments, TBG is selected from an optionally substituted maleimide group.

In some embodiments, TBG is a maleimide group of the formula:

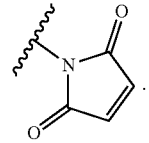 [SMILES: *N1C(=O)C=CC1=O]

In some embodiments, Y is —NH—C(O)—.

In some embodiments, M is H$^+$ or Na$^+$.

In some embodiments, R$^1$ is an optionally substituted C$_1$-C$_5$ alkyl. In other embodiments, R$^1$ is C$_1$-C$_5$ alkyl.

In some embodiments, the disclosure provides a compound having the structure of Formula III:

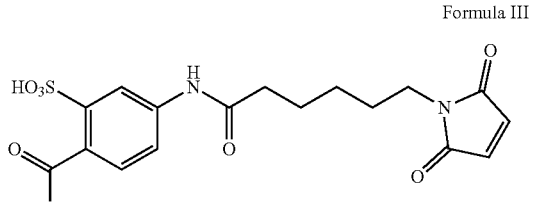
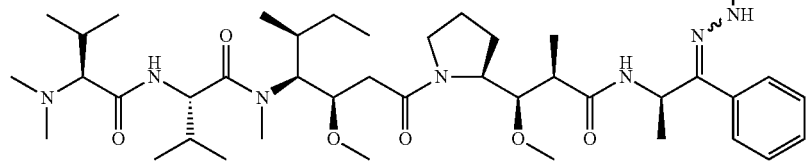

Formula III

In other embodiments, the disclosure provides a compound having the structure of Formula IV:

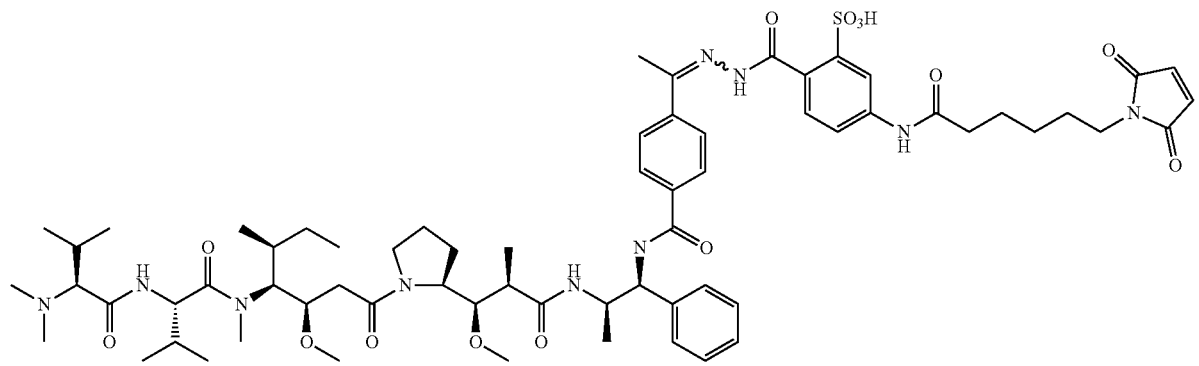

Formula IV

The present disclosure also provides a pharmaceutical composition comprising a compound as disclosed herein, and a pharmaceutically acceptable carrier. In some embodiments, the pharmaceutically acceptable carrier is selected from one or more of a solubilizing agent, an encapsulating agent and a lyoprotectant. In other embodiments, the pharmaceutically acceptable carrier comprises one or more of dimethyl-β-cyclodextrin, hydroxyethyl-β-cyclodextrin, hydroxypropyl-β-cyclodextrin, and trimethyl-β-cyclodextrin.

In some embodiments, the pharmaceutical composition is suitable for intravenous administration. In some embodiments, the composition, when administered intravenously to a patient, covalently binds selectively and rapidly in situ to endogenous albumin in blood circulation. In other embodiments, the composition, when administered intravenously to a patient, covalently binds selectively and rapidly in situ to a thiol group of cysteine-34 of endogenous albumin in blood circulation.

The present disclosure also provides a method for treating a patient suffering from a disease selected from a cancer, a virus disease, autoimmune disease, acute or chronic inflammatory disease, and a disease caused by bacteria, fungi, and other micro-organisms, comprising administering to the patient in need thereof a therapeutically effective amount of a compound or a pharmaceutical composition as described herein. In some embodiments, the disease is cancer and is selected from carcinoma, sarcoma, leukemia, lymphoma, multiple myeloma, and melanoma. In some embodiments, the administration is intravenous administration.

The present disclosure also provides a method of reducing cytotoxicity of a compound comprising administering a compound or a pharmaceutical composition as disclosed herein to a patient in need thereof, wherein the administration results in a reduction in cytotoxicity when compared to an equivalent dose of unmodified active agent.

The present disclosure further provides a method of increasing the concentration of a metabolite of a compound in a tumor, comprising administering a compound or a pharmaceutical composition as disclosed herein to a patient in need thereof, wherein the increase is compared to an equivalent dose of unmodified active agent.

The present disclosure provides a compound as disclosed herein for use as a medicament.

The present disclosure also provides a compound as disclosed herein for use in treating a disease or condition selected from the group consisting of a cancer, a virus disease, autoimmune disease, acute or chronic inflammatory disease, and a disease caused by bacteria, fungi, or other micro-organisms.

The present disclosure further provides use of a compound or a composition as disclosed herein in the preparation of a medicament for the treatment of a disease or condition selected from a cancer, a virus disease, autoimmune disease, acute or chronic inflammatory disease, and a disease caused by bacteria, fungi, or other micro-organisms.

DETAILED DESCRIPTION

Figure 1:
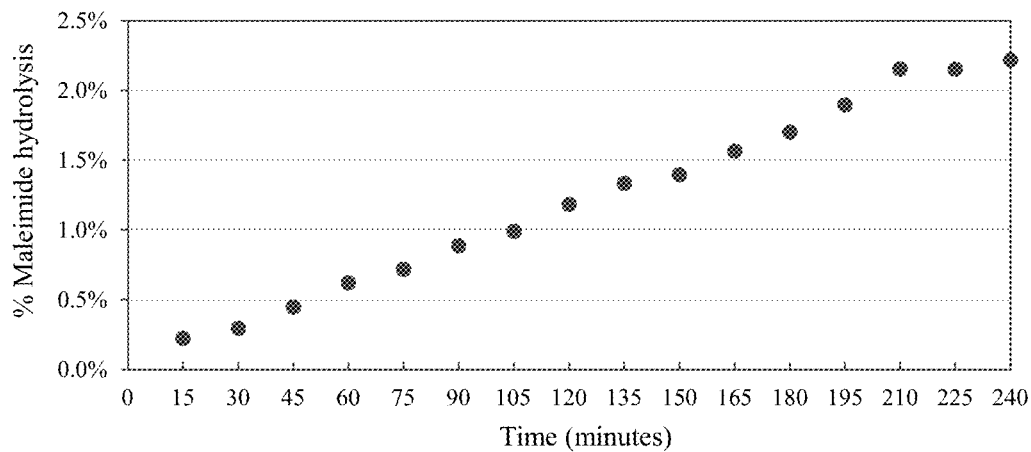
FIG. 1 compares the stability of AE-Keto-Sulf07 (Panel (a)) and AE-Keto-EMCH (Panel (b)) in the reconstitution buffer (50 mM sodium phosphate buffer pH 7.65, 5% sucrose (w/v) and 2% 2-hydroxypropyl-β-cyclodextrin (2-HPβCD (w/v)).
Figure 1:
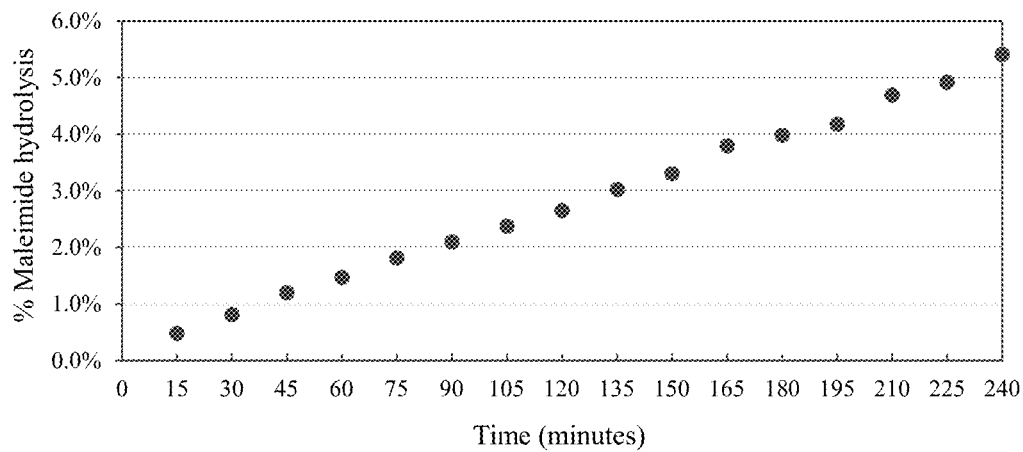

Unless otherwise defined herein, scientific and technical terms used in this application shall have the meanings that are commonly understood by those of ordinary skill in the art. Generally, nomenclature relating to techniques of chemistry, molecular biology, cell and cancer biology, immunology, microbiology, pharmacology, and protein chemistry, described herein, are those well-known and commonly used in the art.

All publications, patents and published patent applications referred to in this application are specifically incorporated by reference herein. In case of conflict, the present specification, including its specific definitions, will control. Unless otherwise specified, it is to be understood that each embodiment disclosed herein may be used alone or in combination with any one or more other embodiments disclosed herein.

Definitions

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout the application, where a compound or composition is described as having, including, or comprising, specific components, it is contemplated that such compound or composition also may consist essentially of, or consist of, the recited components. Similarly, where methods or processes are described as having, including, or comprising specific process steps, the processes also may consist essentially of, or consist of, the recited processing steps. Further, it should be understood that the order of steps or order for performing certain actions is immaterial so long as the compounds, compositions and methods described herein remains operable. Moreover, two or more steps or actions can be conducted simultaneously.

The singular forms "a," "an," and "the" include the plurals unless the context clearly dictates otherwise.

The term "including" is used to mean "including but not limited to." "Including" and "including but not limited to" are used interchangeably.

The term "or" as used herein should be understood to mean "and/or", unless the context clearly indicates otherwise.

The terms "drug," "agent," "therapeutic agent", "therapeutically active agent", "cytotoxic agent or drug", "highly cytotoxic agent or drug", or "therapeutically effective substance" are used to mean any compound which brings about a pharmacological effect either by itself or after its conversion in the organism in question, and thus also includes the derivatives from these conversions. The pharmacological effect of the drugs of the composition according to the present disclosure can be a single effect only, e.g. a cytostatic and/or cytotoxic effect, or a broad pharmacological spectrum of actions, such as an immunosuppressive and antiphlogistic effect at the same time.

The terms "patient," "subject," or "individual" are used interchangeably and refer to either a human or a non-human animal. These terms include mammals such as humans, primates, livestock animals (e.g., bovines, porcines), companion animals (e.g., canines, felines) and rodents (e.g., mice and rats). In certain embodiments, the patient or subject is a human patient or subject, such as a human patient having a condition in need of treatment.

The term "pharmaceutical composition" refers to a composition suitable for pharmaceutical use in a subject animal, including humans and mammals, e.g., combined with one or more pharmaceutically acceptable carriers, excipients or solvents. Such a composition may also contain diluents, fillers, salts, buffers, stabilizers, solubilizers, protectants and other materials well known in the art. In certain embodiments, a pharmaceutical composition encompasses a composition comprising the active ingredient(s), and the inert ingredient(s) that make up the excipient, carrier or diluent, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and one or more pharmaceutically acceptable excipient(s), carrier(s) and/or diluent(s).

The term "pharmaceutically acceptable carrier" refers to a non-toxic carrier that may be administered to a patient, together with a therapeutically effective substance disclosed herein, and which does not destroy the pharmacological activity of the agent. The term "excipient" refers to an additive in a formulation or composition that is not a pharmaceutically active ingredient. In certain embodiments, a "pharmaceutically acceptable" substance is suitable for use in contact with cells, tissues or organs of animals or humans without excessive toxicity, irritation, allergic response, immunogenicity or other adverse reactions, in the amount used in the dosage form according to the dosing schedule, and commensurate with a reasonable benefit/risk ratio. In certain embodiments, a "pharmaceutically acceptable" substance that is a component of a pharmaceutical composition is, in addition, compatible with the other ingredient(s) of the composition. In certain embodiments, the terms "pharmaceutically acceptable excipient", "pharmaceutically acceptable carrier" and "pharmaceutically acceptable diluent" encompass, without limitation, pharmaceutically acceptable inactive ingredients, materials, compositions and vehicles, such as liquid fillers, solid fillers, diluents, excipients, carriers, solvents and encapsulating materials. Carriers, diluents and excipients also include all pharmaceutically acceptable dispersion media, coatings, buffers, isotonic agents, stabilizers, absorption delaying agents, antimicrobial agents, antibacterial agents, antifungal agents, adjuvants, etc. Except insofar as any conventional excipient, carrier or diluent is incompatible with the active ingredient, the present disclosure encompasses the use of conventional excipients, carriers and diluents in pharmaceutical compositions. See, e.g. Remington: The Science and Practice of Pharmacy, 21st Ed., Lippincott Williams & Wilkins (Philadelphia, Pa., 2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla., 2004).

The terms "pharmaceutically effective amount," "therapeutically effective amount," or "therapeutically effective dose" refer to an amount effective to treat a disease in a patient, e.g., effecting a beneficial and/or desirable alteration in the general health of a patient suffering from a disease (e.g., cancer), treatment, healing, inhibition or amelioration of a physiological response or condition, etc. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of disease, the therapeutics or combination of therapeutics selected for administration, and the mode of administration. The skilled worker can readily determine the effective amount for a given situation by routine experimentation. The skilled worker will recognize that treating cancer includes, but is not limited to, killing cancer cells, preventing the growth of new cancer cells, causing tumor regression (a decrease in tumor size), causing a decrease in metastasis, improving vital functions of a patient, improving the well-being of the patient, decreasing pain, improving appetite, improving the patient's weight, and any combination thereof. The terms "pharmaceutically effective amount," "therapeutically effective amount," or "therapeutically effective dose" also refer to the amount required to improve the clinical symptoms of a patient. The therapeutic methods or methods of treating cancer described herein are not to be interpreted or otherwise limited to "curing" cancer.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation, amelioration, or slowing the progression, of one or more symptoms or conditions associated with a condition, e.g., cancer, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Exemplary beneficial clinical results are described herein.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. When a method is part of a therapeutic regimen involving more than one agent or treatment modality, the disclosure contemplates that the agents may be administered at the same or differing times and via the same or differing routes of administration. Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity).

The term "substituted" refers to moieties having substituents replacing a hydrogen on one or more carbons of the backbone of a chemical compound. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the disclosure, the heteroatoms such as nitrogen may have hydrogen substituents, and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic (e.g., $C_6$-$C_{12}$ aryl) or heteroaromatic (e.g., heteroaryl) moiety.

"Optional" or "optionally" means that the subsequently described circumstance may or may not occur, so that the application includes instances where the circumstance occurs and instances where it does not. For example, the phrase "optionally substituted" means that a non-hydrogen substituent may or may not be present on a given atom, and, thus, the application includes structures wherein a non-hydrogen substituent is present and structures wherein a non-hydrogen substituent is not present.

Unless specifically stated as "unsubstituted," references to chemical moieties herein are understood to include substituted variants. For example, reference to an "alkyl" group or moiety implicitly includes both substituted and unsubstituted variants. Examples of substituents on chemical moieties include but is not limited to, halogen, hydroxyl, carbonyl (such as carboxyl, alkoxycarbonyl, formyl, or acyl), thiocarbonyl (such as thioester, thioacetate, or thioformate), alkoxyl, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, heterocyclyl, aralkyl, or aryl or heteroaryl moiety.

"Aryl" indicates an aromatic carbon ring having the indicated number of carbon atoms, for example, 6 to 12 or 6 to 10 carbon atoms, in the ring. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups).

"Heteroaryl" indicates an aromatic ring containing the indicated number of ring atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. 5-Membered heteroaryl is a heteroaryl having 5 ring atoms. 6-Membered heteroaryl is a heteroaryl having 6 ring atoms. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,3,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

The term "acyl" is art-recognized and refers to a group represented by the general formula hydrocarbyl-C(O)—, e.g., alkyl-C(O)—.

The term "alkyl" refers to the radical of saturated aliphatic groups, including straight-chain alkyl groups, and branched-chain alkyl groups. In some embodiments, a straight chain or branched chain alkyl has 30 or fewer carbon atoms in its backbone (e.g., $C_1$-$C_{30}$ for straight chains, $C_4$-$C_{30}$ for branched chains), and in other embodiments, 20 or fewer. In certain embodiments, alkyl groups are lower alkyl groups, e.g., methyl, ethyl, n-propyl, i-propyl, n-butyl and n-pentyl. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In some embodiments, the chain has ten or fewer carbon ($C_1$-$C_{10}$) atoms in its backbone. In other embodiments, the chain has six or fewer carbon ($C_1$-$C_6$) atoms in its backbone.

The terms "hydrazone moiety" or "hydrazone" refer to E and/or Z hydrazones, e.g.,

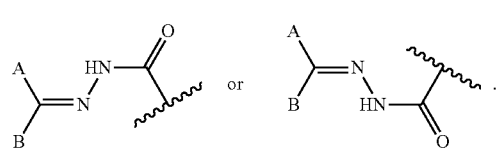

The stereochemistry of the hydrazone moiety can be E or Z. The term hydrazone as used herein includes both E and Z isomers. The hydrazone moieties disclosed herein are generally drawn in one configuration, but it is understood that this disclosure can include both E and/or Z.

At various places in the present specification substituents of compounds of the disclosure are disclosed in groups or in ranges. It is specifically intended that the disclosure includes each and every individual sub-combination of the members of such groups and ranges. For example, the term "$C_1$-$C_6$ alkyl" is specifically intended to individually disclose methyl, ethyl, propyl, isopropyl, n-butyl, sec-butyl, isobutyl, etc.

A "pharmaceutically acceptable salt" is a salt of a compound that is suitable for pharmaceutical use, including but not limited to metal salts (e.g., sodium, potassium, magnesium, calcium, etc.), acid addition salts (e.g., mineral acids, carboxylic acids, etc.), and base addition salts (e.g., ammonia, organic amines, etc.). The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like (See, e.g., WO 01/062726. Some pharmaceutically acceptable salts listed by Berge et al., J. Pharm. Sci., 66: 1-19 (1977), incorporated herein by reference in its entirety). Compounds containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts or ions, e. g., lithium, sodium, potassium, magnesium, calcium salts and the like, salts with organic bases, e. g. N-methyl-D-glucamine, hydrabamine salts, and salts with amino acids such as, for example, arginine, lysine and the like. Conversely, said salt forms can be converted into the free forms by treatment with an appropriate base or acid. Compounds and their salts can be in the form of a solvate, which is included within the scope of the present disclosure. Such solvates include for example hydrates, alcoholates and the like (see, e.g., WO 01/062726).

The disclosure further provides pharmaceutical compositions comprising one or more compounds of the disclosure together with a pharmaceutically acceptable carrier or excipient. Compounds or pharmaceutical compositions of the disclosure may be used in vitro or in vivo.

The term "isomer" as used herein includes, but is not limited to, tautomers, cis- and trans-isomers (E (entgegen), Z (zusammen)), R- and S-enantiomers (said R and S notation is used in correspondence with the rules described in Pure Appl. Chem. (1976), 45, 11-30), diastereomers, (D)-isomers, (L)-isomers, stereoisomers, the racemic mixtures thereof, and other mixtures thereof. All such isomers, as well as mixtures thereof, are intended to be included in this disclosure. Tautomers, while not explicitly indicated in the formulae described herein, are intended to be included within the scope of the present disclosure.

Compounds of the Disclosure

Embodiments of the present disclosure provide a compound having the structure represented by Formula I or Formula II:

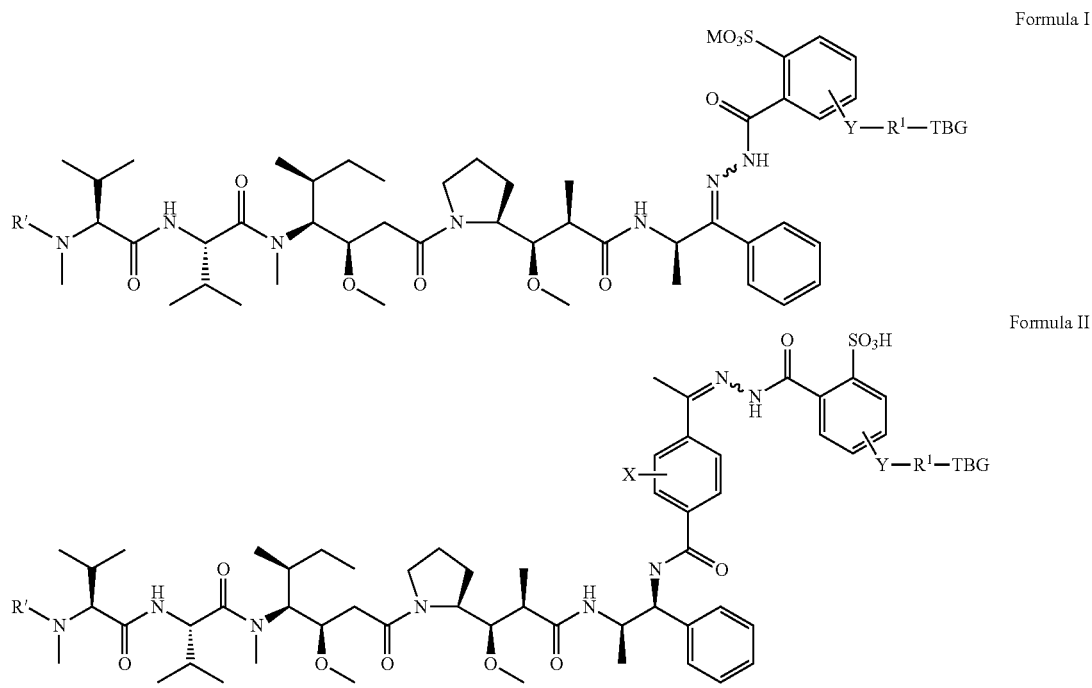

or a pharmaceutically acceptable salt, hydrate, solvate, or isomer thereof, wherein:

R' is H or —$CH_3$,

M is selected from H and a pharmaceutically acceptable counterion, such as, $Na^+$, $K^+$, $NR_4^+$, or $NHR_3^+$, wherein R is selected from H and $C_1$-$C_4$ alkyl, Y is absent or selected from an optionally substituted $C_1$-$C_6$ alkyl, —NH—C(O)—, —C(O)—NH—, —NH—C(O)—NH—, —C(O)—O—, and —O—C(O)—, $R^1$ is absent or an optionally substituted $C_1$-$C_{18}$ alkyl wherein optionally up to six carbon atoms in said $C_1$-$C_{18}$ alkyl are each independently replaced with —OCH$_2$CH$_2$—, X is H or selected from halogen (e.g., —F, —Cl, —Br or —I), —NO$_2$, —NR$^2$R$^3$, —OR$^2$, —NHCOR$^2$ and —OCOR$^2$, wherein R$^2$ and R$^3$ are each independently selected from H and $C_1$-$C_4$ alkyl, and TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, and an optionally substituted acetylene group.

In some embodiments, the compound of the structure of Formula I or II is formulated as a pharmaceutical composition containing optionally a pharmaceutically acceptable carrier, is administered to an organism and covalently binds selectively and rapidly in situ to the thiol group of cysteine-34 of endogenous albumin in the blood circulation.

In some embodiments, R' is —CH$_3$. In other embodiments, R' is H.

In some embodiments, the thiol-binding group, TBG, is the maleimide group:

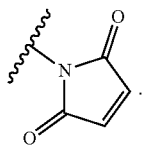

In some embodiments, the highly cytotoxic peptide-based drug is auristatin E derivatized in such a way that is contains a carbonyl group that enables the formation of an acid-sensitive hydrazone bond with a maleimide water-solubilizing linker containing a hydrazide moiety.

In some embodiments, the disclosure provides a pharmaceutical composition comprising a compound as disclosed herein, and optionally a pharmaceutically acceptable carrier, wherein the pharmaceutical composition is administered intravenously and covalently binds selectively and rapidly in situ to the thiol group of cysteine-34 of endogenous albumin in the blood circulation.

In some embodiments, in the albumin-binding compounds disclosed herein, the highly cytotoxic drug is a carbonyl containing pentapeptide derivative of auristatin E, the albumin-binding moiety is a thiol-binding group (TBG), for example, a maleimide group, that binds rapidly and selectively to the cysteine-34 of albumin after administration, and the acid-sensitive bond is a derivatized benzoyl hydrazone bond of the general Formula I and II:

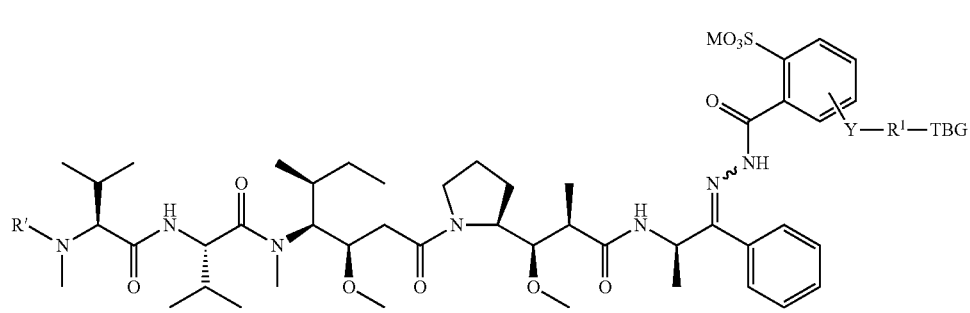

Formula I

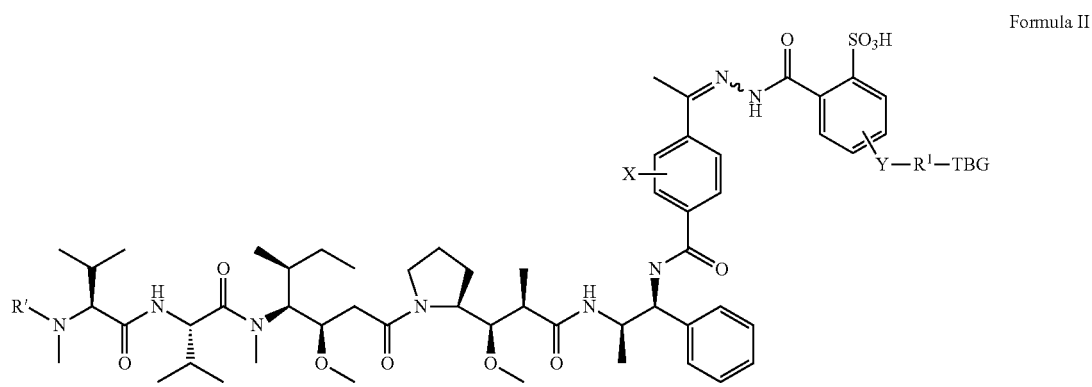

Formula II or a pharmaceutically acceptable salt, hydrate, solvate, or isomer thereof, wherein:

R' is H or —$CH_3$,

M is selected from H and a pharmaceutically acceptable counterion, such as, $Na^+$, $K^+$, $NR_4^+$, or $NHR_3$, wherein R is selected from H and $C_1$-$C_4$ alkyl, Y is absent or selected from an optionally substituted $C_1$-$C_6$ alkyl, —NH—C(O)—, —C(O)—NH—, —NH—C(O)—NH—, —C(O)—O—, and —O—C(O)—, $R^1$ is absent or an optionally substituted $C_1$-$C_{18}$ alkyl wherein optionally up to six carbon atoms in said $C_1$-$C_{18}$ alkyl are each independently replaced with —$OCH_2CH_2$—, X is H or selected from halogen (e.g., —F, —Cl, —Br or —I), —$NO_2$, —$NR^2R^3$, —$OR^2$, —$NHCOR^2$ and —$OCOR^2$, wherein $R^2$ and $R^3$ are each independently selected from H and $C_1$-$C_4$ alkyl, and TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, and an optionally substituted acetylene group.

In some embodiments, TBG is substituted with $C_1$-$C_6$ alkyl or halogen. In some embodiments, TBG is substituted with methyl, —Cl or —Br.

A disulfide group may be activated by a thionitrobenzoic acid (e.g. 5'-thio-2-nitrobenzoic acid) as the exchangeable group. A maleimide or pyridyldithio group can, where appropriate, be substituted by an alkyl group or by the above water-soluble groups. In general, a thiol-binding group possesses protein-binding properties, i.e., it binds covalently ("a covalent protein-binding group") in a physiological environment, to particular amino acids on the surface of the protein. In some embodiments, the maleimide group, the haloacetamide group, the haloacetate group, the pyridyldithio group, the disulfide group, the vinylcarbonyl group, the aziridine group, and/or the acetylene group reacts with thiol (—SH) groups of cysteines. In some embodiments, the protein-binding group is a maleimide group

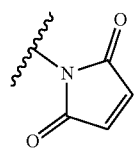 [SMILES: *N1C(=O)C=CC1=O]

that binds to cysteine-34 of albumin.

In some embodiments, the drug delivery system contains an acid-sensitive, cleavable hydrazone moiety. The cleavage of the hydrazone moiety and the half-life of the drug release vary according to the structure of the carbonyl derivative.

In some embodiments, the half-life of the release of the albumin-bound drug release in the pH range of 4.0-6.5 varies from about 1.5 hours to about 80 hours.

Without being bound by theory, a phenyl ring comprising one electron-withdrawing group such as a sulfonic acid (—$SO_3H$) or sulfonate group (—$SO_3$) attached to the ortho-position to the hydrazone bond, stabilizes the hydrazone moiety resulting in a slow and prolonged release of the drug in acidic conditions.

In some embodiments, R' is —$CH_3$. In other embodiments, R' is H.

In some embodiments, Y and/or $R^1$ are present. In some embodiments, Y is absent. In some embodiments, $R^1$ is absent. In some embodiments, both Y and $R^1$ are absent.

In some embodiments, Y is selected from methyl, ethyl, —NH—C(O)—, —C(O)—NH—, —C(O)—O—, and —O—C(O)—.

In some embodiments, $R^1$ is optionally substituted $C_1$-$C_{18}$ alkyl. In some embodiments, $R^1$ is optionally substituted $C_1$-$C_{18}$ alkyl wherein one carbon atom in said $C_1$-$C_{18}$ alkyl is replaced with —$OCH_2CH_2$—. In some embodiments, $R_1$ is optionally substituted $C_1$-$C_{18}$ alkyl wherein two carbon atoms in said $C_1$-$C_{18}$ alkyl are replaced with —$OCH_2CH_2$—. In some embodiments, $R^1$ is optionally substituted $C_1$-$C_{18}$ alkyl wherein three carbon atoms in said $C_1$-$C_{18}$ alkyl are replaced with —$OCH_2CH_2$—. In some embodiments, $R^1$ is optionally substituted $C_1$-$C_{18}$ alkyl wherein four carbon atoms in said $C_1$-$C_{18}$ alkyl are replaced with —$OCH_2CH_2$—. In some embodiments, $R^1$ is optionally substituted $C_1$-$C_{18}$ alkyl wherein five carbon atoms in said $C_1$-$C_{18}$ alkyl are replaced with —$OCH_2CH_2$—. In some embodiments, $R^1$ is optionally substituted $C_1$-$C_{18}$ alkyl wherein six carbon atoms in said $C_1$-$C_{18}$ alkyl are replaced with —$OCH_2CH_2$—.

U.S. Pat. No. 6,884,869-B2 (application Ser. No.: 10/001,191, filed, Jan. 11, 2001) describes antibody drug conjugates in which pentapeptide derivatives of the chemical structures of Formula A and Formula B depicted below:

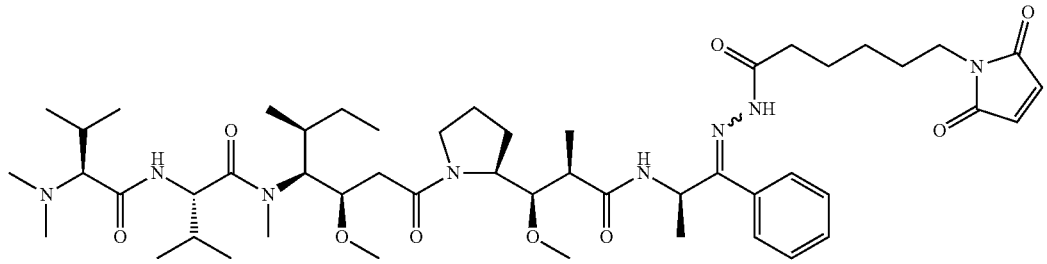

Formula A

-continued

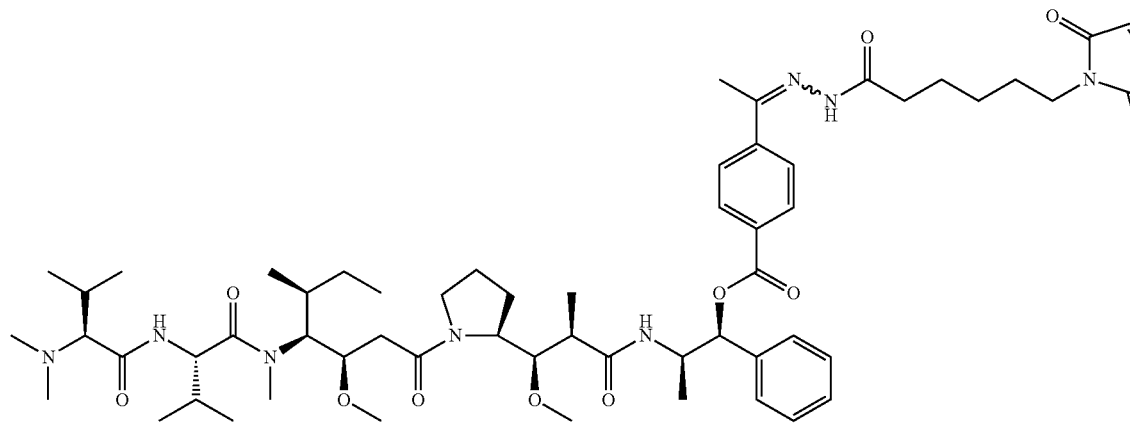

Formula B

These were conjugated to thiol-containing antibodies. Both compounds contain an aliphatic 6-maleimidocaproyl hydrazone moiety that renders minimal aqueous solubility to the two compounds of Formula A and Formula B depicted above. Indeed, conjugation of both former compounds to the antibodies was achieved by dissolution of the compounds only with the aid of organic solvents, i.e. a 9:1 mixture of acetonitrile:DMSO. The use of solely organic solvents in the formulation of an applicable pharmaceutical composition for in situ coupling to the cysteine-34 of albumin circulating in the bloodstream, namely the drug delivery approach described herein, is not possible. Accordingly, in some embodiments, the present compositions do not include an organic solvent.

Thus, aromatic maleimide linkers comprising a sulfonic acid moiety were invented rendering sufficient aqueous solubility to the albumin-binding prodrugs for the formulation of a pharmaceutical composition for intravenous administration. One such linker is 5-(6-(2,5-dioxo-2,5-dihydro-1H-pyrrol-1-yl)hexanamido)-2-(hydrazinecarbonyl)-benzenesulfonic acid, abbreviated Sulf07, having the chemical structure depicted below:

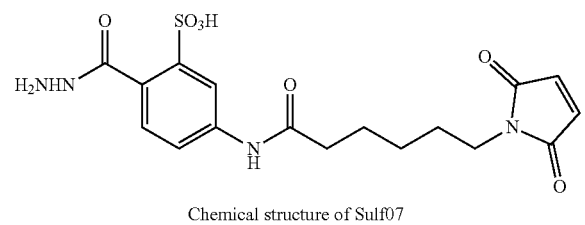

Chemical structure of Sulf07

The linker Sulf07, 5-(6-(2,5-dioxo-2,5-dihydro-1H-pyrrol-1-yl)hexanamido)-2-(hydrazinecarbonyl)-benzenesulfonic acid, was prepared according to route A and/or route B as depicted in the following synthetic schemes:

Scheme 1, Route A

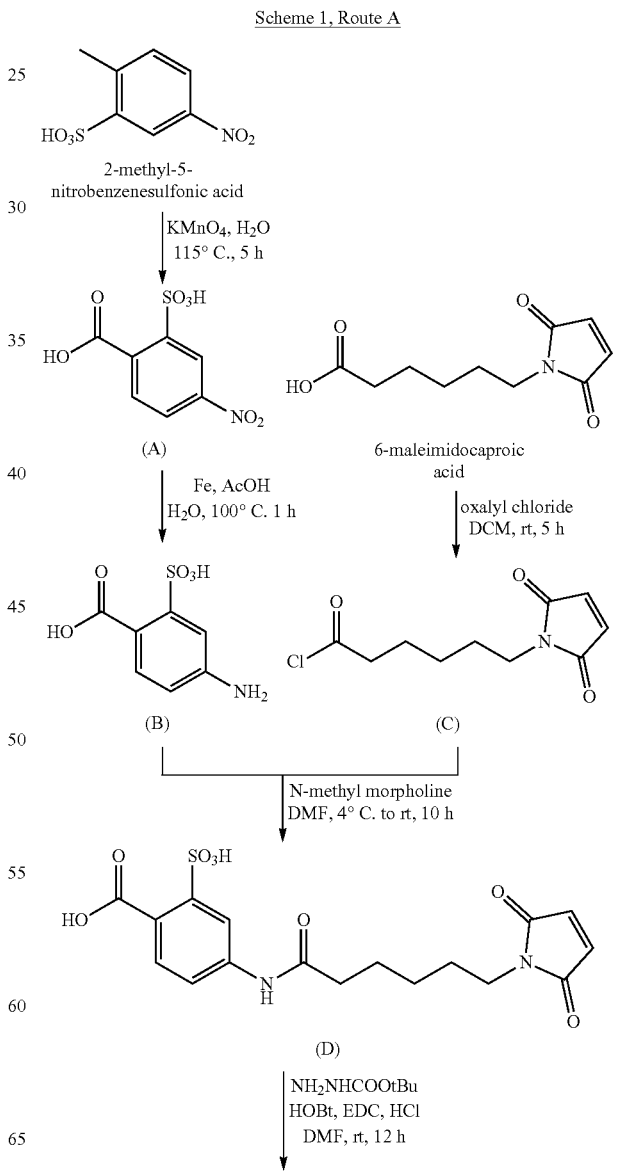

21
-continued
22
-continued
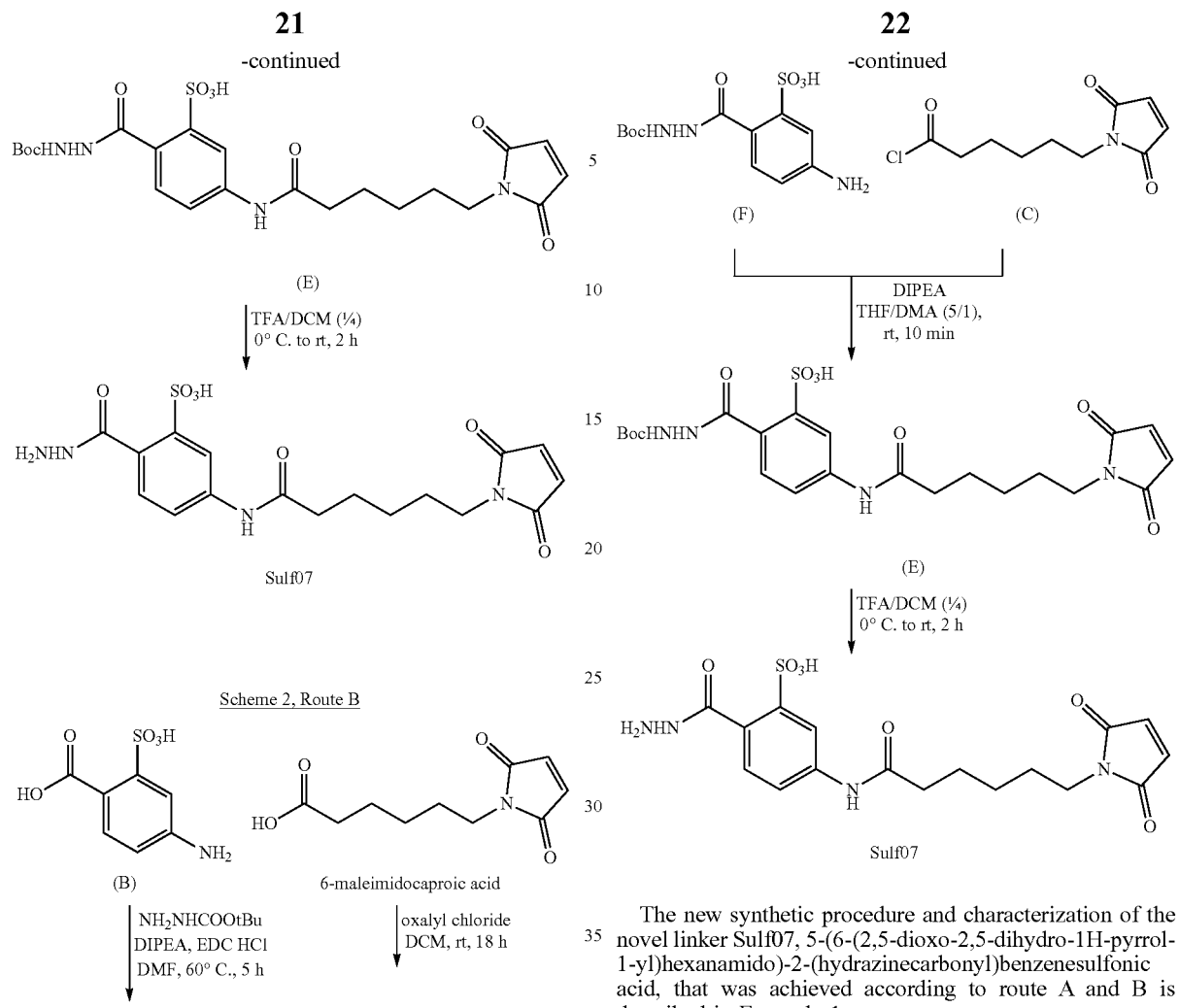
The new synthetic procedure and characterization of the novel linker Sulf07, 5-(6-(2,5-dioxo-2,5-dihydro-1H-pyrrol-1-yl)hexanamido)-2-(hydrazinecarbonyl)benzenesulfonic acid, that was achieved according to route A and B is described in Example 1.
Linker Sulf07 was reacted with:
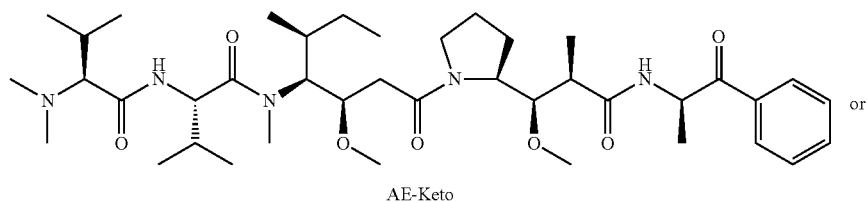
AE-Keto
or
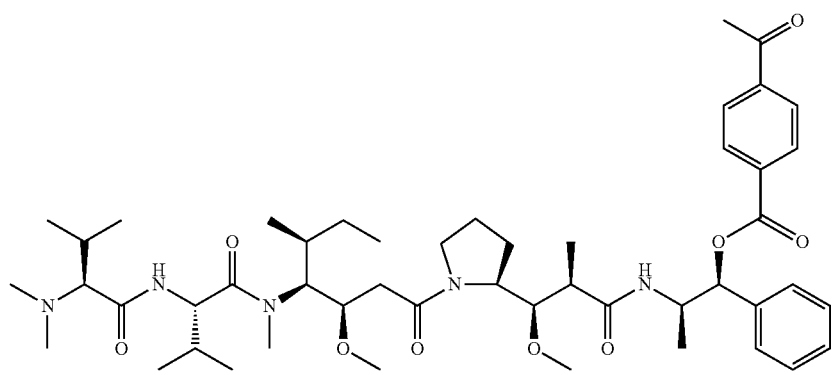

AE-Ester in order to obtain the compounds of Formula III (abbreviated AE-Keto-Sulf07) and Formula IV (abbreviated AE-Ester-Sulf07), respectively:

Formula III

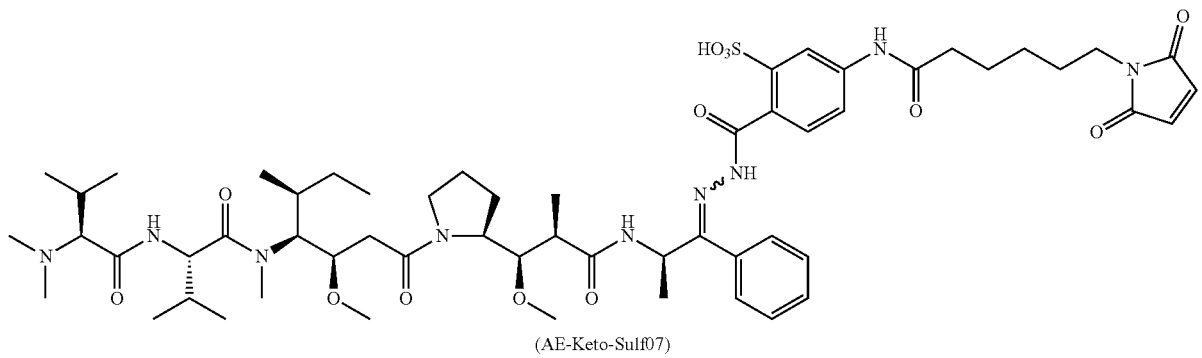

(AE-Keto-Sulf07)

Formula IV

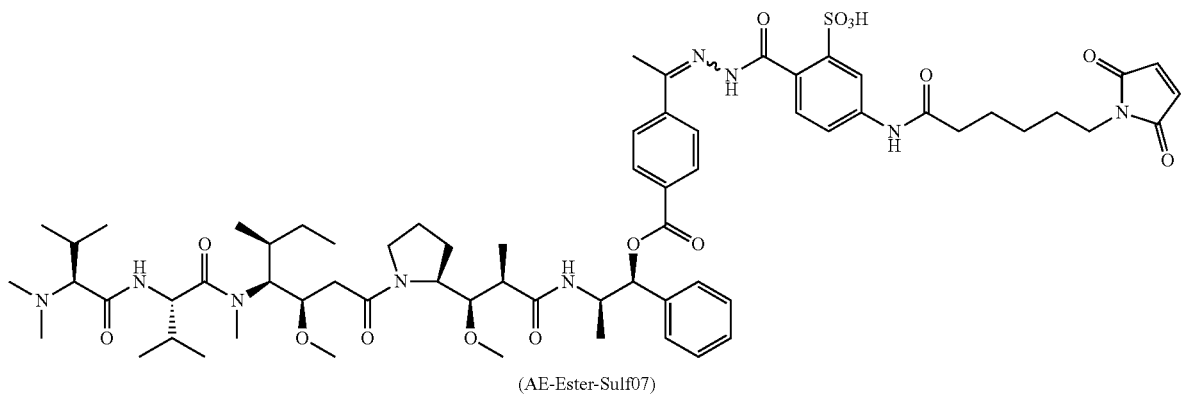

(AE-Ester-Sulf07)

The synthesis and characterization of AE-Keto-Sulf07 (Formula III) and AE-Ester-Sulf07 (Formula IV) is described in Examples 2 and 3.

The analyses of the structures of AE-Keto-Sulf07 and AE-Ester-Sulf07 reveal that in both molecules two moieties (—$SO_3H$ and —$N(CH_3)_2$ groups) exist as an acid-base pair, thus forming zwitterions depicted in Scheme 3 and Scheme 4.

Scheme 3

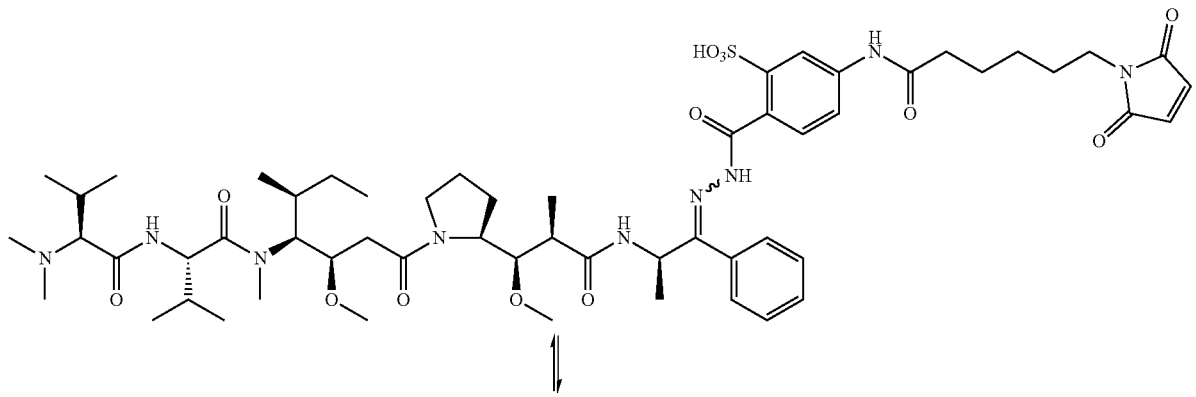

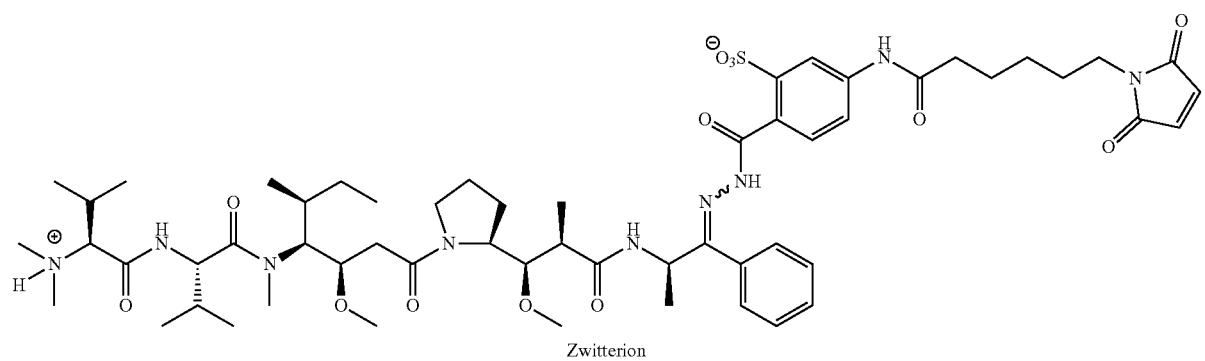
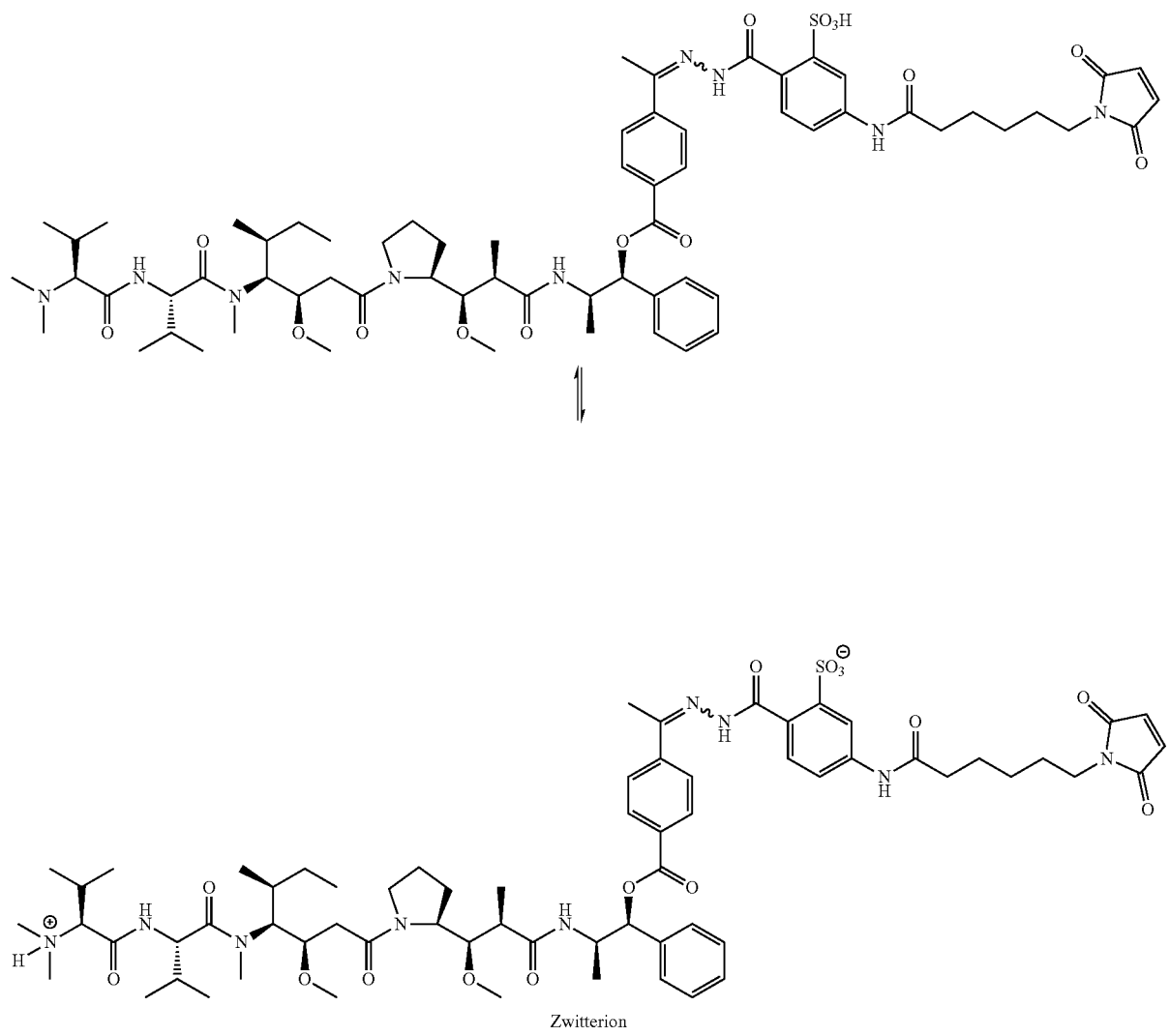
Scheme 4

The sulfonic acid moiety integrated in the linker Sulf07 as well as the zwitterionic property of the two auristatin prodrugs AE-Keto-Sulf07 and AE-Ester-Sulf07 provide sufficient aqueous solubility for formulating a pharmaceutical composition and more importantly a high stability of the maleimide moiety which is significantly improved over the Formula A (AE-Keto-EMCH) and B (AE-Ester-EMCH):

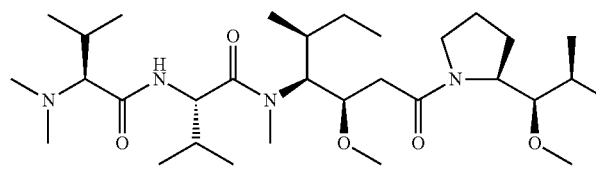

Formula A

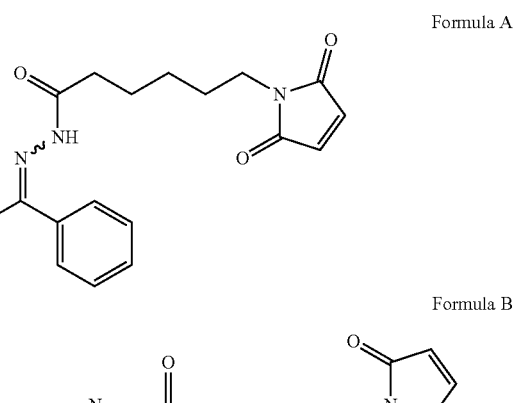

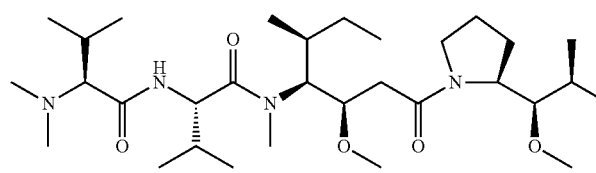

Formula B disclosed in U.S. Pat. No. 6,884,869-B2 (application Ser. No.: 10/001,191, filed, Jan. 11, 2001).

For the in situ binding to the cysteine-34 of endogenous albumin, the stability of the maleimide group under physiological conditions in the pH range of 7.4-7.6 is a criterion for intravenous administration and efficient binding to circulating albumin in the bloodstream.

Figure 2:
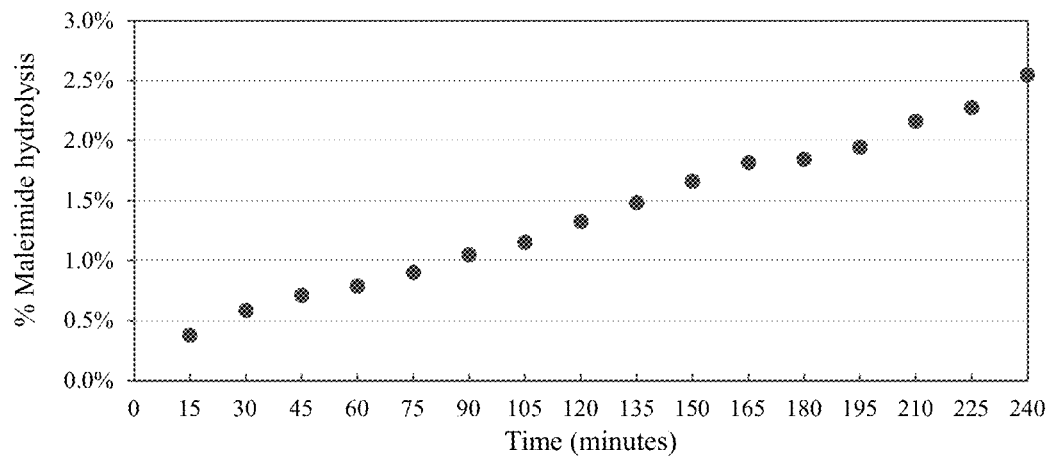
FIG. 2 compares the stability of AE-Ester-Sulf07 (Panel (a)) and AE-Ester-EMCH (Panel (b)) in the reconstitution buffer (50 mM sodium phosphate buffer pH 7.65, 5% sucrose (w/v) and 4% 2-hydroxypropyl-β-cyclodextrin (2-HPβCD, (w/v)).
Figure 2:
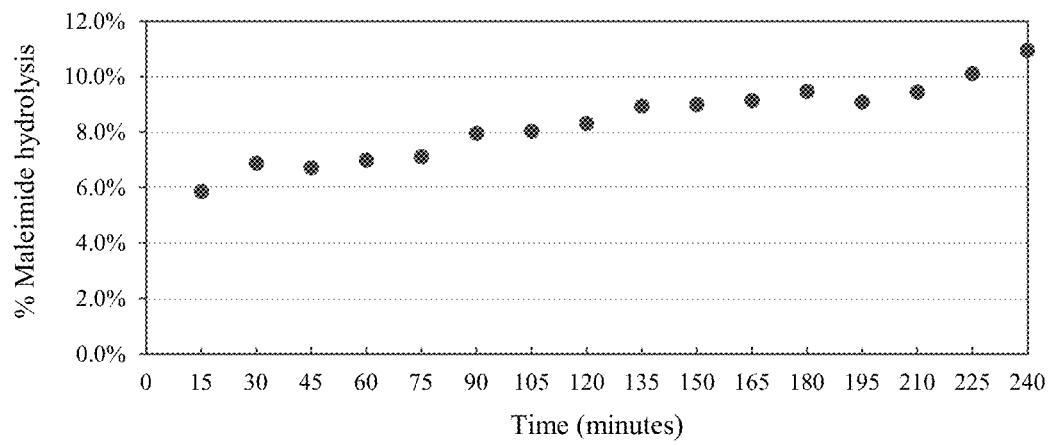

As shown in FIG. 1 and FIG. 2 the stability of the maleimide moiety against hydrolysis for both AE-Keto-Sulf07 and AE-Ester-Sulf07 is considerably improved in comparison to the two compounds described in U.S. Pat. No. 6,884,869-B2, i.e. AE-Keto-EMCH (compound of Formula A) and AE-Ester-EMCH (compound of Formula B). After 4 hours incubation at room temperature in the reconstitution buffer (50 mM sodium phosphate pH 7.65 containing 4% HPβCD and 5% sucrose), 2.2% maleimide of AE-Keto-Sulf07 were hydrolyzed in comparison to 5.4% maleimide hydrolysis for AE-Keto-EMCH, and similarly 2.5% maleimide of AE-Ester-Sulf07 were hydrolyzed in comparison to 11.0% for AE-Ester-EMCH. In addition, the active pharmaceutical ingredient (API) formulations of the Sulf07 derivatives showed excellent stability (FIG. 24 and FIG. 25) under accelerated degradation conditions (e.g., at 55° C. for up to 264 hours), while the maleimide moieties of the EMCH derivatives were rapidly hydrolyzed. Minimal maleimide hydrolysis is essential for product development and manufacture to ensure quantitative endogenous albumin binding, and thus to limit any premature free drug release in circulation and maximize clinical efficiency.

A further advantage of the aqueous solutions of AE-Keto-Sulf07 and AE-Ester-Sulf07 is that they have a physiological pH value in the range of 6.8 to 7.5.

Moreover, the solubility and stability of the zwitterion APIs increase when used in combination with pharmaceutical approved carriers such as polysorbate 80 (Tween® 80), 2-Hydroxypropyl-β-cyclodextrin, and this may facilitate the formulation of a pharmaceutical composition.

Figure 3:
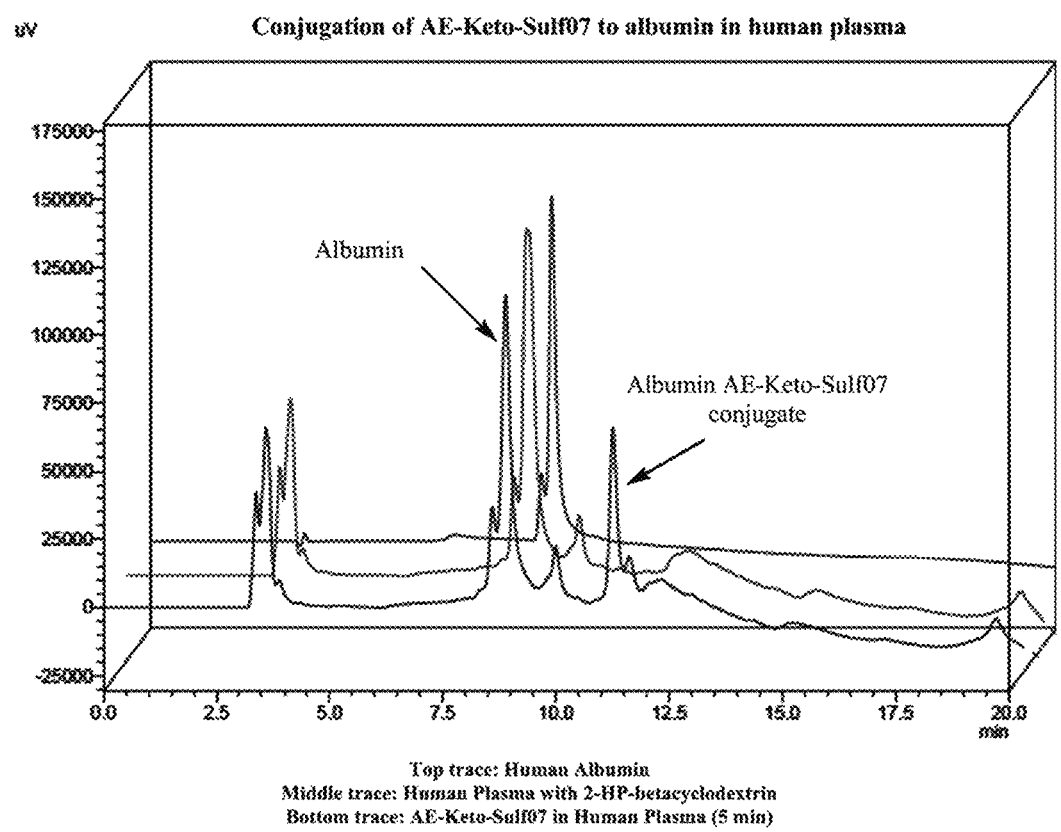
FIG. 3 shows the conjugation of AE-Keto-Sulf07 to albumin in human plasma.
Figure 4:
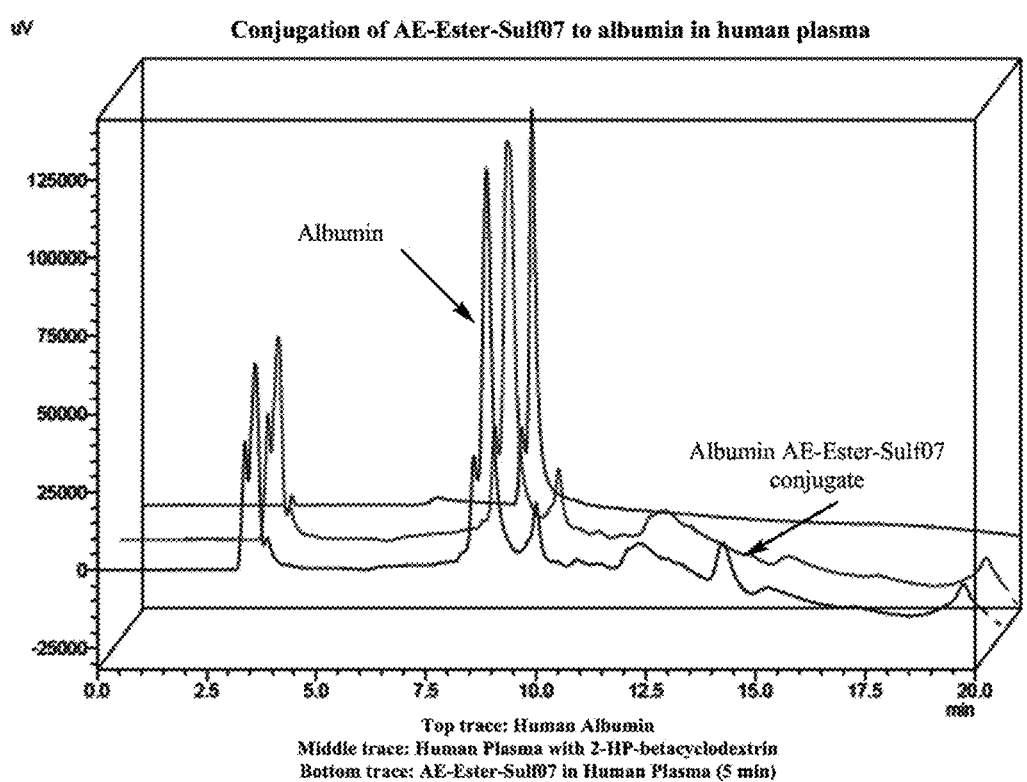
FIG. 4 shows the conjugation of AE-Ester-Sulf07 to albumin in human plasma.
Figure 5:
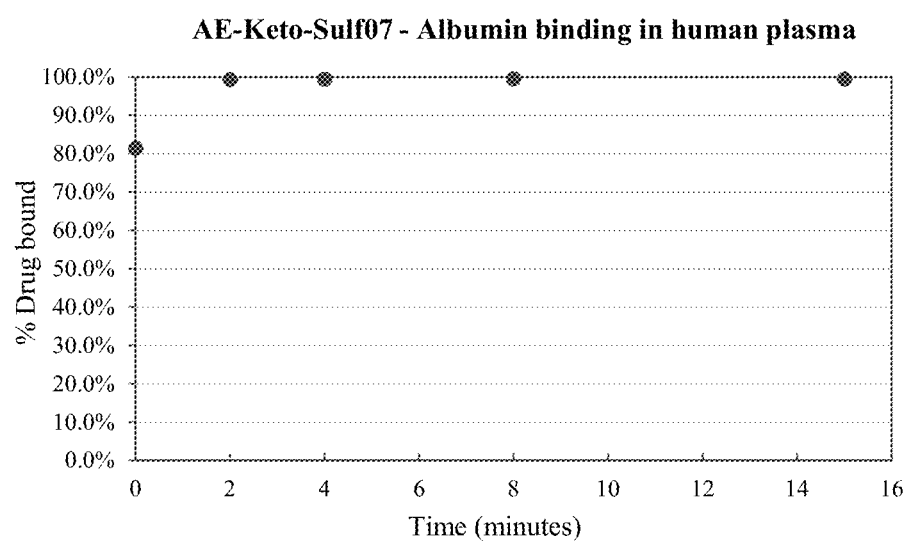
FIG. 5 shows the binding kinetics of AE-Keto-Sulf07 to albumin in human plasma.
Figure 6:
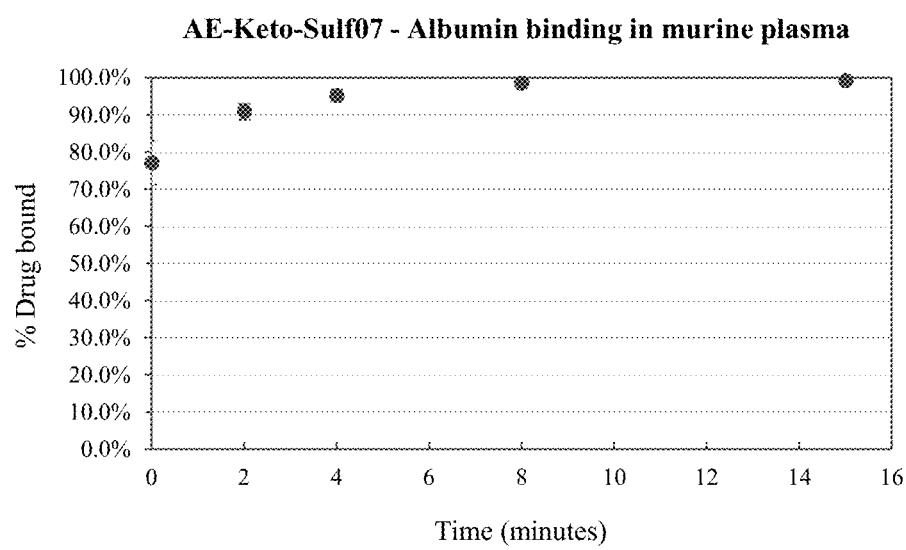
FIG. 6 shows the binding kinetics of AE-Keto-Sulf07 to albumin in murine plasma.
Figure 7:
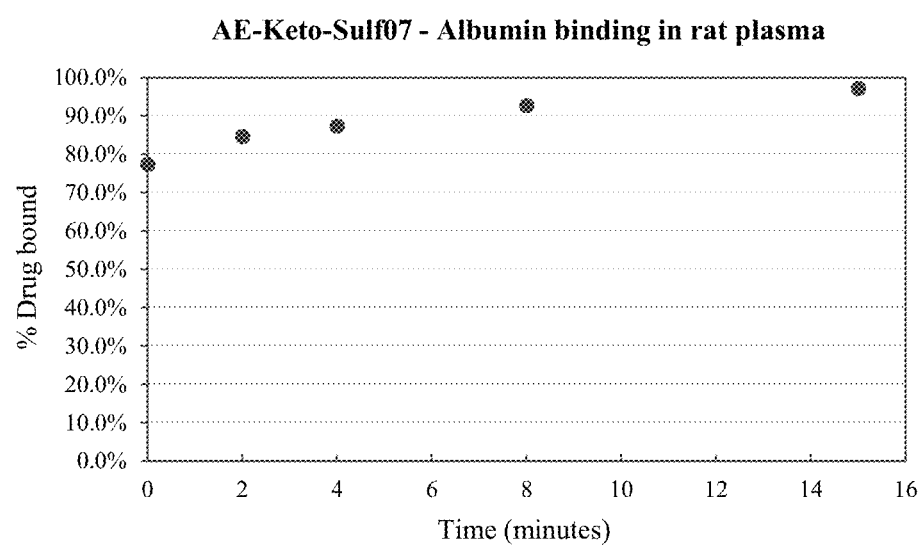
FIG. 7 shows the binding kinetics of AE-Keto-Sulf07 to albumin in rat plasma.
Figure 8:
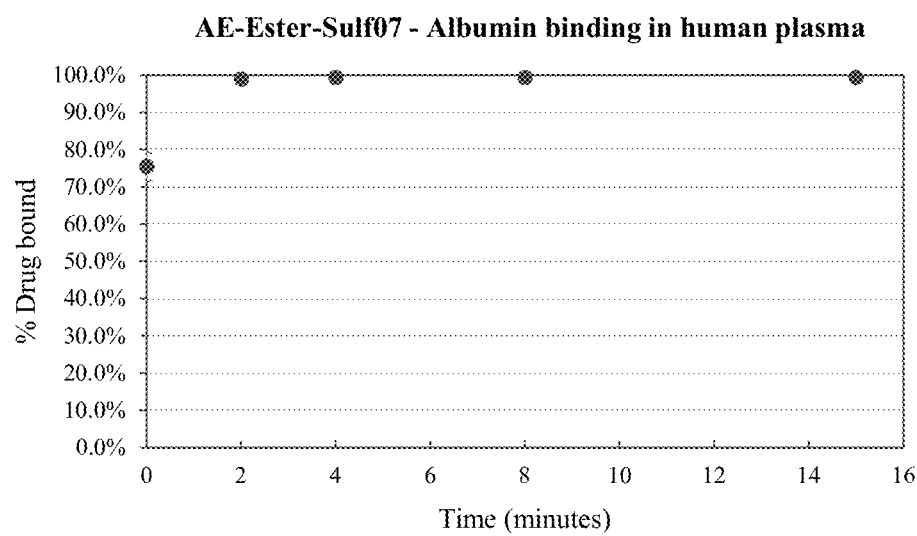
FIG. 8 shows the binding kinetics of AE-Ester-Sulf07 to albumin in human plasma.
Figure 9:
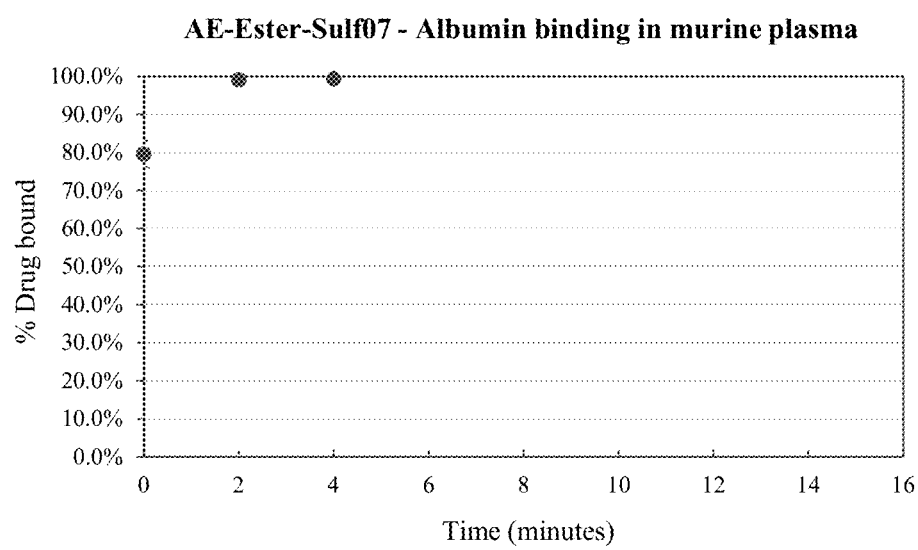
FIG. 9 shows the binding kinetics of AE-Ester-Sulf07 to albumin in murine plasma until limit of quantification (LOQ) was reached for the drug.
Figure 10:
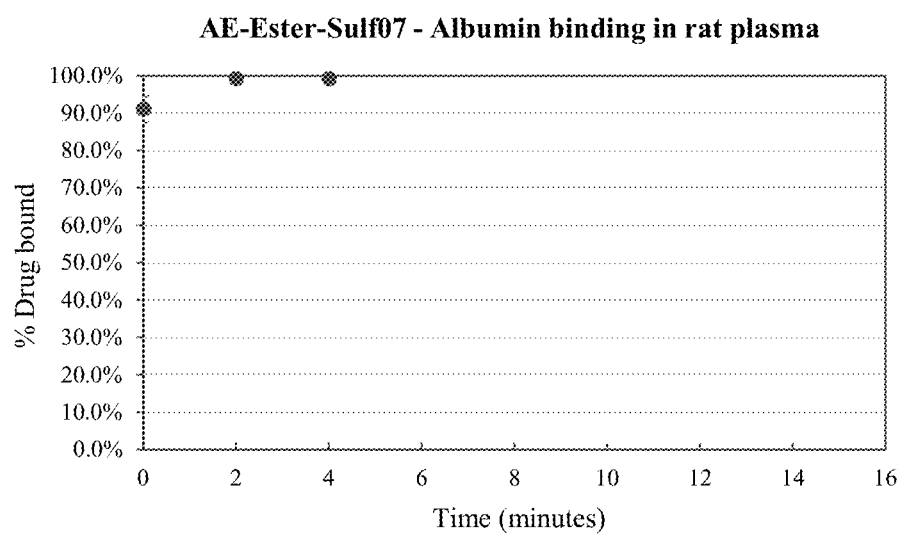
FIG. 10 shows the binding kinetics of AE-Ester-Sulf07 to albumin in rat plasma until LOQ was reached for the drug.

The pharmaceutical formulations of AE-Keto-Sulf07 and AE-Ester-Sulf07 achieved very rapid albumin binding in plasma (human, murine and rat (FIGS. 5-10)). The specificity of binding to albumin for both therapeutic agent was also demonstrated in human plasma (FIGS. 3-4).

Pharmaceutical Compositions

In some embodiments, the disclosure provides a pharmaceutical composition comprising a compound described herein.

The total amount of a compound in a composition to be administered to a patient is one that is suitable for that patient. One of skill in the art would appreciate that different individuals may require different total amounts of the therapeutically effective substance. In some embodiments, the amount of the compound is a pharmaceutically effective amount. The skilled worker would be able to determine the amount of the compound in a composition needed to treat a patient based on factors such as, for example, the age, weight, and physical condition of the patient. The concentration of the compound depends on its solubility in the intravenous administration solution and the volume of fluid that can be administered. For example, the concentration of the compound may be from about 0.1 mg/mL to about 50 mg/mL in the injectable composition. In some embodiments, the concentration of the compound may be in the range of about 0.1 mg/mL to about 40 mg/mL.

The pharmaceutical compositions and kits of the present disclosure may also contain diluents, fillers, salts, buffers, stabilizers, solubilizers, protectants and other materials well known in the art. The term "pharmaceutically acceptable" means a non-toxic material that does not interfere with the effectiveness of the biological activity of the active ingredient(s). The characteristics of the carrier will depend on the route of administration.

The compositions may be administered in a variety of conventional ways. Exemplary routes of administration that can be used include oral, parenteral, intravenous, intraarterial, cutaneous, subcutaneous, intramuscular, topical, intracranial, intraorbital, ophthalmic, intravitreal, intraventricular, intracapsular, intraspinal, intracisternal, intraperitoneal, intranasal, aerosol, central nervous system (CNS) administration, or administration by suppository. In some embodiments, the compositions are suitable for parenteral administration. These compositions may be administered, for example, intraperitoneally, intravenously, or intrathecally. In some embodiments, the compositions are injected intravenously. In some embodiments, a reconstituted formulation can be prepared by reconstituting a lyophilized compound composition in a reconstitution liquid comprising e.g. an alcohol, DMSO, and/or polyethylene glycol and water and/or a salt buffer. Such reconstitution may comprise adding the reconstitution liquid and mixing, for example, by swirling or vortexing the mixture. The reconstituted formulation then can be made suitable for injection by mixing e.g., Lactated Ringer's solution, 5% Glucose solution, isotonic saline or a suitable salt buffer with the formulation to create an injectable composition. One of skill in the art would appreciate that a method of administering a therapeutically effective substance formulation or composition would depend on factors such as the age, weight, and physical condition of the patient being treated, and the disease or condition being treated. The skilled worker would, thus, be able to select a method of administration optimal for a patient on a case-by-case basis.

In some embodiments, the compounds and compositions disclosed herein are for use in treating a cancer, a virus disease, autoimmune disease, acute or chronic inflammatory disease, and a disease caused by bacteria, fungi, or other micro-organisms.

In some embodiments, the compound disclosed herein may be used in the manufacture of a medicament for treating a disease selected from a cancer, a virus disease, autoimmune disease, acute or chronic inflammatory disease, and a disease caused by bacteria, fungi, or other micro-organisms.

In some embodiments, the cancer is a blood cancer or a solid tumor cancer. In some embodiments, the cancer is selected from carcinoma, sarcoma, leukemia, lymphoma, multiple myeloma, and melanoma.

In some embodiments, the cancer is adenocarcinoma, uveal melanoma, acute leukemia, acoustic neuroma, ampullary carcinoma, anal carcinoma, astrocytoma's, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinomas, uterine cancer, cervical cancer, neck, nose and ear tumors, hematological neoplasia's, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, colon cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer, ovary carcinoma or lymph gland cancer.

In some embodiments, the present disclosure provides a kit comprising a compound as described herein and, a pharmaceutically acceptable excipient, a carrier, and/or a diluent.

In some embodiments, one or more excipients may be included in the composition. One of skill in the art would appreciate that the choice of any one excipient may influence the choice of any other excipient. For example, the choice of an excipient may preclude the use of one or more additional excipients because the combination of excipients would produce undesirable effects. One of skill in the art would be able to empirically determine which excipients, if any, to include in the compositions. Excipients may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some embodiments, it may be beneficial to include a pharmaceutically acceptable carrier in the compositions.

In some embodiments, a solubilizing agent may be included compositions. Solubilizing agents may be useful for increasing the solubility of any of the components of the composition, including a compound or an excipient. The solubilizing agents described herein are not intended to constitute an exhaustive list, but are provided merely as exemplary solubilizing agents that may be used in the compositions. In certain embodiments, solubilizing agents include, but are not limited to, ethyl alcohol, tert-butyl alcohol, polyethylene glycol, glycerol, methylparaben, propylparaben, polyethylene glycol, polyvinyl pyrrolidone, cyclodextrins such as dimethyl-β-cyclodextrin, hydroxyethyl-β-cyclodextrin, hydroxypropyl-β-cyclodextrin, and trimethyl-β-cyclodextrin, and combinations thereof, and any pharmaceutically acceptable salts and/or combinations thereof.

The pH of the compositions may be any pH that provides desirable properties for the formulation or composition. Desirable properties may include, for example, compound stability, increased compound retention as compared to compositions at other pH values, and improved filtration efficiency. In some embodiments, the pH value of the compositions may be from about 3.0 to about 9.0, e.g., from about 5.0 to about 7.0. In particular embodiments, the pH value of the compositions may be 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, 7.0±0.1, 7.1±0.1 and 7.2±0.1.

In some embodiments, it may be beneficial to buffer the pH by including one or more buffers in the compositions. In certain embodiments, a buffer may have a pKa of, for example, about 5.5, about 6.0, or about 6.5. One of skill in the art would appreciate that an appropriate buffer may be chosen for inclusion in compositions based on its pKa and other properties. Buffers are well known in the art. Accordingly, the buffers described herein are not intended to constitute an exhaustive list, but are provided merely as exemplary buffers that may be used in the formulations or compositions of the present disclosure. In certain embodiments, a buffer includes, but is not limited to Tris, Tris-HCl, potassium phosphate, sodium phosphate, sodium citrate, sodium ascorbate, combinations of sodium and potassium phosphate, Tris/Tris-HCl, sodium bicarbonate, arginine phosphate, arginine hydrochloride, histidine hydrochloride, cacodylate, succinate, 2-(N-morpholino)ethanesulfonic acid (MES), maleate, bis-tris, phosphate, carbonate, and any pharmaceutically acceptable salts and/or combinations thereof.

In some embodiments, a pH-adjusting agent may be included in the compositions. Modifying the pH of a composition may have beneficial effects on, for example, the stability or solubility of a compound, or may be useful in making a composition suitable for parenteral administration. pH-Adjusting agents are well known in the art. Accordingly, the pH-adjusting agents described herein are not intended to constitute an exhaustive list, but are provided merely as exemplary pH-adjusting agents that may be used in the compositions. pH-Adjusting agents may include, for example, acids and bases. In some embodiments, a pH-adjusting agent includes, but is not limited to, acetic acid, hydrochloric acid, phosphoric acid, sodium hydroxide, sodium carbonate, and combinations thereof.

In some embodiments, a bulking agent may be included in the compositions. Bulking agents are commonly used in lyophilized compositions to provide added volume to the composition and to aid visualization of the composition, especially in instances where the lyophilized pellet would otherwise be difficult to see. Bulking agents also may help prevent a blowout of the active component(s) of a pharmaceutical composition and/or to aid cryoprotection of the composition. Bulking agents are well known in the art. Accordingly, the bulking agents described herein are not intended to constitute an exhaustive list, but are provided merely as exemplary bulking agents that may be used in the compositions.

Exemplary bulking agents may include carbohydrates, monosaccharides, disaccharides, polysaccharides, sugar alcohols, amino acids, and sugar acids, and combinations thereof. Carbohydrate bulking agents include, but are not limited to, mono-, di-, or poly-carbohydrates, starches, aldoses, ketoses, amino sugars, glyceraldehyde, arabinose, lyxose, pentose, ribose, xylose, galactose, glucose, hexose, idose, mannose, talose, heptose, glucose, fructose, methyl α-D-glucopyranoside, maltose, lactone, sorbose, erythrose, threose, arabinose, allose, altrose, gulose, idose, talose, erythrulose, ribulose, xylulose, psicose, tagatose, glucosamine, galactosamine, arabinans, fructans, fucans, galactans, galacturonans, glucans, mannans, xylans, inulin, levan, fucoidan, carrageenan, galactocarolose, pectins, amylose, pullulan, glycogen, amylopectin, cellulose, pustulan, chitin, agarose, keratin, chondroitin, dermatan, hyaluronic acid, xanthin gum, sucrose, trehalose, dextran, and lactose. Sugar alcohol bulking agents include, but are not limited to, alditols, inositols, sorbitol, and mannitol. Sugar acid bulking agents include, but are not limited to, aldonic acids, uronic acids, aldaric acids, gluconic acid, isoascorbic acid, ascorbic acid, glucaric acid, glucuronic acid, gluconic acid, glucaric acid, galacturonic acid, mannuronic acid, neuraminic acid, pectic acids, and alginic acid. Amino acid bulking agents include, but are not limited to, glycine, histidine, and proline.

In some embodiments, a surfactant may be included in the compositions. Surfactants, in general, reduce the surface tension of a liquid composition. This may provide beneficial properties such as improved ease of filtration. Surfactants also may act as emulsifying agents and/or solubilizing agents. Surfactants are well known in the art. Accordingly, the surfactants described herein are not intended to constitute an exhaustive list, but are provided merely as exemplary surfactants that may be used in the formulations or compositions of the present disclosure. Surfactants that may be included include, but are not limited to, sorbitan esters such as polysorbates (e.g., polysorbate 20 and polysorbate 80), lipopolysaccharides, polyethylene glycols (e.g., PEG 400 and PEG 3000), poloxamers (i.e., pluronics), ethylene oxides and polyethylene oxides (e.g., Triton X-100), saponins, phospholipids (e.g., lecithin), and combinations thereof.

In some embodiments, an encapsulating agent may be included in the compositions. Encapsulating agents can sequester molecules and help stabilize or solubilize them. Encapsulating agents are well known in the art. Accordingly, the encapsulating agents described herein are not intended to constitute an exhaustive list, but are provided merely as exemplary encapsulating agents that may be used in the compositions. Encapsulating agents that may be included in compositions include, but are not limited to α-cyclodextrins, β-cyclodextrins, 7-cyclodextrin and combinations thereof (e.g., α-cyclodextrin, dimethyl-α-cyclodextrin, hydroxyethyl-α-cyclodextrin, hydroxypropyl-α-cyclodextrin, trimethyl-α-cyclodextrin, β-cyclodextrin, dimethyl-β-cyclodextrin, hydroxyethyl-β-cyclodextrin, hydroxypropyl-β-cyclodextrin, trimethyl-β-cyclodextrin, γ-cyclodextrin, dimethyl-γ-cyclodextrin, hydroxyethyl-γ-cyclodextrin, hydroxypropyl-γ-cyclodextrin, trimethyl-γ-cyclodextrin, and combinations thereof.

In some embodiments, a tonicity-adjusting agent may be included in the compositions. The tonicity of a liquid composition is an important consideration when administering the composition to a patient, for example, by parenteral administration. Tonicity-adjusting agents, thus, may be used to help make a composition suitable for administration. Tonicity-adjusting agents are well known in the art. Accordingly, the tonicity-adjusting agents described herein are not intended to constitute an exhaustive list, but are provided merely as exemplary tonicity-adjusting agents that may be used in the compositions. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, dextrose and mannitol.

In some embodiments, a stabilizing agent may be included in the compositions. Stabilizing agents help increase the stability of a compound in the compositions. This may occur by, for example, reducing degradation or preventing aggregation of a compound. Without wishing to be bound by theory, mechanisms for enhancing stability may include sequestration of the compound from a solvent or inhibiting free radical oxidation of the therapeutically effective substance. Stabilizing agents are well known in the art. Accordingly, the stabilizing agents described herein are not intended to constitute an exhaustive list, but are provided merely as exemplary stabilizing agents that may be used in the compositions. Stabilizing agents may include, but are not limited to, emulsifiers and surfactants.

In some embodiments, a protectant may be included in the compositions. Protectants are agents that protect a pharmaceutically active ingredient (e.g., a therapeutically effective substance or compound) from an undesirable condition (e.g., instability caused by freezing or lyophilization, or oxidation). Protectants can include, for example, cryoprotectants, lyoprotectants, and antioxidants. Cryoprotectants are useful in preventing loss of potency of an active pharmaceutical ingredient (e.g., an anthracycline compound) when a composition is exposed to a temperature below its freezing point. For example, a cryoprotectant could be included in a reconstituted lyophilized formulation so that the formulation could be frozen before dilution for intravenous administration. Cryoprotectants are well known in the art. Accordingly, the cryoprotectants described herein are not intended to constitute an exhaustive list, but are provided merely as exemplary cryoprotectants that may be used in the compositions. Cryoprotectants include, but are not limited to, solvents, surfactants, encapsulating agents, stabilizing agents, viscosity modifiers, and combinations thereof. Cryoprotectants may include, for example, disaccharides (e.g., sucrose, lactose, maltose, and trehalose), polyols (e.g., glycerol, mannitol, sorbitol, and dulcitol), glycols (e.g., ethylene glycol, polyethylene glycol and propylene glycol).

Lyoprotectants are useful in stabilizing the components of a composition subjected to lyophilization. For example, a therapeutically effective substance could be lyophilized with a lyoprotectant prior to reconstitution. Lyoprotectants are well known in the art. Accordingly, the lyoprotectants described herein are not intended to constitute an exhaustive list, but are provided merely as exemplary lyoprotectants that may be used in the compositions. Lyoprotectants include, but are not limited to, solvents, surfactants, encapsulating agents, stabilizing agents, viscosity modifiers, and combinations thereof. Exemplary lyoprotectants may be, for example, sugars and polyols. Trehalose, sucrose, dextran, and hydroxypropyl-beta-cyclodextrin are non-limiting examples of lyoprotectants.

Antioxidants are useful in preventing oxidation of the components of a composition. Oxidation may result in aggregation of a drug product or other detrimental effects to the purity of the drug product or its potency. Antioxidants are well known in the art. Accordingly, the antioxidants described herein are not intended to constitute an exhaustive list, but are provided merely as exemplary antioxidants that may be used in the compositions. Antioxidants may be, for example, sodium ascorbate, citrate, thiols, metabisulfite, and combinations thereof.

In some embodiments, a viscosity modifying agent may be included in the composition. Viscosity modifiers change the viscosity of liquid compositions. This may be beneficial because viscosity plays an important role in the ease with which a liquid composition is filtered. A composition may be filtered prior to lyophilization and reconstitution, or after reconstitution. Viscosity modifiers are well known in the art. Accordingly, the viscosity modifiers described herein are not intended to constitute an exhaustive list, but are provided merely as exemplary viscosity modifiers that may be used in the compositions. Viscosity modifiers include solvents, solubilizing agents, surfactants, and encapsulating agents.

Exemplary viscosity modifiers that may be included in compositions include, but are not limited to, N-acetyl-DL-tryptophan and N-acetyl-cysteine.

Antitumor Activity in Human Tumor Xenograft Mice Models

The albumin-binding prodrugs AE-Keto-Sulf07 and AE-Ester-Sulf07 demonstrated exceptional antitumor activity in tumor cell lines, with $IC_{50}$ of the free drugs AE-Keto and AE-Ester in the picomolar range (259 and 339 pM, respectively, comparable to the $IC_{50}$ of 130 pM of the parent compound AE—see Example 4) as well as in in several human tumor xenograft models in nude mice inducing partial and complete remissions in all human tumor xenograft evaluated (see examples in FIGS. 13-23). This included small tumors with starting volumes in the range of approximately 130-170 mm$^3$ and also large tumors with starting volumes of up to approximately 380 mm$^3$. Furthermore, in most cases therapy with the albumin-binding prodrugs AE-Keto-Sulf07 and AE-Ester-Sulf07 induced long-term remissions and a decrease in Relative Tumor Volume (RTV). The parent compound auristatin E (AE) was principally inactive in the tested models or only showed marginal tumor inhibition. Experimental procedures and the results in the tumor-bearing mice models are described in detail in Example 5 and FIGS. 13-23.

Methods of Treatment

The compounds and compositions described herein are useful for a variety of clinical applications.

The compounds and compositions described herein can induce prolonged or long-term inhibition of tumor growth. In certain embodiments, the prolonged or long-term inhibition of tumor growth is without any loss in body weight or any or merely marginal bone marrow toxicity.

In some embodiments, the present disclosure provides a method for treating a malignant disease comprising administering to a patient in need thereof a therapeutically effective amount of a pharmaceutical composition containing a compound described herein. For example, some embodiments include a method for treating a patient suffering from a disease selected from a cancer, a virus disease, autoimmune disease, acute or chronic inflammatory disease, and a disease caused by bacteria, fungi, and other micro-organisms, comprising administering to the patient in need thereof a therapeutically effective amount of a compound according to the present disclosure.

The disclosure provides for methods of treating a condition or disease in a patient, said condition or disease selected from a cancer, a virus disease, autoimmune disease, acute or chronic inflammatory disease, and a disease caused by bacteria, fungi, or other micro-organisms, comprising administering to the patient a compound or a pharmaceutical composition as described herein.

In some embodiments, the cancer is a blood cancer or a solid tumor cancer. In some embodiments, the cancer is selected from carcinoma, sarcoma, leukemia, lymphoma, multiple myeloma, or melanoma.

In some embodiments, the cancer is adenocarcinoma, uveal melanoma, acute leukemia, acoustic neuroma, ampullary carcinoma, anal carcinoma, astrocytoma's, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinomas, uterine cancer, cervical cancer, neck, nose and ear tumors, hematological neoplasia's, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, colon cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer, ovary carcinoma or lymph gland cancer.

Some embodiments include a method of increasing the concentration of a metabolite of a compound in a tumor, comprising administering the compound according to the present disclosure.

Variations and Modifications

Variations, modifications, and other implementations of what is described herein will occur to those of ordinary skill without departing from the spirit and the scope of the present disclosure. Accordingly, the present disclosure is not to be limited to the preceding description or the following examples.

Exemplification

With aspects of the present disclosure now being generally described, these will be more readily understood by reference to the following examples, which are included merely for purposes of illustration of certain features and embodiments of the present disclosure and are not intended to be limiting.

Equivalents

Those skilled in the art will recognize, or be able to ascertain using no more than routine experimentation, numerous equivalents to the compounds, compositions, and methods of use thereof described herein. Such equivalents are considered to be within the scope of the present disclosure.

EXAMPLES

Materials and Methods for Preparation and Analysis of Compounds

All reactions were carried out under nitrogen inert atmosphere, unless otherwise stated. Commercially available reagents were used without further purification, unless otherwise stated. The anhydrous solvents were purchased in anhydrous form (dichloromethane, dimethylsulfoxide, N,N-dimethylformamide, tetrahydrofuran, etc.) and all other solvents used were reagent grade or HPLC or LCMS grade.

Glassware and stir bars were generally dried in an oven at 110° C. for at least 12 h and then cooled under nitrogen atmosphere prior to use, where applicable. All other reactions were performed in round-bottom flasks sealed with rubber septa. Plastic syringes or glass pipets were used to transfer liquid reagents. Reactions were stirred magnetically using teflon-coated, magnetic stir bars. Organic solutions were concentrated under reduced pressure using a rotary evaporator KNF RC 600 and Heidolph Hei-VAP.

Flash column chromatography was performed with pre-packed Biotage® SNAP Ultra and SNAP Ultra C18 flash silica gel cartridges, using Biotage® Isolera™ One and Biotage® Isolera™ SL (big scale) flash purification systems.

The pH value of a solution was measured at room temperature using a pH meter WTW Inolab 7310 with SenTix® mic-D electrodes.

High-performance liquid chromatography (HPLC) was performed using a Shimadzu Nexera XR HPLC system equipped with a SPD-M20A photodiode array detector and it was monitored at 220 nm, unless otherwise stated.

Low-resolution mass spectra (LRMS) were collected using liquid chromatography combined with mass spectrometry (LCMS) on a Bruker Amazon SL or Thermo Fisher LCQ advantage spectrometers (electrospray ionization, ESI). High-resolution mass spectra (HRMS) were recorded on a micrOTOF instrument from Bruker using a liquid chromatography-electrospray ionization and time-of-flight mass spectrometer (ESI-TOF). Elemental analyses were carried out on a Leco TruSpec® CHNS Macro with an IR-detector for C, H, and S; and with a thermal conductivity detector (TCD) for N.

Lyophilization was carried out using a Martin Christ Alpha or Epsilon 2-4 LSCplus freeze drier.

Centrifugation was carried out using Eppendorf centrifuge 5810 R, refrigerated, with Rotor A-4-81, 230 V/50-60 Hz.

Trifluoroacetic acid (TFA) content was measured using ion chromatography and water content was measured using Karl Fischer (KF) coulometry.

Nuclear magnetic resonance (NMR) spectra were recorded at ambient temperature on 400 MHz spectrometer: Bruker Avance 400 Ultrashield (400 MHz in $^1$H, 100 MHz in $^{13}$C). All values for proton chemical shifts are reported in parts per million ($\delta$) and are referenced to the deuterated protons in DMSO-$d_6$ ($\delta$ 2.50). All values for carbon chemical shifts are reported in parts per million ($\delta$) and are referenced to the carbon resonances in DMSO-$d_6$ ($\delta$ 39.52). NMR data are represented as follows: chemical shift, multiplicity (s=singlet, d=doublet, t=triplet, q=quartet, p=pentet, m=multiplet, br=broad, dd=doublet of doublets, td=triplet of doublets), coupling constant=J (Hz=Hertz), and integration.

HPLC Methods

Method 1: HPLC method for linker intermediates and final product Sulf07 purity. Column: Phenomenex Kinetex Polar C18 (150×4.6 mm, 2.6 μm, 100 Å), gradient: mobile phase A: 95:5 ammonium acetate 10 mM pH 7.0: acetonitrile, mobile phase B: 95:5, acetonitrile: ammonium acetate 10 mM pH 7.0. Elution gradient of phase B: 0-2.5 min: 0%, 2.5-18 min: 0-45%, 18-20 min: 45-75%, 20-24 min: 75%, 24-26 min: 75%-0%, 26-30 min: 0%, 30 minutes: method end, flow rate=1.0 mL/min.

Method 2: HPLC method for Example 2 and Example 3. Column: Phenomenex Kinetex Polar C18 (150×4.6 mm, 2.6 μm, 100 Å), gradient: mobile phase A: 95:5 ammonium acetate 10 mM pH 7.0: acetonitrile, mobile phase B: 95:5, acetonitrile: ammonium acetate 10 mM pH 7.0. Elution gradient of phase B: 0-0.5 min: 30%, 0.5-9 min: 30-95%, 9-11 min: 95%, 11-12.5 min: 95-30%, 12.5-15 min: 30%, 15 minutes: method end, flow rate=1.0 mL/min.

Method 3: LCMS method for linker intermediates and final product Sulf07. Column: Phenomenex Kinetex Polar C18 (150×2.1 mm, 2.6 μm, 100 Å), gradient: mobile phase A: 95:5 ammonium acetate 10 mM pH 7.0: acetonitrile, mobile phase B: 95:5, acetonitrile: ammonium acetate 10 mM pH 7.0. Elution gradient of phase B: 0-2.5 min: 0%, 2.5-18 min: 0-45%, 18-20 min: 45-75%, 20-24 min: 75%, 24-26 min: 75%-0%, 26-30 min: 0%, 30 minutes: method end. Flow rate=0.4 mL/min.

Method 4: LCMS method for Example 2 and Example 3. Column: Phenomenex Luna Omega Polar C18 (50×2.1 mm, 1.6 μm, 100 Å), gradient: mobile phase A: 99.9:0.1 water: formic acid, mobile phase B: 99.9:0.1 acetonitrile: formic acid. Elution gradient of phase B: 0-0.5 min: 20%, 0.5-3.5 min: 20-100%, 3.5-5.0 min: 100%, 5.0-5.5 min: 100-20%, 5.5-7.0 min: 20%, 7 minutes: method end. Flow rate=0.4 mL/min.

Method 5: LCMS method for plasma binding experiments. Column: Phenomenex Kinetex Polar C18 (50×2.1 mm, 2.6 μm, 100 Å), gradient: mobile phase A: 95:5 ammonium acetate 10 mM pH 7.0: acetonitrile, mobile phase B: 95:5, acetonitrile: ammonium acetate 10 mM pH 7.0. Elution gradient of phase B: 0-1.0 min: 0%, 1.0-7.0 min: 0-75%, 7.0-7.5 min: 75-90%, 7.5-8.5 min: 90-0%, 8.5-10.0 min: 0%, 10 minutes: method end, flow rate=0.4 mL/min.

Method 6: Hydrophobic interaction chromatography (HIC) method for plasma binding. Column: MabPac HIC-20 (250×4.6 mm, 5 μm, 100 Å), gradient: mobile phase A: 1.5 M $(NH_4)_2SO_4$, 20 mM $Na_2HPO_4$ pH 8.0, mobile phase B: 20 mM $Na_2HPO_4$ pH 8.0 and 20% isopropanol. Elution gradient of phase B: 0-2.0 min: 0%, 2.0-10.0 min: 0-50%, 10.0-13.0 min: 50-60%, 13.0-17.0 min: 60-100%, 17.0-20.0 min: 100%, 20.0-25.0 min: 100-0%, 25.0-30.0 min: 0%, 30 minutes: method end, flow rate=1 mL/min.

Method 7: HPLC method for albumin drug conjugate pH stability profile. Column: Phenomenex Aeris WP C18 (250× 4.6 mm, 3.6 μm, widepore), gradient: mobile phase A: 20 mM Tris buffer pH 8.0, mobile phase B: 90% acetonitrile UHPLC and 10% water. Elution gradient of phase B: 0-0.5 min: 25%, 0.5-2.5 min: 25-35%, 2.5-16.0 min: 35-85%, 16.0-17.0 min: 85-95%, 17.0-20.0 min: 95%, 20.0-25.0 min: 95-25%, 25.0-30.0 min: 25%, 30 minutes: method end, flow rate=1.0 mL/min.

Method 8: HPLC method for accelerated degradation of API's formulations. Column: Phenomenex Kinetex Polar C18 (150×4.6 mm, 2.6 μm, 100 Å), gradient: mobile phase A: 95:5 ammonium acetate 10 mM pH 7.0: acetonitrile, mobile phase B: 95:5, acetonitrile: ammonium acetate 10 mM pH 7.0. Elution gradient of phase B: 0-2.5 min: 20%, 0.5-9 min: 20-75%, 9-11 min: 75%, 11-12.5 min: 75-20%, 12.5-15 min: 20%, 15 minutes: method end, flow rate=1.0 mL/min.

Method 9: HPLC method for linker intermediates and final product Sulf07 purity prepared according to route C. Column: Phenomenex Kinetex Polar C18 (150×4.6 mm, 2.6 μm, 100 Å), gradient: mobile phase A: 0.1% trifluoroacetic acid in $H_2O$, mobile phase B: 0.1% trifluoroacetic acid in acetonitrile. Elution gradient of phase B: 0-5.5 min: 1%, 5.5-20 min: 1-40%, 20-22 min: 40-65%, 22-24 min: 65%, 24-27 min: 65/0-1%, 27-30 min: 1%, 30 minutes: method end, flow rate=1.0 mL/min.

Method 10: HPLC method for the purity of AE-Keto-Sulf07 prepared from linker Sulf07 obtained according to route C. Kinetex Polar C18 column (2.6 μm, 100 Å, 150 mm×4.6 mm), gradient: mobile phase A: 95:5 ammonium acetate 5 mM pH 7.0: methanol, mobile phase B: 95:5 methanol: ammonium acetate 5 mM pH 7.0. Elution gradient of phase B: 0-2.5 min: 60%, 2.5-18 min: 60-80%, 18-22 min: 80-95%, 22-26 min: 95%, 26-30 min: method end. Flow rate=1.0 mL/min. Column Oven: 37° C.

Example 1

Sulf07, 5-(6-(2,5-dioxo-2,5-dihydro-1H-pyrrol-1-yl) hexanamido)-2-(hydrazine-carbonyl)-benzenesulfonic acid), was prepared as described below and shown in Scheme 1 according to Route A.

Scheme 1, Route A

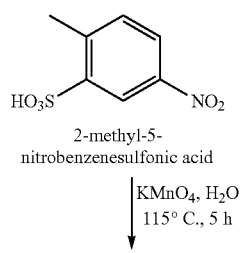

2-methyl-5-nitrobenzenesulfonic acid

| $KMnO_4$, $H_2O$
| 115° C., 5 h

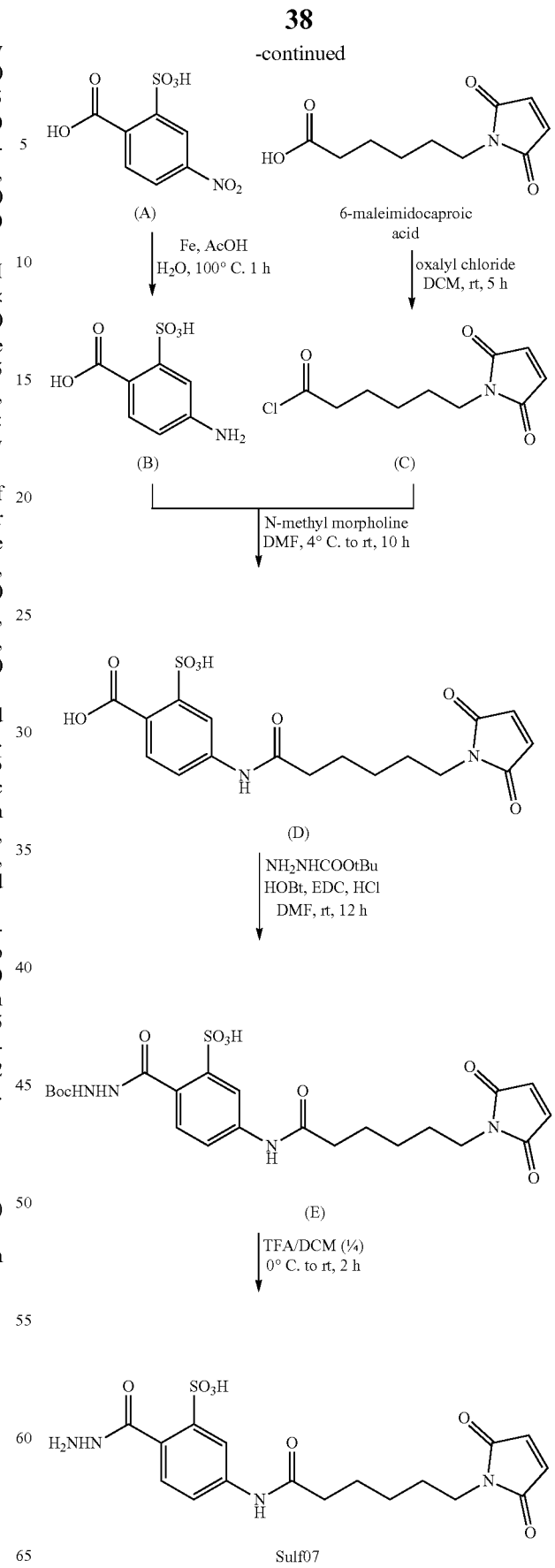

Synthesis of 4-nitro-2-sulfobenzoic Acid (A)

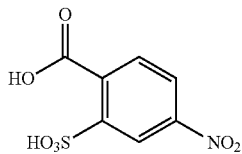 [SMILES: O=C(O)c1ccc([N+](=O)[O-])cc1S(=O)(=O)O]

To a stirred solution of potassium permanganate (72 g, 460 mmol, 4.5 equiv., Sigma Aldrich) in Millipore water (450 mL) was added within 10 seconds a solution of 4-nitro-2-sulfonic acid hydrate (26 g, 102 mmol, 1.0 equiv., Abcr) in Millipore water (100 mL). The resulting purple mixture was stirred at 115° C. for 5 h which turned brown after this time. HPLC (method 1, 220 nm) confirmed that the reaction was complete after 5 h. The reaction mixture was cooled down to room temperature. The brown solid formed during the reaction was removed through suction filtration on a Celite pad, washed with Millipore water (300 mL) and the brown/yellow filtrate solution was concentrated to ~125 mL under reduced pressure at 40° C., acidified slowly with 5 M HCl solution until a white suspension was formed (~pH 1). The white suspension was then heated at 100° C. until a clear solution was obtained which was left to stand in an ice bath for 10 min until a white solid formed. The white solid was obtained by suction filtration using a fritted filter (pore size 4). The white solid was then dried under high vacuum for 10 h to give A. Yield: 18 g, 72%. Purity by HPLC (method 1, 220 nm)>95%. LRMS-ESI (m/z) calcd. for $C_7H_4NO_7S$ [M–H]$^-$: 245.98. Found: 245.83.

Synthesis of 4-amino-2-sulfobenzoic Acid (B)

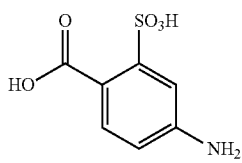

A stirred suspension of 4-nitro-2-sulfobenzoic acid A (13 g, 51 mmol, 1.0 equiv.) in Millipore water (75 mL) was heated at reflux (120° C.) until complete dissolution. At that temperature was added acetic acid (7.2 mL, Sigma Aldrich), followed by iron powder (9.5 g, 180 mmol, 3.5 equiv., Sigma Aldrich) that was added portion-wise (~1 g/1.0 min) over 10 min to avoid an exothermic reaction. The reaction mixture was then left stirring under reflux for 1 h. During this time, a brown solid formed and HPLC analysis (method 1, 220 nm) confirmed that the reaction was complete. The brown solid was removed by suction filtration directly on a Celite pad (when still hot) and was further washed with hot water (3×50 mL). The filtrate was then filtered through Whatman filter paper (11 µm). The resulting filtrate was concentrated under reduced pressure at 50° C. to a volume of ~100 mL. Concentrated HCl was added dropwise (~1 mL/2.0 min) until pH 1 was reached, and a white/yellow solid precipitated. The suspension was left at 4° C. for 1 h. The solid was collected by suction filtration using a fritted filter (pore size 4) and was dried under high vacuum for 10 h to afford B as a white solid. Yield: 9 g, 81%. Purity by HPLC (method 1, 220 nm)>95%. LRMS-ESI (m/z) calcd. for $C_7H_4NO_5S$ [M–H]$^-$: 216.00. Found: 216.16.

Synthesis of 6-(2,5-dioxo-2,5-dihydro-1H-pyrrol-1-yl)hexanoyl Chloride or EMC-Cl (C)

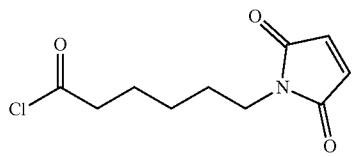 [SMILES: O=C(Cl)CCCCCN1C(=O)C=CC1=O]

To a stirring solution of 6-maleimidocaproic acid (EMC) (33 g, 156 mmol, 1.0 equiv., Alfa Aesar) in dry dichloromethane (150 mL) at room temperature and under nitrogen atmosphere was added within 30 min (~1 mL/2 min) oxalyl chloride (15 mL, 171 mmol, 1.1 equiv., Sigma Aldrich) using a dropping funnel. Caution: Gas evolution was observed during the addition process. The reaction was stirred at room temperature for 5 h. The color of the reaction solution changed to dark yellow during the reaction time and HPLC analysis (method 1, 220 nm) confirmed that the reaction was completed after 5 h. The solvent was removed under reduced pressure at 40° C. to give an oil that was dried under high vacuum overnight resulting in a solidified compound. The obtained light brownish solid was crushed with a spatula and dried for further 20 h under high vacuum to give C as a yellow microcrystalline solid. The compound was used in the next reaction without further purification. Yield: 34 g, 95%. Purity by HPLC (method 1, 220 nm)>95% as the methyl ester. LRMS-ESI (m/z) calcd. for $C_{11}H_{16}NO_4$ (as methyl ester) [M+H]$^+$: 226.10. Found: 225.97.

Synthesis of 4-(6-(2,5-dioxo-2,5-dihydro-1H-pyrrol-1-yl)hexanamido)-2-sulfobenzoic Acid (D)

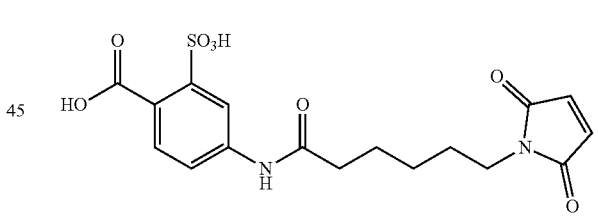

B (18.5 g, 85 mmol, 1.0 equiv.) was dissolved in anhydrous N,N-dimethylformamide (300 mL) under nitrogen atmosphere. The solution was cooled down with an ice-bath, and left stirring for 10 min to reach 4° C. Then, 4-methylmorpholine (18.69 mL, 170 mmol, 2.0 equiv., Sigma Aldrich) was added to the cooled solution dropwise (~1 mL/3.5 min) within 1 h using a dropping funnel. The mixture became dark-brown when addition was completed, and to this dark-brown mixture was added drop wise (~0.5 g/min) within 1 h using a dropping funnel a solution of C (29.28 g, 127 mmol, 1.5 equiv.) in anhydrous N,N-dimethylformamide (200 mL). The reaction mixture was let to warm up gradually to room temperature overnight and then allowed to stir at room temperature for 10 h. After full conversion of the reaction as indicated by HPLC (method 1, 220 nm), the reaction solution was dispensed in 8×50 mL Falcon tubes and was centrifuged for 20 minutes at 10° C.

and 4.000 rpm. The supernatants were removed, and the solids were re-suspended in 10 mL of N,N-dimethylformamide per each tube and centrifuged again for 20 min at 10° C. and 4.000 rpm. All the supernatants were combined and concentrated under reduced pressure at 50° C. for 3 h to obtain a light orange solid (Yield: 34 g, purity by HPLC (method 1, 220 nm) 66%). This solid was re-suspended in methanol (250 mL), transferred to 8×50 mL Falcon tubes, and centrifuged for 20 minutes at 10° C. and 4.000 rpm. The supernatants were removed, and the solids were re-suspended in 5 mL of methanol per each tube and centrifuged again for 20 min at 10° C. and 4.000 rpm. All the solids were combined and dried under high vacuum for 24 h to obtain D as a crystalline yellow solid. Yield: 24 g, 37%. Purity by HPLC (method 1, 220 nm) 97%. LRMS-ESI (m/z) calcd. for $C_{17}H_{17}N_2O_8S$ [M−H]⁻: 409.08. Found: 409.13.

Synthesis of 2-(2-(tert-butoxycarbonyl)hydrazine-1-carbonyl)-5-(6-(2,5-dioxo-2,5-dihydro-1H-pyrrol-1-yl)hexanamido)benzenesulfonic Acid or BOC-Protected Linker (E)

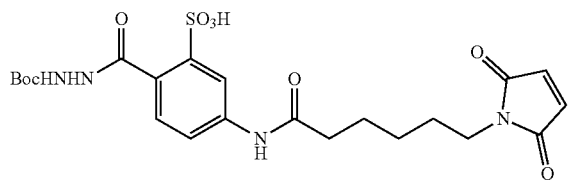

To a solution of D (17 g, 41.4 mmol, 1.0 equiv.) in anhydrous N—N-dimethylformamide (350 mL) under nitrogen atmosphere were added N-(3-dimethylaminopropyl)-N'-ethylcarbodiimide-hydrochloride (EDC-HCl) (8.72 g, 45.5 mmol, 1.1 equiv., Roth) and hydroxybenzotriazole (HOBt) (6.15 g, 45.5 mmol, 1.1 equiv., Sigma Aldrich). The reaction mixture was left to stir 30 min at room temperature, and then tert-butyl carbazate (7.12 g, 53.9 mmol, 1.3 equiv., Sigma Aldrich) was added and the solution turned from clear yellow to a reddish color. The reaction mixture was stirred at room temperature overnight. After this time, full conversion of the reaction was confirmed by HPLC (method 1, 220 nm). The solvent was removed under reduced pressure at 40° C. and then under high vacuum at rt for 1 h, to afford a purple-brown oil which was purified with flash purification system with two pre-packed SNAP Ultra 340 g cartridges. The purification was carried out using a linear gradient system, from 100% dichloromethane to 90%/10% dichloromethane/methanol in 60 column volumes. The tubes containing the desired product were combined and dried under reduced pressure at 40° C. for 1 h and under high vacuum for another 6 h to obtain E as a foamy yellow solid. Yield: 9 g, 17.1 mmol, 42%. HPLC (method 1, 220 nm)>95%. LRMS-ESI (m/z) calcd. for $C_{22}H_{27}N_4O_9S$ [M−H]⁻: 523.16. Found: 523.15.

Synthesis of linker Sulf07, 5-(6-(2,5-dioxo-2,5-dihydro-1H-pyrrol-1-yl)hexanamido)-2-(hydrazinecarbonyl)benzenesulfonic Acid

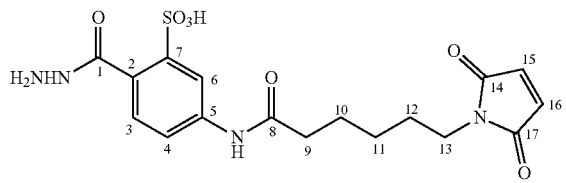

To a yellow solution of E (10.2 g, 19.4 mmol, 1.0 equiv.) in anhydrous dichloromethane (30 mL), which was cooled down to 4-5° C., was added dropwise (~1 mL/2.0 min), within 30 min, trifluoroacetic acid (15 mL, Roth). After the addition the cold bath was removed and the reaction mixture was left to stir at room temperature for 3 h. After this time, completion of the reaction was confirmed by HPLC (method 1, 220 nm). The reaction mixture was poured dropwise in 6 Falcon tubes, each containing ~35 mL cold diethyl ether. A white precipitate formed immediately. The tubes were left to stand at 4° C. for 3 h. After centrifugation of the Falcon tubes for 20 minutes at 10° C. and 4000 rpm, the supernatants were removed, and the solids were re-suspended in 5 mL of diethyl ether per each tube and centrifuged again (4000 rpm, 20 min, 10° C.). The supernatants were removed again and the solids were collected and dried under high vacuum for 20 h to afford the linker Sulf07 as a white microcrystalline solid. Yield: 10 g, 23.6 mmol, 96%. HPLC (method 1, 220 nm)>95%. LRMS-ESI (m/z) calcd. for $C_{17}H_{21}N_4O_7S$ [M+H]⁺: 425.11. Found: 425.07. LRMS-ESI (m/z) calcd. for $C_{17}H_{19}N_4O_7S$ [M−H]⁻: 423.11. Found: 423.12. HRMS-ESI (m/z) calcd. for $C_{17}H_{21}N_4O_7S$ [M+H]⁺: 425.1125. Found: 425.1125. LRMS-ESI (m/z) calcd. for $C_{17}H_{19}N_4O_7S$ [M−H]⁻: 423.0978. Found: 423.0980.

The structure for, 5-6-(2,5-dioxo-2,5-dihydro-1H-pyrrol-1-yl)hexanamido)-2-(hydrazine-carbonyl)benzenesulfonic acid, Sulf07, was confirmed by 1H NMR: $^1$H NMR (400 MHz, DMSO-$d_6$) δ 11.94 (s, 1H; C1-NH), 10.27 (s, 1H; C8-NH), 8.01 (d, J=2.2 Hz, 1H; $C_4$—CH), 7.93 (dd, J=8.5, 2.2 Hz, 1H; C6-CH), 7.68 (d, J=8.4 Hz, 1H; C7-CH), 7.00 (s, 2H; C15-CH, C16-CH), 3.40 (t, J=7.0 Hz, 2H; C13-CH$_2$), 2.32 (t, J=7.4 Hz, 2H; C9-CH$_2$), 1.60 (p, J=7.5 Hz, 2H; C10-CH$_2$), 1.52 (p, J=7.2 Hz, 2H; C12-CH$_2$), 1.26 (q, J=8.8 Hz, 2H; C11-CH$_2$); $^{13}$C NMR (101 MHz, DMSO-$d_6$) δ 172.20 (C8), 171.54 (C14, C17), 167.59 (C1), 145.73 (C5), 142.09 (C3), 134.90 (C15, C16), 132.09 (C7), 123.79 (C2), 119.44 (C6), 117.47 (C4), 37.42 (C13), 36.65 (C9), 28.22 (C12), 26.21 (C11), 24.90 (C10). Elemental analysis calcd. for $C_{17}H_{21}N_4O_7S$; C, 45.71; H, 4.26; N, 11.85; S, 6.78. Found: C, 46.2917; H, 4.4836; N, 12.8879; S, 6.7886. TFA content <2% (w/w).

Sulf07, 5-(6-(2,5-dioxo-2,5-dihydro-1H-pyrrol-1-yl) hexanamido)-2-(hydrazine-carbonyl)benzenesulfonic acid, was prepared as described below and shown in Scheme 2 according to Route B.

Scheme 2, Route B

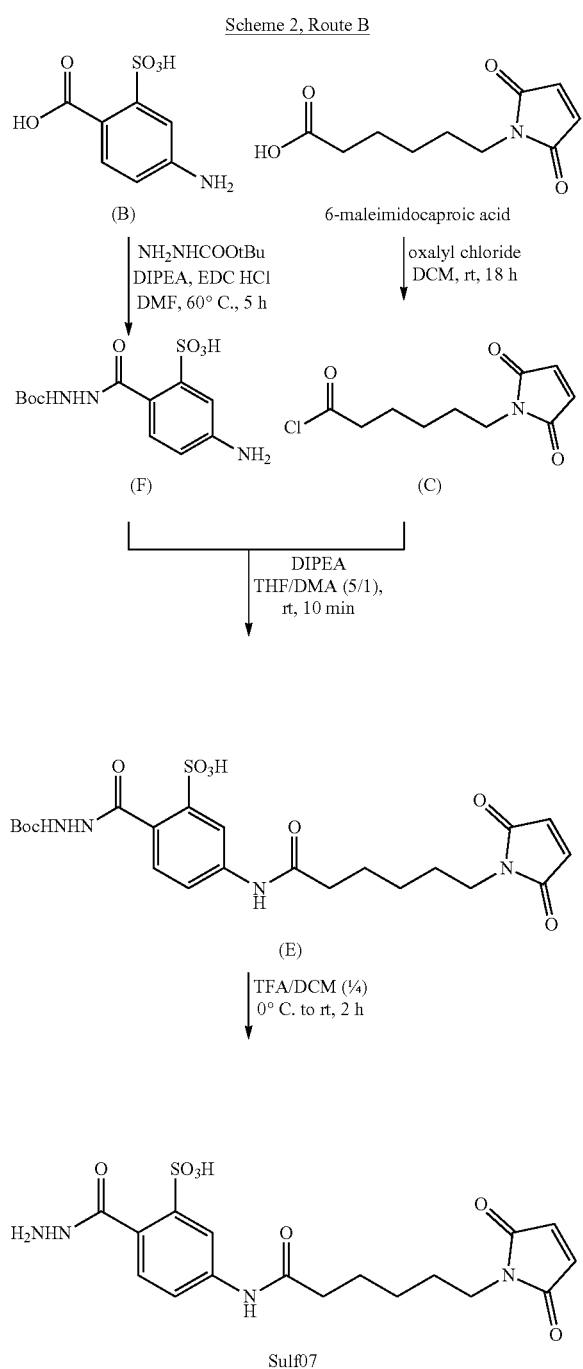

To a suspension of 4-amino-2-sulfobenzoic acid B (50.00 g, 230.20 mmol, 1.00 equiv.) in anhydrous N,N-dimethylformamide (DMF, 1000 mL) was added N, N-diisopropylethylamine (DIPEA, 40.20 mL, 29.75 g, 230.20 mmol, 1.00 equiv.) over 5 minutes. EDC-HCl (48.54 mg, 253.21 mmol, 1.10 equiv.) was then added and the mixture stirred at 23° C. for 30 min. tert-Butyl carbazate (33.46 g, 253.18 mmol, 1.10 equiv.) was then added and the mixture was heated to 70° C. and stirred for 2 h. The second portion of EDC-HCl (24.31 g, 126.68 mmol, 0.55 equiv.) and tert-butyl carbazate (16.76 mg, 126.68 mmol, 0.55 equiv.) was added and the reaction mixture was further stirred at 70° C. for 14 h. The reaction was cooled to 23° C. and filtered through Celite® 545 (100 g). Celite® 545 was additionally washed with 700 mL of methanol. The filtrate was concentrated under reduced pressure and purified by flash purification system using seven pre-packed SNAP Ultra 340 g cartridges. The purification was carried our using a linear gradient system, from 100% dichloromethane to 70% dichloromethane/30% methanol to give the title compound F as a white solid. Yield: 32.50 g, 98.09 mmol, 42.6%, HPLC (method 1, 220 nm)>97%. LRMS-ESI (m/z) calcd. for $C_{12}H_{16}N_3O_6S$ $[M-H]^-$: 330.08. Found: 330.17.

Synthesis of N-ethyl-N-isopropylpropan-2-aminium 2-(2-(tert-butoxy-carbonyl)hydrazine-1-carbonyl)-5-(6-(2,5-dioxo-2,5-dihydro-1H-pyrrol-1-)hexanamido)benzenesulfonate (E)

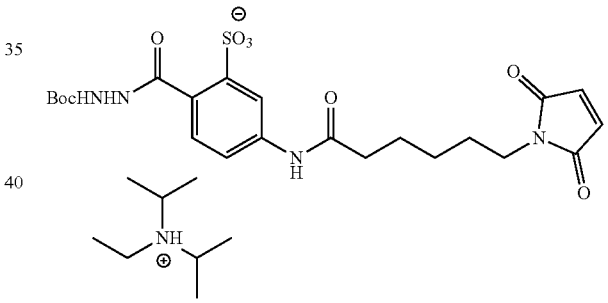

To a solution of F (26.97 g, 81.40 mmol, 1.00 equiv.) in a mixture of anhydrous dimethylacetamide (110 mL) and anhydrous tetrahydrofuran (THF, 275 mL) was added a solution of 6-maleimidocaproic acid chloride C (26.60 g, 115.82 mmol, 1.42 equiv.) in anhydrous tetrahydrofuran (165 mL) in one portion at room temperature. The clear reaction solution was stirred at room temperature for 10 min. The reaction mixture was then added upon stirring into two 2 L conical flasks, each containing diisopropyl ether (1100 mL) and DIPEA (10.15 mL). Once the oil had settled, the supernatant was carefully poured off and the oil was washed with diisopropyl ether (2×100 mL), dissolved in methanol, combined and the solvent was removed under high vacuum. The resulted oil was purified by flash purification system using six pre-packed SNAP Ultra 340 g cartridges. The purification was carried our using a linear gradient system, from 100% dichloromethane to 80% dichloromethane/20% methanol to give the title compound E as a white solid. Yield: 24.00 g, 36.71 mmol, 45.1%, HPLC (method 1, 220 nm)>95%. LRMS-ESI (m/z) calcd. for $C_{22}H_{27}N_4O_9S$ $[M-H]^-$: 523.15. Found: 523.30.

Synthesis of 5-(6-(2,5-dioxo-2,5-dihydro-1H-pyrrol-1-yl)hexanamido)-2-(hydrazine-carbonyl)benzenesulfonic Acid (Sulf07)

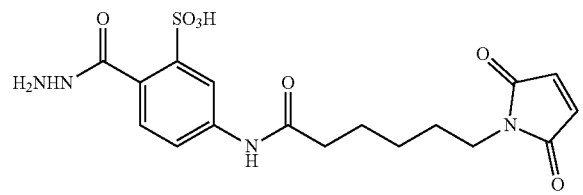

To a cold solution (4° C.) of E, (21.00 g, 32.12 mmol, 1.00 equiv.) in dichloromethane (150 mL) was added trifluoroacetic acid (25.00 mL, 37.25 g, 326.70 mmol, 10.17 equiv.) over 1 h. The reaction was then allowed to warm gradually (over 30 min) to room temperature and stirred for 1 h. The reaction mixture was added dropwise via a separating funnel over 1 h to a 2 L conical flask containing diisopropyl ether (1.4 L) at 0° C. The resulted white solid was filtered through a 4 Å porosity fritted funnel and washed sequentially with dichloromethane (2×1000 mL) and diisopropyl ether (2×1000 mL). The solid was left to dry on the fritted funnel overnight at room temperature. Further drying was carried out on high vacuum at 25° C. for 2 h. The final product Sulf07 was obtained as a white solid. Yield: 13.58 g, 32.00 mmol, 99.6%, HPLC (method 1, 220 nm)>96%. LRMS-ESI (m/z) calcd. for $C_{17}H_{19}N_4O_7S$ [M–H]$^-$: 423.10. Found: 423.21.

Sulf07, 5-(6-(2,5-dioxo-2,5-dihydro-1H-pyrrol-1-yl)hexanamido)-2-(hydrazine-carbonyl)benzenesulfonic acid, was prepared as described below and shown in Scheme 2 according to Route C.

Scheme 2, Route C

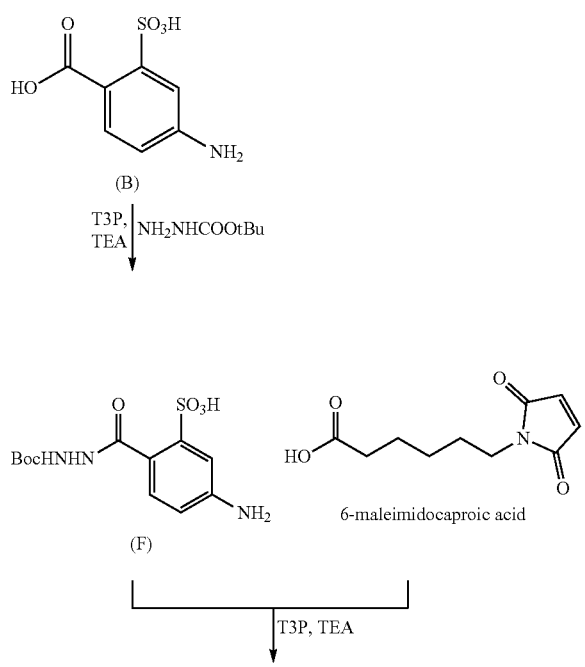

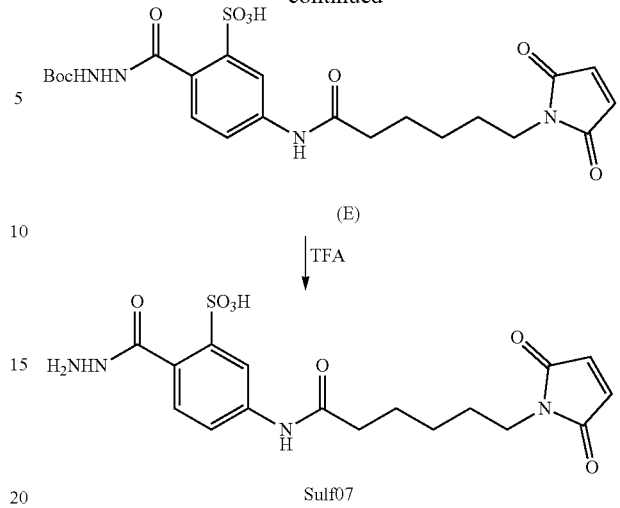

Synthesis of 5-amino-2-(2-(tert-butoxycarbonyl)hydrazine-1-carbonyl)benzenesulfonic Acid (F)

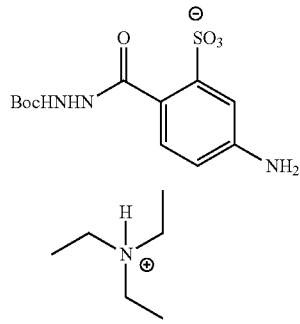

To a suspension of B (30.00 g, 138.12 mmol, 1.00 equiv.) in anhydrous acetonitrile (600 mL) was added triethylamine (41.93 g, 57.76 mL, 414.37 mmol, 3.00 equiv.) and the mixture was stirred for 10 min. Afterwards, tert-butyl carbazate (27.38 g, 207.19 mmol, 1.50 equiv.) was added and the mixture was cooled to −35° C. At this temperature, propylphosphonic anhydride solution, T3P, (114.27 g, 106.79 mL, 179.56 mmol, 50% sol. in ethyl acetate, 1.3 equiv.) was added dropwise over 1 h. The reaction was stirred at −35° C. for 2 h. The mixture was allowed to warm up to room temperature and filtered through Celite® 545 (100 g). Celite® was additionally washed with acetonitrile (500 mL). Both filtrates were combined and concentrated to 250 mL. The solution was split equally into 6 portions and the solvent was removed under reduced pressure. Each portion was dissolved in dichloromethane containing 1% Et$_3$N (50 mL) and purified by NP flash chromatography on a Biotage Isolera™ One Flash Purification System, with a pre-packed SNAP Ultra 340 g column, using a step gradient from 2% to 12% methanol (containing 1% NEt$_3$) in DCM (containing 1% NEt$_3$) over 7 column volumes. Then, the purified fractions from all portions were combined, the solvent was removed under reduced pressure and the solid was dried under high vacuum to give title compound F as an off-white solid. Yield: 53.25 g, 108.0 mmol, 78.2% (NMR in DMSO-d6 showed the presence of 1.6 eq. triethylamine). HPLC (method 9, 220 nm)>99%. LRMS-ESI (m/z) calcd. for $C_{12}H_{16}N_3O_6S$ [M−H]⁻: 330.08. Found: 330.08.

Synthesis of N-ethyl-N-isopropylpropan-2-aminium 2-(2-(tert-butoxy-carbonyl)hydrazine-1-carbonyl)-5-(6-(2,5-dioxo-2,5-dihydro-1H-pyrrol-1-)hexanamido)benzenesulfonate (E)

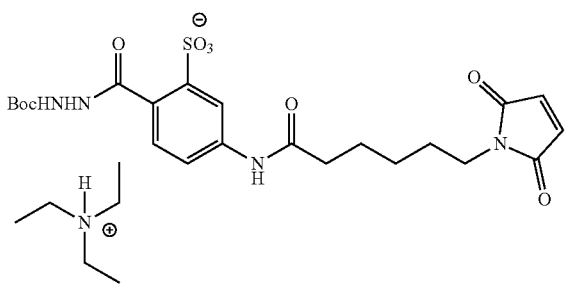

To a mixture of F (45.00 g, 91.24 mmol, 1.00 equiv.) and 6-maleimidocaproic acid (19.27 g, 91.24 mmol, 1.00 equiv.) was added, acetonitrile (450 mL), triethylamine (13.85 g, 19.08 mL, 136.86 mmol) and T3P (43.55 g, 40.70 mL, 136.86 mmol, 50% sol. in ethyl acetate) were added in one portion at room temperature. The solution was stirred at room temperature for 24 h. The solvent was removed under reduced pressure. The crude was then purified by flash purification system using seven pre-packed SNAP Ultra 340 g cartridge running a linear gradient from 2% methanol to 15% methanol in dichloromethane to give the title compound E as an off-white solid. Yield: 30.55 g, 53.5% (NMR in DMSO-d6 showed the presence of 1.1 eq. triethylamine). HPLC (method 9, 220 nm)>99%. LRMS-ESI (m/z) calcd. for $C_{22}H_{27}N_4O_9S$ [M−H]⁻: 523.15. Found: 523.26.

Synthesis of 5-(6-(2,5-dioxo-2,5-dihydro-1H-pyrrol-1-yl)hexanamido)-2-(hydrazine-carbonyl)benzenesulfonic Acid (Sulf07)

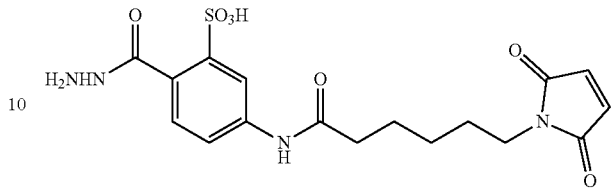

To a cold suspension (4° C.) of E, (10.00 g, 15.98 mmol, 1.00 equiv.) in dichloromethane (50 mL) was added trifluoroacetic acid (18.22 g, 12.31 mL, 159.81 mmol, 10.17 equiv.) over 15 min. The mixture was further stirred at 4° C. for 15 minutes, and then allowed to warm gradually to room temperature and stirred for 150 min. The reaction mixture was added dropwise via a separating funnel to a stirred solution of methyl tert-butyl ether, MTBE, (400 mL) and dichloromethane (200 mL). The resulted white solid was filtered through a 4 Å porosity fritted funnel and washed sequentially with dichloromethane (2×150 mL) and MTBE (1×50 mL), MeOH (1×50 mL) and again MTBE (2×150 mL). The solid was left to dry on the fritted funnel overnight at room temperature for 10 min. Further drying was carried out on high vacuum at 25° C. for 18 h. The final product Sulf07 was obtained as a yellow solid. Yield: 5.786 g, 13.63 mmol, 98.7%, HPLC (method 9, 220 nm)>96%. LRMS-ESI (m/z) calcd. for $C_{17}H_{19}N_4O_7S$ [M−H]⁻: 423.10. Found: 422.95.

Example 2

Compound AE-Keto-Sulf07, 2-(2-((R)-2-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-1-phenylpropylidene)hydrazine-1-carbonyl)-5-(6-(2,5-dioxo-2,5-dihydro-1H-pyrrol-1-yl)hexanamido)benzenesulfonic acid was synthesized as described below and shown in Scheme 5.

Scheme 5

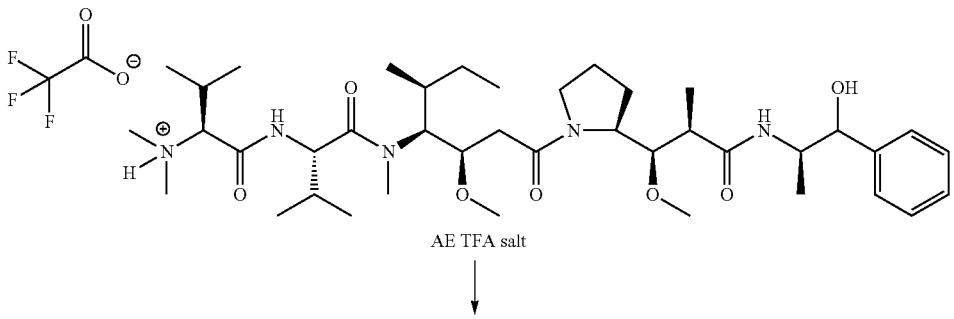

AE TFA salt

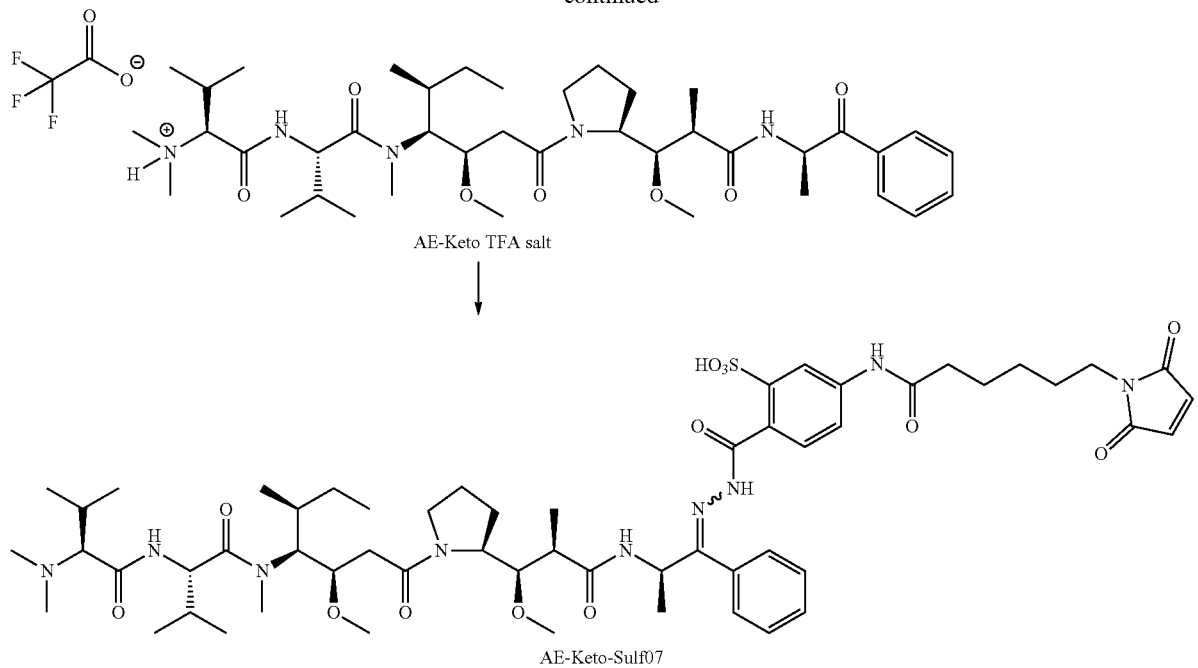

AE-Keto TFA salt

AE-Keto-Sulf07

Synthesis of, (S)-1-(((S)-1-(((3R,4S,5S)-3-methoxy-1-((S)-2-((1R,2R)-1-methoxy-2-methyl-3-oxo-3-(((R)-1-oxo-1-phenylpropan-2-yl)amino)propyl)pyrrolidin-1-yl)-5-methyl-1-oxoheptan-4-yl)(methyl)amino)-3-methyl-1-oxobutan-2-yl)amino)-N,N,3-trimethyl-1-oxobutan-2-aminium 2,2,2-trifluoroacetate (AE-Keto TFA Salt)

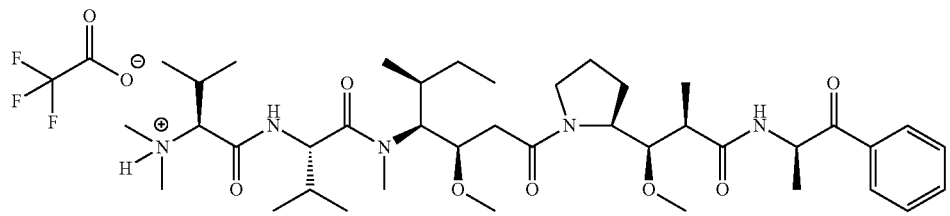 [SMILES: O=C([O-])C(F)(F)F ; CC[C@H](C)[C@@H]([C@@H](CC(=O)N1CCC[C@H]1[C@H](OC)[C@@H](C)C(=O)N[C@H](C)C(=O)c1ccccc1)OC)N(C)C(=O)[C@@H](NC(=O)[C@H](C(C)C)[NH+](C)C)C(C)C]

Route A: Synthesis according to an improved procedure of U.S. Pat. No. 6,884,869-B2

Pyridinium chlorochromate (PCC) (382 mg, 1.772 mmol, 1.5 equiv., Sigma Aldrich) was added to a solution of auristatin E TFA salt (1000 mg, 1.183 mmol, Levena Biopharma) in anhydrous dichloromethane (30 mL) under nitrogen atmosphere. The reaction mixture was stirred at room temperature for 17 h. LC-MS (method 4, positive mode) showed complete conversion of the starting material. The reaction mixture was diluted with 25 mL dichloromethane and washed with brine (3×20 mL). The aqueous phase was extracted once with dichloromethane (20 mL). The combined organic phases were evaporated under reduced pressure at 40° C. The residue was dissolved in 7.5 mL acetonitrile and purified by RP flash chromatography with a pre-packed SNAP Ultra C18 30 g cartridge, using a step gradient from 2% to 40% acetonitrile (+0.1% TFA) in water (+0.1% TFA) over 16 column volumes. Pure product fractions were pooled, acetonitrile was removed under reduced pressure at 40° C. and the residual solvent was lyophilized to give a white solid. Yield: 530 mg, 53%. RP-HPLC (method 2, 220 nm):>95%. LRMS-ESI (m/z) calcd. for $C_{40}H_{68}N_5O_7$ [M+H]$^+$: 730.51. Found: 730.34.

Route B: Synthesis Using Polymer-Bound Oxidizing Agent

IBX-polystyrene (1.13 g, 4.5 eq, 1.34 mmol, loading 1.18 mmol/g, Merck Novabiochem) was suspended in anhydrous dichloromethane (7.5 mL) and stirred gently for 15 min at room temperature. AE TFA salt (250 mg, 295.51 μmol, Sage Chemical Co.) dissolved in anhydrous dichloromethane (5 mL) was added and the mixture was stirred gently at room temperature. After 21 h, full conversion of the starting material to the product was observed by HPLC (method 2, 220 nm). The resin was removed by filtration on folded filter paper (grade 3 hw, Sartorius), washed with dichloromethane and the combined filtrates were evaporated to dryness under reduced pressure at 40° C. The oily residue was triturated with diethyl ether, forming an off-white precipitate which was dried under high vacuum, yielding a foamy, off-white solid. Yield: 171 mg, 69%, HPLC (method 2, 220 nm)>99%. LRMS-ESI (m/z) calcd. for $C_{40}H_{68}N_5O_7$ [M+H]$^+$: 730.51. Found: 730.69; calcd. for $C_{40}H_{66}N_5O_7$ [M−H]$^-$: 728.50. Found: 728.79.

Synthesis of 2-(2-((R)-2-((2R,3R)-3-((S)-1-((3R,4S, 5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-1-phenylpropylidene)hydrazine-1-carbonyl)-5-(6-(2,5-dioxo-2,5-dihydro-1H-pyrrol-1-yl)hexanamido)benzenesulfonic Acid (AE-Keto-Sulf07)

128.78, 128.56, 128.40, 128.31, 127.66, 127.61, 127.10, 120.25, 118.66, 118.56, 116.47, 116.34, 85.45, 81.38, 77.69, 76.74, 71.91, 60.94, 60.20, 58.57, 58.16, 57.05, 55.07, 54.48, 54.39, 49.25, 48.86, 47.18, 46.24, 43.58, 43.12, 41.50, 41.44, 37.15, 36.96, 36.15, 35.01, 31.83, 31.57, 30.04, 29.94, 27.77, 26.68, 26.64, 25.76, 25.39, 25.27, 24.52, 24.50, 24.29, 23.17, 19.30, 19.28, 18.85, 18.62, 18.57, 18.48, 18.20, 17.17, 16.92, 15.58, 15.51, 15.23,

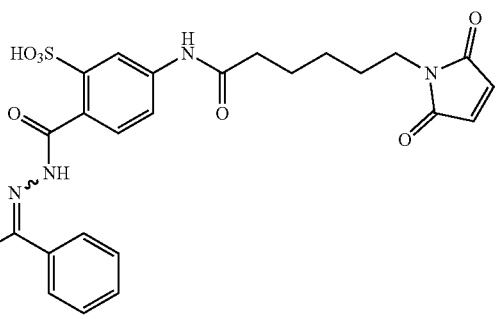

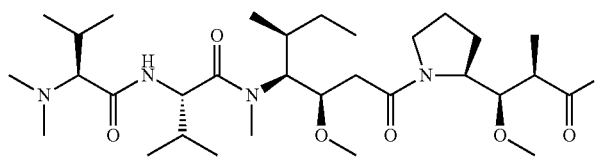

Synthesis 1: Under nitrogen, AE-Keto TFA salt (200 mg, 236.96 µmol) was dissolved in anhydrous ethanol (6 mL), followed by the addition of molecular sieves (0.3 nm beads, 3A). Sulf07 (201 mg, 473.92 µmol, 2 equiv.) dissolved in anhydrous dimethyl sulfoxide (1.5 mL), was added. The yellow solution was stirred at room temperature. Samples for HPLC/LC-MS analyses (methods 2 and 4, 220 nm) were taken after 24 and 44 h. Upon conversion (85% after 44 h), the mixture was filtered through a 0.2 µm PVDF syringe filter, most of the ethanol was removed under reduced pressure. 3 mL of 200 mM sodium phosphate pH 7.2 were added dropwise until the pH of the solution was ~6. The solution (~5 mL) was purified by RP flash chromatography with a pre-packed SNAP Ultra C18 30 g cartridge, using a step gradient from 2% to 50% acetonitrile in water over 16 column volumes. Product fractions were analyzed by HPLC (method 2, 220 nm), pure fractions combined, acetonitrile was removed under reduced pressure and the residual solution was lyophilized to give an off-white fluffy solid. Yield: 113 mg, 42%, melting point: >105° C. HPLC (method 2, 220 nm)>95%. LRMS-ESI (m/z) calcd. for $C_{57}H_{86}N_9O_3$ [M+H]$^+$: 1136.61. Found: 1136.76; calcd. for $C_{57}H_{84}N_9O_3$ [M−H]$^−$: 1134.59. Found: 1135.09. $^1$H NMR (400 MHz, DMSO-d$_6$) δ 11.21 (2×s, 1H), 10.09 (2×s, 1H), 8.66 (d, J=8.3 Hz, 1H), 8.20 (2×d, J=8.4 Hz, 1H), 7.84-7.69 (m, 2H), 7.50-7.41 (m, 1H), 7.35-7.21 (m, 5H), 6.98 (s, 2H), 4.96-4.84 (m, 1H), 4.77-4.60 (m, 1H), 4.56 (td, J=8.6, 2.2 Hz, 1H), 4.03-3.92 (m, 1H), 3.61-3.52 (m, 1H), 3.51-3.41 (m, 2H), 3.38 (t, J=7.0 Hz, 2H), 3.35-3.32 (m, 1H), 3.20 (m, 7H), 3.02 (2×s, 3H), 2.61 (2×s, 6H), 2.47-2.37 (m, 1H), 2.26 (t, J=7.4 Hz, 2H), 2.22-2.04 (m, 3H), 2.04-1.91 (m, 1H), 1.88-1.63 (m, 3H), 1.62-1.43 (m, 7H), 1.37-1.27 (m, 4H), 1.27-1.19 (m, 2H), 1.06 (d, J=6.6 Hz, 2H), 0.98 (d, J=6.6 Hz, 1H), 0.96-0.88 (m, 8H), 0.87-0.81 (m, 5H), 0.80-0.73 (m, 5H). $^{13}$C NMR (101 MHz, DMSO-d$_6$) δ 172.67, 172.38, 172.26, 171.47, 171.45, 171.13, 171.10, 168.76, 168.52, 166.64, 166.23, 164.82, 164.61, 156.63, 155.75, 144.76, 144.68, 140.27, 140.14, 134.46, 133.00, 131.89, 131.79, 14.96, 10.43, 10.25. Note: Some $^1$H-NMR signals are split in two different signals due to the presence of conformers in solution. For this reason the number of peaks in the $^{13}$C-NMR spectrum is higher than the number of carbons expected for AE-Keto-Sulf07.

Synthesis 2: In a 25 mL round bottom flask under nitrogen, AE-Keto (150 mg, 0.177 mmol, 1.0 equiv) and Sulf07 obtained from route C (93 mg, 0.213 mmol, 1.2 equiv) were dissolved in a mixture of anhydrous EtOH (225 µL) and anhydrous DMSO (225 µL). Complete dissolution was achieved after 5 minutes of ultrasonication at room temperature. Activated molecular sieves were added, and the resulting yellow suspension was stirred at room temperature, and the progress was checked by HPLC analysis. After for 22 h, the reaction mixture was transferred to a 2 mL Eppendorf tube, the reaction vial was washed twice with 600 µL DMSO-EtOH (1:1) and the combined portions were centrifuged. The solid was separated from the supernatant. The product was precipitated by the addition of 45 µL of MTBE to the supernatant. The white suspension was centrifuged, and the resulting supernatant was discarded. The purification of the target compound was performed on an Isolera One System (Biotage AB, Upsala, Sweden) equipped with a AQ C18 spherical 20-35 um 100 A 40 gr cartridge running a gradient of 2% to 50% water/acetonitrile. After lyophilisation, the title compound was obtained as a white-off solid. Yield 80 mg, 40%. HPLC (method 10, 220 nm)>97%. NMR and LC-MS analysis in accordance with previously reported.

Example 3

Compound AE-Ester-Sulf07, 2-(2-(1-(4-(((1S,2R)-2-((2R,3R)-3-((S)-1-((3R,4R,5S)-4-((S)-2-((R)-2-(dimethylamino)-3-methylbutanamido)-N,3-dimethylbutanamido)-3-methoxy-5-methylheptanoyl)pyrrolidin-2-yl)-3-methoxy-2-methylpropanamido)-1-phenylpropoxy)carbonyl)phenyl)ethylidene)hydrazine-1-carbonyl)-5-(6-(2,5-dioxo-2,5-dihydro-1H-pyrrol-1-yl)hexanamido)benzenesulfonic acid, was synthesized as described below and shown in Scheme 6.

Scheme 6
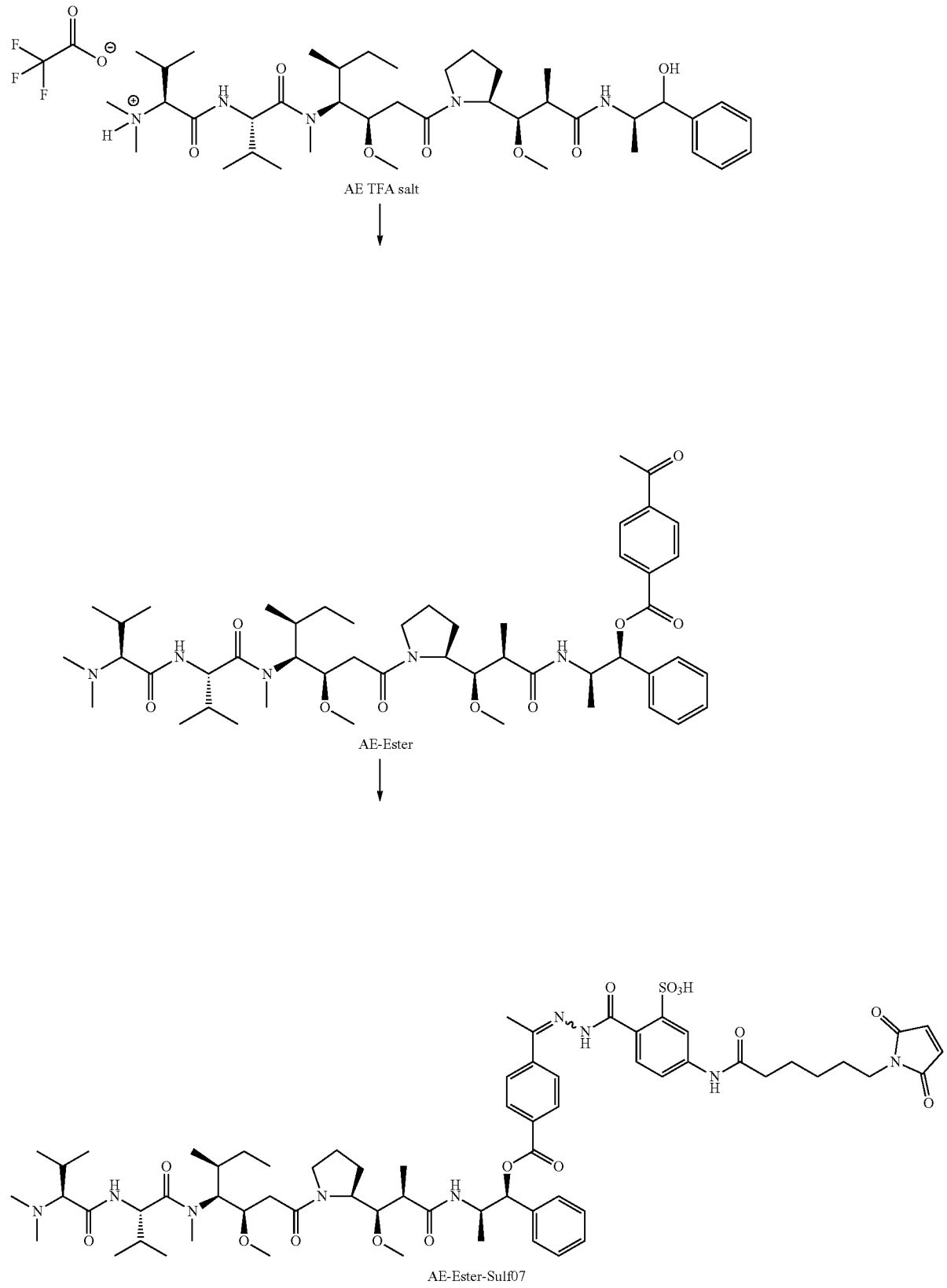

Synthesis of (1S,2R)-2-((3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-1-phenylpropyl 4-acetylbenzoate (AE-Ester)

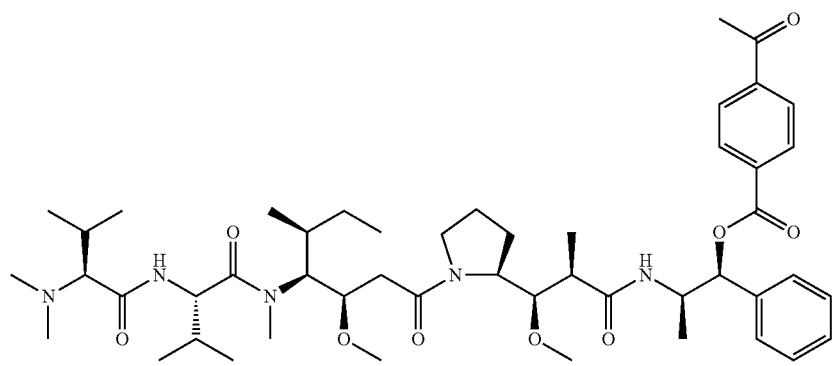 [SMILES: CC[C@H](C)[C@@H]([C@@H](CC(=O)N1CCC[C@H]1[C@H](OC)[C@@H](C)C(=O)N[C@H](C)[C@@H](OC(=O)c1ccc(C(C)=O)cc1)c1ccccc1)OC)N(C)C(=O)[C@@H](NC(=O)[C@H](C(C)C)N(C)C)C(C)C]

Synthesis According to an Improved Procedure of U.S. Pat. No. 6,884,869-B2

To a solution of auristatin E TFA salt (1.0 g, 1.18 mmol, 1.0 equiv., Levena Biopharma) and 4-acetylbenzoic acid (198 mg, 1.42 mmol, 1.2 equiv., Acros Organics) in anhydrous dichloromethane (18 mL) in the presence of molecular sieves (0.3 nm beads, 3 Å) were added 4-dimethylaminopyridine (DMAP, 244 mg, 2.36 mmol, 2.0 equiv., Carbolution) and N,N'-diisopropylcarbodiimide (DIC, 186 μL, 1.42 mmol, 1.2 equiv., Sigma Aldrich). The mixture was stirred at room temperature for 5 h. The progress of the reaction was monitored by HPLC (method 2, 220 nm), showing conversion to the desired product of 81%. DIC (155 μL, 1.18 mmol, 1.0 equiv., Sigma Aldrich) was further added and the mixture was left stirring at room temperature for 18 h, after which HPLC showed 98% reaction conversion to the desired product. During the synthesis of different batches of the compound, it has been noted that when fresh DIC from a newly opened bottle is used, there is no need for the second addition. Molecular sieves and the fine formed precipitate, a DIC by-product, were filtered off through folded filter paper (grade 3 hw, Sartorius), and the resulting clear yellow solution was washed once with HCl (0.1 M, 15 mL). The aqueous layer was back-extracted once with dichloromethane (15 mL), the organic layer was then combined, washed once with brine (15 mL) and dried over sodium sulphate. The solution was concentrated under reduced pressure at 40° C. to give a yellow oil, which was then dissolved in a minimum quantity of dichloromethane (5 mL). Excess diethyl ether (50 mL) was added to produce a white solid. The mixture was left at 2-4° C. for 30 min and then the solid was separated by centrifugation. The precipitation procedure was repeated three times, and the white powder was dried under reduced pressure. Yield: 706 mg, 68% yield. Purity by HPLC (method 2, 220 nm) 98%. LRMS-ESI (m/z) calcd. For $C_{49}H_{75}FN_5O_9$ [M+H]$^+$: 879.20. Found: 878.70.

Synthesis of 2-(2-(1-(4-(((1S,2R)-2-((2R,3R)-3-((S)-1-((3R,4R,5S)-4-((S)-2-((R)-2-(dimethylamino)-3-methylbutanamido)-N,3-dimethylbutanamido)-3-methoxy-5-methylheptanoyl)pyrrolidin-2-yl)-3-methoxy-2-methylpropanamido)-1-phenylpropoxy)carbonyl)phenyl)ethylidene)hydrazine-1-carbonyl)-5-(6-(2,5-dioxo-2,5-dihydro-1H-pyrrol-1-yl)hexanamido)benzenesulfonic Acid (AE-Ester-Sulf07)

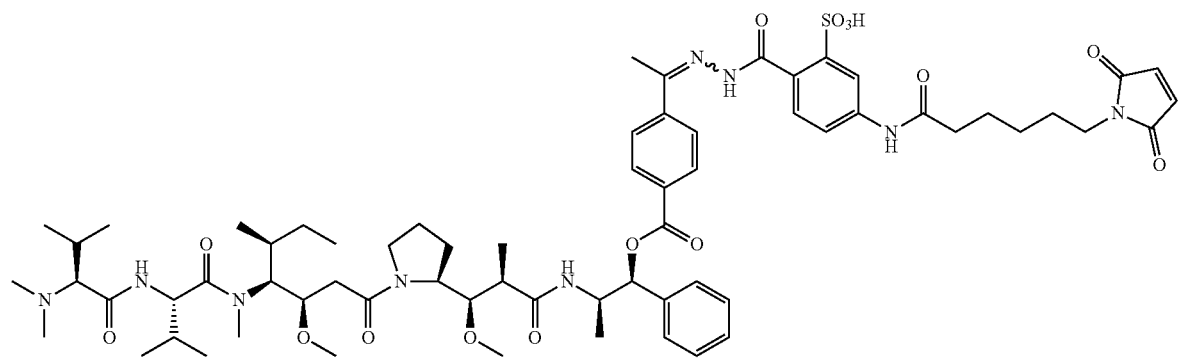 [SMILES: CC[C@H](C)[C@@H]([C@@H](CC(=O)N1CCC[C@H]1[C@H](OC)[C@@H](C)C(=O)N[C@H](C)[C@@H](OC(=O)c1ccc(C(C)=NNC(=O)c2ccc(NC(=O)CCCCCN3C(=O)C=CC3=O)cc2S(=O)(=O)O)cc1)c1ccccc1)OC)N(C)C(=O)[C@@H](NC(=O)[C@H](C(C)C)N(C)C)C(C)C]

Figure 11:
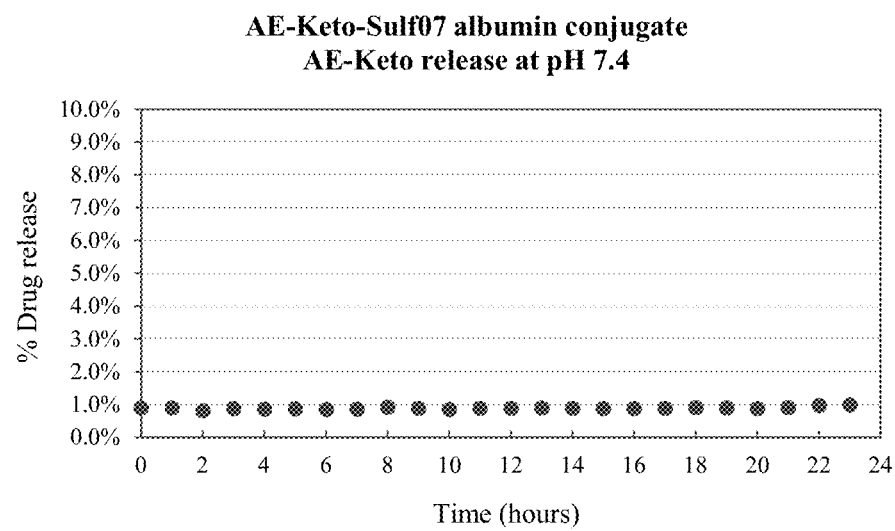
FIG. 11 shows the pH-dependent release of AE-Keto (pH 7.4 (Panel (a) and pH 4.1 (Panel (b)) from human albumin-bound AE-Keto-Sulf07.
Figure 11:
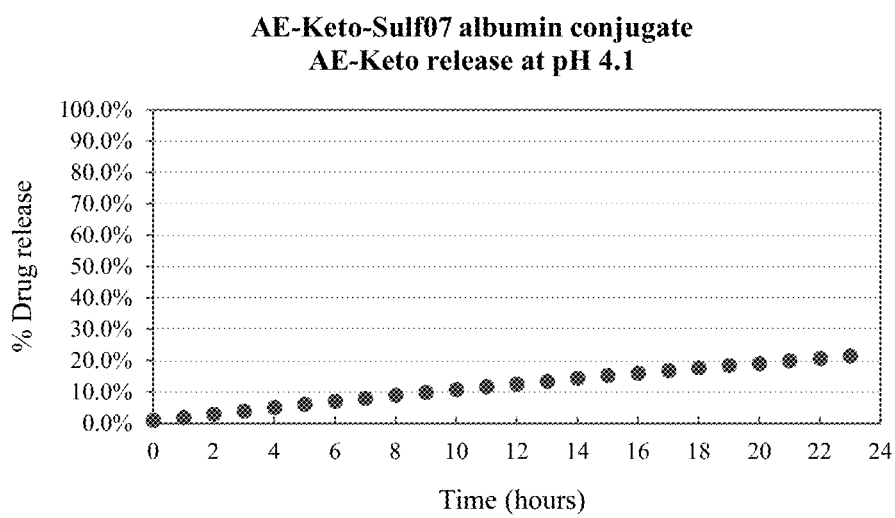
Figure 12:
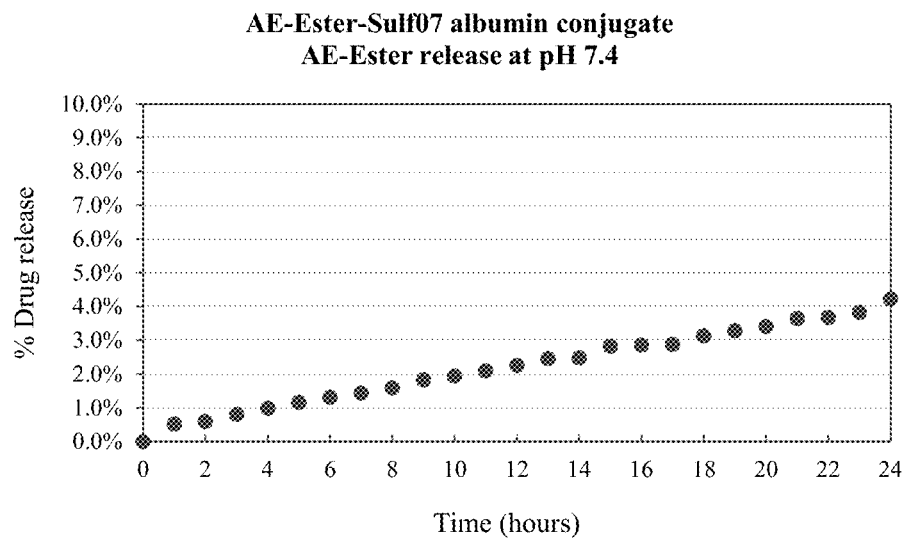
FIG. 12 shows the pH-dependent release of AE-Ester (pH 7.4 (Panel (a) and pH 4.1 (Panel (b)) from human albumin-bound AE-Ester-Sulf07.
Figure 12:
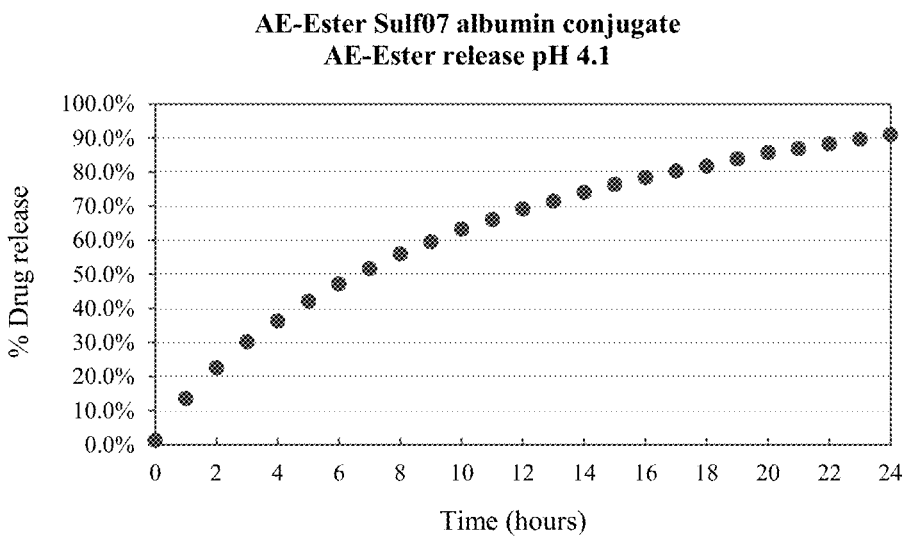

A solution of Sulf07 (164 mg, 0.31 mmol, 1.1 equiv.) in anhydrous dimethyl sulfoxide (2 mL) was added to a solution of AE-Ester (243 mg, 0.28 mmol, 1.0 equiv.) in anhydrous ethanol (8 mL) in the presence of molecular sieves (0.3 nm beads, 3 Å). Para-toluenesulfonic acid (10.5 mg, 0.05 mmol, 0.2 equiv.) was added to catalyse the reaction, and the reaction was then stirred at room temperature. TFA could also be used instead of para-toluenesulfonic acid. The reaction was monitored by HPLC (method 2, 220 nm), showing full conversion after 15 h. The molecular sieves and the fine precipitate formed were removed from the reaction solution by filtration through folded filter paper (grade 3 hw, Sartorius). The solution was precipitated with an excess amount of methyl tert-butyl ether (60 mL) and the mixture was left at 2-4° C. for 30 min. The precipitate was then separated by centrifugation to achieve a yellow sticky solid. The yellow sticky solid was dissolved in methanol/dichloromethane 3/7 (10 mL) and the solution was injected into a flash purification system, with a pre-packed SNAP Ultra 25 g cartridge. The purification was carried on normal-phase using a step gradient, from 100% dichloromethane to 60% dichloromethane/40% methanol in 17 column volumes. The tubes containing the product were combined and dried under high vacuum. Yield: 162 mg, 45% yield. Purity by RP-HPLC (method 2, 220 nm) 96%. LRMS-ESI (m/z) calcd. for $C_{66}H_{93}N_9O_{15}S$ [M+H]$^+$: 1285.58. Found: 1284.20. $^1$H NMR (400 MHz, DMSO-d$_6$) δ 12.24 (d, J=5.3 Hz, 1H), 10.21 (s, 1H), 9.20 (2×br.s, 1H), 8.32-7.90 (m, 8H), 7.74-7.71 (dd, J=8.5, 2.7 Hz, 1H), 7.41-7.27 (m, 5H), 7.00 (s, 2H), 6.13-6.02 (2×d, J=5.0 Hz, 1H), 4.80-4.51 (m, 2H), 4.41-4.23 (m, 1H), 4.09-3.55 (m, 3H), 3.54-3.37 (t, J=7.0 Hz, 3H), 3.27-3.17 (m, 8H), 3.00 (s, 2H), 2.88-2.63 (m, 5H), 2.37-2.30 (m, 6H), 2.22-1.80 (m, 4H), 1.75-1.48 (m, 7H), 1.42-1.22 (m, 6H), 1.18-1.11 (m, 3H), 1.10-1.04 (m, 3H), 1.00-0.74 (m, 20H). $^{13}$C NMR (101 MHz, DMSO) δ 172.93, 172.65, 171.44, 170.94, 168.61, 168.49, 164.59, 164.52, 164.24, 164.16, 149.20, 144.83, 143.05, 142.96, 140.71, 137.97, 137.78, 134.30, 132.25, 129.43, 129.38, 129.31, 129.21, 128.39, 128.31, 126.49, 126.44, 126.35, 125.72, 118.77, 116.77, 85.20, 81.26, 77.65, 77.04, 76.84, 60.82, 60.12, 58.59, 58.03, 57.01, 48.35, 47.76, 47.15, 46.03, 43.60, 42.99, 36.89, 36.11, 31.64, 29.89, 29.73, 27.70, 26.56, 25.70, 25.33, 25.04, 24.42, 24.04, 23.03, 19.16, 18.63, 18.44, 18.37, 15.50, 15.47, 15.29, 15.14, 13.88, 13.84, 10.19, 10.04. Note: Some $^1$H-NMR signals are split in two different signals due to the presence of conformers in solution. For this reason the number of peaks in the $^{13}$C-NMR spectrum is higher than the number of carbons expected for AE-Ester-Sulf07. pH-Dependent release of the human serum albumin conjugates of AE-Keto-Sulf07 and AE-Ester-Sulf07 at pH 7.4 and pH 4.1 (FIGS. 11 and 12)

The albumin-binding auristatin-Sulf07 derivatives were prepared as 2 mM stock solutions in anhydrous DMSO.

Release at pH 7.4: 442.4 µL of 1000 µM of reduced human serum albumin (881 µM free cysteine-34) and 727.6 µL PBS Buffer (4 mM sodium phosphate pH 7.4 and 150 mM NaCl) were added to a sealed HPLC vial and incubated at 37° C. for 30 minutes. After 30 minutes incubation 130 µL of the appropriate DMSO drug stock solution was added to the pre-incubated vial to produce a 200 µM solution of auristatin drug and a 300 µM solution of albumin (free cysteine-34). The mixture was allowed to react for 10 minutes at 37° C. and then analyzed by HPLC (method 7, 20 µL injection). Injections were repeated after 1 hour and then every hour up to 24 hours.

Release at pH 4.1: 408.5 µL of 1000 µM of reduced human serum albumin (881 µM free cysteine-34) and 539.4 µL of water were added to a sealed HPLC vial and incubated at 37° C. for 30 minutes. In a separate vial 190 µL sodium acetate buffer 50 mM pH 3.0 and 24.7 µL 1 M HCl were incubated at 37° C. for 30 minutes. After 30 minutes incubation 120 µL of the appropriate DMSO drug stock solution was added to the pre-incubated vial to produce the albumin drug conjugate. After 10 minutes incubation 132 µL of the sodium acetate buffer solution was added to produce a 200 µM solution of auristatin drug derivative and a 300 µM solution of albumin (free cysteine-34). The resulting solution was analyzed directly by HPLC (method 7). Injection from the vial was repeated after 1 hour and then every hour up to 24 hours.

The percentage of released free drug was determined by HPLC with a calibration curve (200 µM, 100 µM, 50 µM, 25 µM and 12.5 µM) for the free drugs i.e. AE-Keto for AE-Keto-Sulf07 and AE-Ester for AE-Ester-Sulf07. Drug stock solutions were prepared using DMSO as solvent and diluted 10-fold with phosphate buffer (4 mM sodium phosphate pH 7.4 and 150 mM NaCl) before HPLC analysis. Drug release calculations were based on AUC: for AE-Keto at 254 nm and AE-Ester at 310 nm (local UV maximums). The percent of AE-Ester released was higher than the percent of AE-Keto released upon changing the pH form 7.4 to 4.1 (compare FIGS. 11 and 12).

Reconstitution Stability AE-Keto-Sulf07 and AE-Keto-EMCH (FIG. 1)

The albumin-binding AE-Keto drug derivatives were reconstituted in 50 mM sodium phosphate buffer pH 7.6 which contained 5% sucrose (w/v) and 2% 2-hydroxypropyl-β-cyclodextrin (2-HPβCD). Both drugs were reconstituted at a concentration of 1277 µM (equal to 4.5 mg/kg murine xenograft dose), the dissolution of both drugs was confirmed by HPLC (method 2, 254 nm). Stability of the reconstituted drugs was monitored by HPLC at room temperature every 15 minutes over a period of 240 minutes for maleimide hydrolysis and loss of API. AE-Keto-Sulf07 was more stable than AE-Keto-EMCH (see FIG. 1).

Reconstitution Stability AE-Ester-Sulf07 and AE-Ester-EMCH (FIG. 2)

The albumin-binding AE-Ester derivatives were reconstituted in 50 mM sodium phosphate buffer pH 7.6 which contained 5% sucrose (w/v) and 4% 2-HPβCD. Both drugs were reconstituted at a concentration of 655 µM (equal to 2.4 mg/kg murine xenograft dose), the dissolution of both drugs was confirmed by HPLC (method 2, 310 nm). Stability of the reconstituted drugs was monitored by HPLC at room temperature every 15 minutes over a period of 240 minutes for maleimide hydrolysis and loss of API. AE-Ester-Sulf07 was more stable than AE-Ester-EMCH (see FIG. 2).

Binding Kinetics of Auristatin-Sulf07 Derivatives in Human Plasma, Rat Plasma and CD1 Murine Plasma (FIGS. 5-10).

CD1 murine plasma and Sprague Dawley rat plasma were removed from −80° C. storage and allowed to reach room temperature. The thawed plasma was spun down at 13.6 kRPM for 60 seconds, the supernatant was filtered through a filter needle (5 µm) and subsequently through a 0.45 µm CA membrane.

Whole blood was taken from a healthy human volunteer (EDTA collection tube), the plasma was separated from the red blood cells by spinning it down for 3 minutes at 3000 RPM. The plasma was then used directly, within 2 hours of the blood donation. 360 µL of the appropriate plasma was used for each binding experiment.

All binding experiments were carried out in triplicate. The plasma was incubated at 37° C. using an Eppendorf Thermomixer C. After 30 minutes incubation 40 µL of the appropriate albumin-binding auristatin-Sulf07 derivative was dissolved in its reconstitution solution and added to the plasma. Samples (40 µL) were taken after 15 seconds, 2 minutes, 4 minutes, 8 minutes and 15 minutes (5 samples).

The samples were immediately added to 160 µL of acetonitrile (containing 4 µg/mL of 'MMAE as an internal standard) and vortexed for 1 minute.

The solutions were pipetted into an Impact plasma precipitation plate (shaken for 60 seconds) and filtered by vacuum onto a 96 well plate. Remaining drug was determined by LCMS quantification (method 5, 30 µL injection) using MRM MS2 negative mode (multiple reaction monitoring). Parent ions: auristatin F (Mass-744.8), AE-Keto-Sulf07 (Mass-1135.1) and AE-Ester-Sulf07 (Mass-1283.2). Percentage of binding was determined by comparing the AUC for AE-Keto-Sulf07 and AE-Ester-Sulf07 to calibration curves generated by LCMS for each compound.
Procedure: Binding Specificity of Auristatin-Sulf07 Derivatives to Cysteine-34 of Human Serum Albumin (FIGS. 3-4).

The albumin-binding auristatin-Sulf07 derivatives were reconstituted in 50 mM sodium phosphate buffer pH 7.6 and 5% sucrose which contained 2-HPβCD. 2% HPβCD concentration was used to reconstitute the AE-Keto-Sulf07 and 4% for the AE-Ester-Sulf07 respectively. Both drugs were reconstituted at a concentration of 1 mg/mL (AE-Ester-Sulf07 780 µM, AE-Keto-Sulf07 880 µM).

Figure 24:
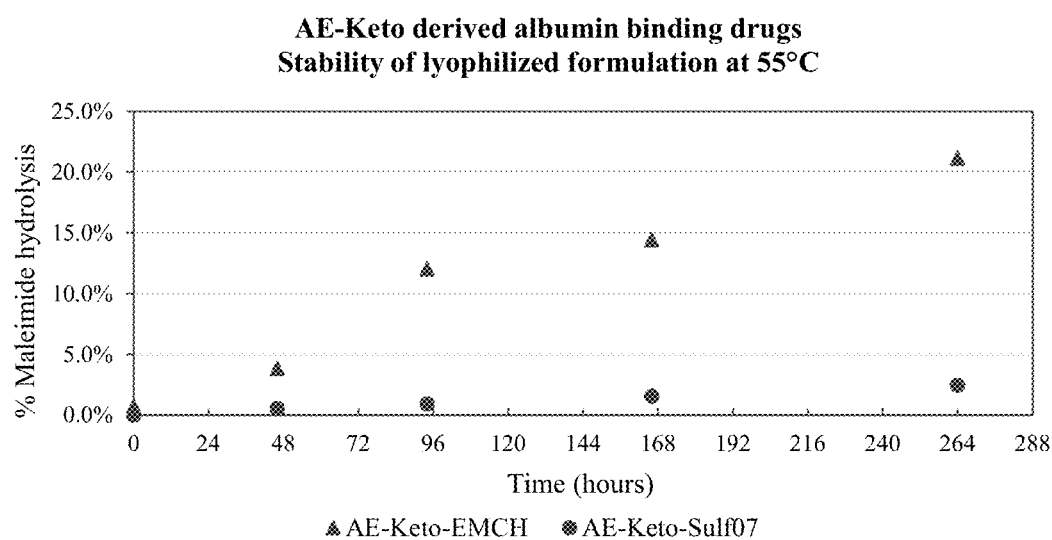
FIG. 24 shows accelerated degradation of lyophilized auristatin formulations as a comparison of AE-Keto-Sulf07 and AE-Keto-EMCH stability.
Figure 25:
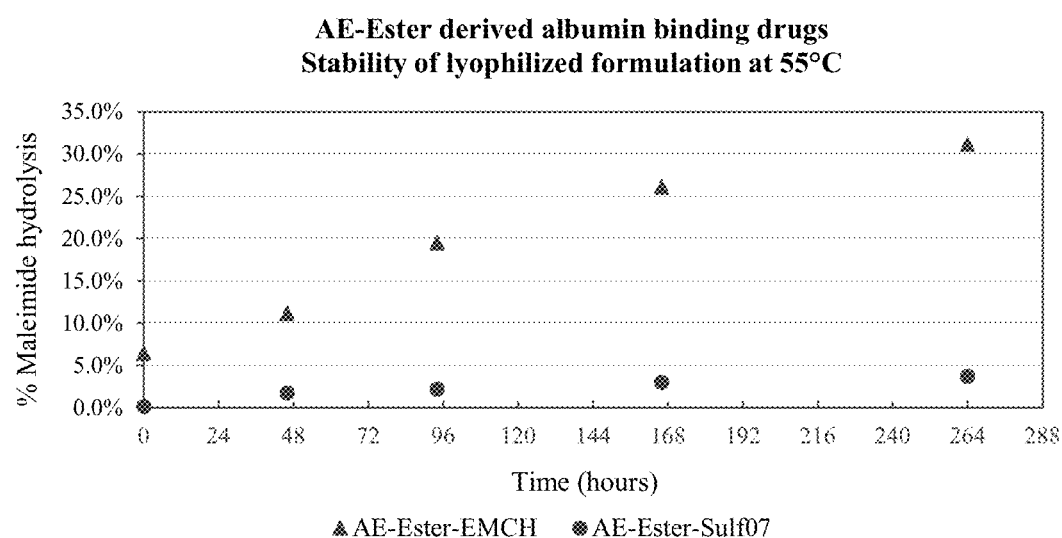
FIG. 25 shows accelerated degradation of lyophilized auristatin formulations as a comparison of AE-Ester-Sulf07 and AE-Ester-EMCH stability.

Human plasma was removed from –80° C. storage and allowed to reach room temperature. The thawed plasma was spun down at 13.6 kRPM for 60 seconds, the supernatant was filtered through filter needle (5 µm) and subsequently through a 0.45 µm CA membrane. 180 µL of the appropriate plasma was used for each binding experiment. The plasma was incubated at 37° C. using an Eppendorf Thermomixer C. After 30 minutes incubation 20 µL of the appropriate albumin-binding auristatin-Sulf07 derivative was added. The albumin-binding drug was allowed to react in the plasma for 5 minutes at 37° C. After 5 minutes the solution was analyzed directly by HPLC hydrophobic interaction chromatography (HIC, method 6, 250 nm) to confirm the site specific conjugation to albumin and formation of the albumin drug conjugate.
Accelerated Degradation of Lyophilized Auristatin Formulations: Comparison of EMCH and Sulf07 Stability (FIGS. 24-25).

The APIs were dissolved in the lyophilization buffer which contained 2-HPβCD, 10 mM sodium citrate pH 6.2, 50% tert-butyl alcohol (V/V)). For the AE-Keto derivatives 2% (w/v) 2-HPβCD was employed to dissolve the AE-Keto APIs at 1.27 mM concentration; for the AE-Ester derivatives 4% (w/v) 2-HPβCD was used to dissolve the APIs at 1.05 mM concentration. The dissolved APIs were sterile filtered using an Acrodisc Fluorodyne II syringe filter (0.2 µm). The sterile solutions were pipetted into lyophilization vials which were then partially sealed using a rubber stopper. The vials were subsequently placed into the freeze dryer for lyophilization. The vials were frozen on the freeze dryer shelf at –40° C. for 2 hours, after 2 hours main drying was started. Main drying was run for 26 hours, parameters: shelf temperature –20° C., vacuum 0.0048 mbar. After main drying, final drying was initiated. Final drying was run for 16 hours, parameters: shelf temperature 20° C., vacuum 0.0047 mbar. Upon completion of final drying the vials were sealed under vacuum.

The sealed vials were incubated at 55° C. using an Eppendorf Thermomixer C with a plate insert (Smartblock) and lid. At chosen time points (t: 0, 46, 94, 166 and 264 hours) samples were removed and dissolved in anhydrous DMSO. Stability of the APIs was determined by HPLC (method 8, 254 nm for AE-Keto derivatives, 310 nm for AE-Ester derivatives). The percentage of maleimide hydrolysis at each time point was determined by comparison to the AUC for each API at time 0. AE-Keto-Sulf07 and AE-Ester-Sulf07 were more stable than the respective EMCH derivatives AE-Keto-EMCH and AE-Ester-EMCH (see FIG. 24 and FIG. 25).

Example 4

General Procedure for the Evaluation of Auristatin E, AE-Keto, and AE-Ester Against a Panel of Tumor Cell Lines
$IC_{50}$ Determination Samples were provided to Charles River Discovery Research Services Germany GmbH as frozen stock solutions in pharmaceutical grade DMSO (Sigma-Aldrich, Taufkirchen, Germany). On each day of the experiment, a frozen aliquot of stock solution was thawed. Subsequent serial dilutions were realized with complete RPMI 1640 cell culture medium using an intermediate dilution plate. 10 µL taken from the intermediate dilution plate were then transferred to 140 µL/well of the cell culture plate. Cells were treated with the test compounds at 10 concentrations in triplicate in half-log steps from 0.003 nM to 100 nM for a period of 96 h.

The compounds were tested in a panel of 6 selected human cancer cell lines by using CellTiter-Blue® Cell Viability assay (Promega, Mannheim, Germany). IC values are reported as absolute $IC_{50}$ values, obtained for a test compound as the geometric mean of $IC_{50}$ values over all cell lines tested.

The cell lines used were LXFL 1674L (established from patient-derived xenograft at Charles River Discovery Research Services Germany GmbH), SW-620 (kindly provided by the NCI, Bethesda, Md., USA), CAL-27 (purchased from DSMZ, Deutsche Sammlung von Mikroorganismen und Zellkulturen, Braunschweig, Germany), RKO, MDA-MB-468, and SK-OV-3 (from ATCC, American Type Culture Collection, Rockville, Md., USA). Authenticity of all cell lines was proven at the DSMZ by STR (short tandem repeat) analysis, a PCR based DNA-fingerprinting methodology. Cell lines were routinely passaged once or twice weekly and maintained in culture for up to 20 passages. Cells were grown at 37° C. in a humidified atmosphere with 5% $CO_2$ in RPMI 1640 medium (25 mM HEPES, with L-glutamine, Biochrom, Berlin, Germany) supplemented with 10% (v/v) fetal calf serum (Sigma-Aldrich, Taufkirchen, Germany) and 0.1 mg/mL gentamicin (Life Technologies, Karlsruhe, Germany). The CellTiter-Blue® Cell Viability Assay was used according to manufacturer's instructions. Briefly, cells were harvested from exponential phase cultures, counted and plated in 96-well flat-bottom microtiter plates at a cell density of 4,000-10,000 cells/well depending on the cell line's growth rate. After a 24 h recovery period to allow the cells to resume exponential growth, 10 µL of culture medium (six control wells/plate) or of culture medium with test compound were added. The compounds were applied at 10 concentrations in triplicate in half-log increments up to 100 nM and cells were treated continuously for 96 h. After four days treatment of cells, 20 µL/well CellTiter-Blue® reagent was added. Following an incubation period of up to 4 h, fluorescence (FU) was measured by using the Enspire Multimode Plate Reader (excitation λ=531 nm, emission λ=615 nm). $IC_{50}$ values were determined with GraphPad Prism bioanalytic software (San Diego, Calif., USA).

Concentration-dependent activities with sigmoidal concentration-effect curves were observed in the six tumor cell lines tested. Geometric mean $IC_{50}$ values were 259±0.11 pM for AE-Keto and 399±0.19 pM for AE-Ester. Compared to the highly potent drugs MMAE (171±0.10 μM) and AE (130±0.05 μM), the AE-Keto and AE-Ester derivatives have similar cytotoxicity in the picomolar range.

Example 5

General Procedure for the Evaluation of Auristatin E and the Albumin-Binding Auristatin E Derivatives in Patient-Derived Tumor Xenograft Models.

Female immunodeficient NMRI nude mice, from Charles River Discovery Research Services Germany GmbH, received unilateral tumor implants subcutaneously in the left flank while under isoflurane anesthesia with human derived tumors, until tumors were palpable and had reached the desired volume.

Animals were kept in cages, the temperature inside the cages was maintained at 25 f 1° C. with a relative humidity of 45-65% and an air change rate of 60-fold per hour. Mice were kept under a 14-hour light/10-hour dark, artificial light cycle. The animals were fed with autoclaved Teklad Global 19% Protein Extruded Diet (T.2019S.12) from Envigo RMS SARL and had access to sterile filtered and acidified (pH 2.5) tap water which was changed twice weekly. Feed and water were provided ad libitum. Prior to therapy, the animals were randomized (7-8 mice per group) considering a comparable median and mean of group tumor volume. Animals were routinely monitored twice daily on working days and daily on Saturdays and Sundays. Starting on day 0, animals were weighed twice a week. Relative body weights (RBW) of individual animals were calculated by dividing the individual absolute body weight on day X ($BW_x$) by the individual body weight on the day of randomization multiplied by 100%. The tumor volume was determined by a two-dimensional measurement with calipers on the day of randomization (Day 0) and then twice weekly. Tumor volumes were calculated according to the following equation:
Tumor Vol [$mm^3$]=1 [mm]×$w^2$ [$mm^2$]×0.5, where "1" is the length and "w" is width of the tumor. The relative volume of an individual tumor on day X ($RTV_x$) was calculated by dividing the absolute individual tumor volume [$mm^3$] of the respective tumor on day X (Tx) by the absolute individual tumor volume of the same tumor on the day of randomization multiplied by 100%. Schedules were applied to the extent that animal welfare policies allow. Termination of individual mice was carried out at tumor volume >2000 $mm^3$ (unilateral). For the evaluation of the statistical significance of anti-tumor efficacy, the non-parametric Kruskal-Wallis test followed by Dunn's method for pairwise comparisons was performed whereby individual RTVs of test and control groups were compared on days on which the minimum T/C values were achieved in the test groups, where T/C [%]=(median $RTV_x$ treated group/median $RTV_x$ control group)×100. Statistical analysis was only carried out if at least 50% of the initially randomized animals in a relevant group were still alive. Comparisons between test groups were carried out for the same days. By convention, p-values ≤0.05 indicate significance of tumor inhibition. Statistical calculations were performed using GraphPad Prism bioanalytic software (San Diego Calif. USA, www.graphpad.com).

General Procedure for the Evaluation of Auristatin E and the Albumin-Binding Auristatin E Derivatives in Dose Finding Studies and in Cell-Line-Derived Tumor Xenograft Models.

Female immunodeficient NMRI nude mice, from Janvier, France, received $5 \times 10^6$-$10^7$ cultured cancer cell in buffer/Matrigel (1:1) inoculated subcutaneously, until tumors were palpable and had reached the desired volume (for xenograft studies).

Animals were kept in cages (Macrolon Type-II wire-mesh) with temperature maintained at 22±1° C., relative humidity of 50 f 10% and an air change rate of 60-fold per hour. Mice were kept under a 12-hour light/12-hour dark, artificial light cycle. The animals were fed with autoclaved Ssniff NM (Soest, Germany), and had access to sterile filtered and acidified (pH 4.0) tap water which was changed twice weekly. Feed and water were provided ad libitum. Prior to therapy, the animals were randomized (3-4 mice per group in dose finding studies and 7-8 mice per group in xenograft studies) considering a comparable median and mean of group tumor volume. The health of the animals was examined at the start of the experiment and twice per day during the experiment. Identification used: ear mark and cage labels. Starting on day 0, animals were weighed two or three times per week and mean body weight per group was related to the initial value in percent to calculate the body weight change (BWC). Tumor diameters were determined by a two-dimensional measurement with a caliper on the day of randomization (Day 0) and then twice or three times per week. Tumor volumes were calculated according to the following equation:
Tumor Vol [$mm^3$]=1 [mm]×$w^2$ [$mm^2$]×0.5, where "1" is the length and "w" is width of the tumor. The relative volume of an individual tumor on day X ($RTV_x$) was calculated by dividing the absolute individual tumor volume [$mm^3$] of the respective tumor on day X (Tx) by the absolute individual tumor volume of the same tumor on the day of randomization multiplied by 100%. Schedules were applied to the extent that animal welfare policies allow. Termination of individual mice was carried out at tumor volume >1500 $mm^3$ (unilateral) or when ulceration was observed. Statistical comparison was performed with the Mann-Whitney U-test.

Dose Finding Studies of Auristatin E and the Albumin-Binding Auristatin E Derivatives AE-Keto-Sulf07 and AE-Ester-Sulf07.

Stock solutions were prepared as follows:
1) 3 mice per group, 26 g average weight on day of randomization: 0.3, 0.6 or 1.2 mg/kg dose auristatin E TFA salt (AE equiv.) dosed once weekly for 4 weeks on day 0, 6, 13, 20≡0.35-1.41 mg/kg≡7.1-28.3 μg/20 g mouse. Sample preparation: 8.5 mg weighed in a 50 mL vial dissolved in 30.0 mL 25/75 tert-butanol/10 mM sodium phosphate buffer, 5% sucrose—pH 7.0; 0.2-0.8 mL were aliquoted in 2 mL vials depending on the final desired final dose. The vials were frozen for 1 h at −40° C. and lyophilized at −20° C. over ~36 h and then stoppered. On day of injection, the lyophilized samples were reconstituted with 0.8 mL of 10 mM sodium phosphate buffer, 20% propylene glycol—pH 7.0.
2) 3 mice per group, 26 g average weight on day of randomization: 1.2 and 2.4 mg/kg AE-Keto-Sulf07 (AE equiv.) dosed twice weekly for 4 weeks ≡1.94-3.87 mg/kg≡38.7 and 77.4 μg/20 g mouse. Sample preparation: 11.0 mg weighed in a 30 mL vial dissolved in 14.2 mL 50/50 tert-butanol/10 mM sodium phosphate buffer, 5% sucrose—pH 7.0; 0.4-0.8 mL were aliquoted in 2 mL vials depending on the final desired final dose. The vials were frozen for 1 h at −40° C. and lyophilized at −20° C. over ~36 h and then stoppered. On the day of injection, the lyophilized samples were reconstituted with 0.8 mL of 10 mM sodium phosphate buffer, 20% propylene glycol—pH 7.0.

3) 3 mice per group, 26 g average weight on day of randomization: 1.2, 1.6 or 2.0 mg/kg AE-Ester-Sulf07 (AE equiv.) dosed twice weekly for 4 weeks on day≡2.18-3.64 mg/kg≡43.7-72.8 µg/20 g mouse. Sample preparation: 19.2 mg weighed in a 30 mL vial dissolved in 26.3 mL 50/50 tert-butanol/10 mM sodium phosphate buffer, 5% sucrose—pH 7.0; 0.48-0.8 mL were aliquoted in 2 mL vials depending on the final desired final dose. The vials were frozen for 1 h at −40° C. and lyophilized at −20° C. over ~36 h and then stoppered. On the day of injection, the lyophilized samples were reconstituted with 0.8 mL of 50 mM sodium phosphate buffer, 5% polysorbate 80 (Tween® 80)—pH 7.6.

4) 4 mice per group, 23 g average weight on day of randomization: 2.0, 2.2 and 2.4 mg/kg AE-Ester-Sulf07 (AE equiv.) dosed twice weekly for 4 weeks on day ≡3.64-4.37 mg/kg≡72.8-87.3 µg/20 g mouse and 4.0, 4.4 and 4.8 mg/kg AE-Ester-Sulf07 (AE equiv.) dosed once weekly for 4 weeks on day 0, 7, 14, 21≡7.28-8.73 mg/kg≡145.6-174.7 µg/20 g mouse. Sample preparation: 56.0 mg weighed in a 50 mL vial dissolved in 32.0 mL 50/50 tert-butanol/10 mM sodium phosphate buffer, 5% sucrose—pH 7.0; 0.33-0.8 mL were aliquoted in 2 mL vials depending on the final desired final dose. The vials were frozen for 1 h at −40° C. and lyophilized at −20° C. over ~36 h and then stoppered. On the day of injection, the lyophilized samples were reconstituted with 0.8 mL of 50 mM sodium phosphate buffer, 2% polysorbate 80 (Tween® 80)—pH 7.6.

The 1.2 and 0.6 mg/kg doses of auristatin E showed high toxicity and no animal survived after the first and second injection respectively. The 0.3 mg/kg dose was well tolerated. In later studies it was found that AE was tolerated at 0.3 mg/kg injected biweekly for four weeks (total of eight injections), and this dose was therefore used in xenograft studies as the maximum tolerated dose (MTD).

All doses tested for AE-Keto-Sulf07 injected eight times on a biweekly schedule were well tolerated. In later xenograft studies the dose for this drug was increased up to 6.5 mg/kg on the same dosing regimen, provoking at this highest dose body weight loss in one mouse and general bad health in a second mouse, and the treatment had to be stopped after five injections rather than eight as planned. Such dose was therefore considered above the MTD and 4.5 mg/kg was selected as safe dose.

AE-Ester-Sulf07 was initially tested up to 2.0 mg/kg dosed twice weekly for four weeks with no evident sign of toxicity. Because skin irritation was later observed in xenograft studies, a second dose finding study was repeated at 2.0, 2.2 and 2.4 mg/kg dosed twice per week over four weeks and compared with the respective doubled doses of 4.0, 4.4 and 4.8 mg/kg injected only once per week. No body weight change was observed, but skin irritation appeared after 9-14 days in all groups. Earlier and more frequent skin irritation was observed for higher doses. The side effect seemed to be reversible as the irritations started to heal after the end of the treatment. The group treated with 4.0 mg/kg once weekly showed the lowest side effect, while no significant difference was observed among the other groups.

Evaluation Criteria for Auristatin E and the Albumin-Binding Auristatin E Derivatives in Tumor Xenograft Models The efficacy of each drug was determined based on the tumor volume reduction (% of tumor volume on selected day compared to day 0): complete remission <10%; partial remission >10-50%; minor remission >50-75%; stable disease >75-125%; progressive disease >125% compared to initial tumor volume.

Figure 13:
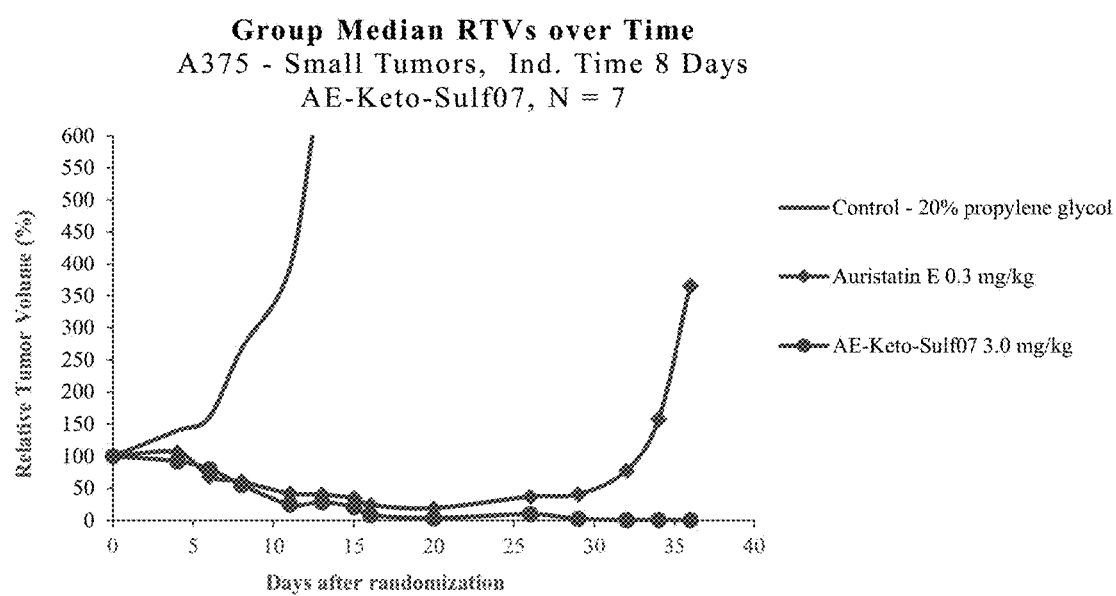
FIG. 13 shows the antitumor effect of auristatin E and AE-Keto-Sulf07, in comparison to control group in the malignant melanoma cancer model A375, average median starting tumor volume ~134 mm$^3$.

Evaluation of Auristatin E and the Albumin-Binding Auristatin E Derivative AE-Keto-Sulf07 in a Human Malignant Melanoma Cancer Model A375—Small Tumors (FIG. 13).

The evaluation of auristatin E and the albumin-binding auristatin E derivative AE-Keto-Sulf07 in a human malignant melanoma cancer model A375 was carried out as described in the general procedure for cell-line-derived xenograft models.

Stock solutions were prepared as follows:

1) 7 mice, 29 g average weight, 135 mm$^3$ average median tumor volume on day of randomization: 0.3 mg/kg auristatin E TFA salt (AE equiv.) dosed twice weekly for 3 weeks on day 0, 6, 9, 13, 16, 19≡0.35 mg/kg≡7.1 µg/20 g mouse. Sample preparation: 2 mg weighed in a 30 mL vial dissolved in 28.3 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 10 mM sodium phosphate buffer, 20% propylene glycol—pH 7.0.

2) 7 mice, 28 g average weight, 137 mm$^3$ average median tumor volume on day of randomization: 3.0 mg/kg AE-Keto-Sulf07 (AE equiv.) dosed twice weekly for 3 weeks on day 0, 6, 9, 13, 16, 19≡5.32 mg/kg≡106.3 µg/20 g mouse. Sample preparation: 19.2 mg weighed in a 30 mL vial dissolved in 19.0 mL 50/50 tert-butanol/ 10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 10 mM sodium phosphate buffer, 20% propylene glycol—pH 7.0.

Tumor growth development in the melanoma xenograft model A375 showed statistically significant antitumor efficacy of compound AE-Keto-Sulf07 at 3.0 mg/kg versus auristatin E 0.3 mg/kg dose, both injected six times twice weekly ($p<0.01$ from day 27 to day 37). Mice treated with auristatin E reached a state of stable disease until day 21, after which the tumor started to grow again. In contrast, mice in the AE-Keto-Sulf07 treated group achieved long term tumor regression, showing complete remission from day 19 until the end of the study on day 37 (1 mm$^3$ final tumor volume).

Mice in the group treated with AE-Keto-Sulf07 had only a slight reduction in body weight growth compared to the control, but no detectable side effects were observed.

Figure 14:
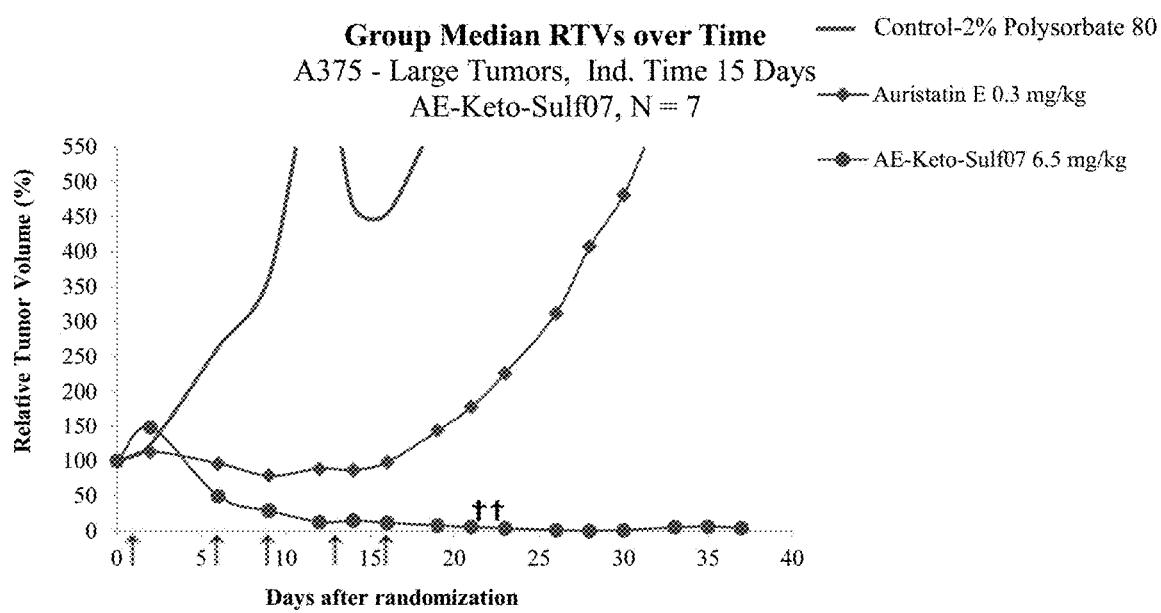
FIG. 14 shows the antitumor effect of auristatin E and AE-Keto-Sulf07, in comparison to control group in the malignant melanoma cancer model A375, average median starting tumor volume ~332 mm$^3$.

Evaluation of Auristatin E and the Albumin-Binding Auristatin E Derivative AE-Keto-Sulf07 in a Human Malignant Melanoma Cancer Model A375—Large Tumors (FIG. 14).

The evaluation of auristatin E and the albumin-binding auristatin E derivative AE-Keto-Sulf07 in a human malignant melanoma cancer model A375 was carried out as described in the general procedure for cell-line-derived xenograft models.

Stock solutions were prepared as follows:

1) 7 mice, 28 g average weight, 310 mm$^3$ average median tumor volume on day of randomization: 0.3 mg/kg auristatin E TFA salt (AE equiv.) dosed twice weekly for 3 weeks on day 1, 6, 9, 13, 16≡0.35 mg/kg≡7.1 µg/20 g mouse. Sample preparation: 2 mg weighed in a 30 mL vial dissolved in 28.3 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On day of injection, the lyophilized samples were reconstituted with 1.2 mL of 10 mM sodium phosphate buffer, 20% propylene glycol—pH 7.0.

2) 7 mice, 27 g average weight, 331 mm³ average median tumor volume on day of randomization: 6.5 mg/kg AE-Keto-Sulf07 (AE equiv.) dosed twice weekly for 3 weeks on day 1, 6, 9, 13, 16≡11.52 mg/kg≡230.4 µg/20 g mouse. Sample preparation: 28.0 mg weighed in a 30 mL vial dissolved in 12.2 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 50 mM sodium phosphate buffer, 2% polysorbate 80 (Tween® 80)—pH 7.6.

The antitumor efficacy of the compound AE-Keto-Sulf07 was also tested in mice bearing larger malignant melanoma A375 tumors (~320 mm³), to prove that the drug efficacy is not limited to small tumors. Mice treated with AE-Keto-Sulf07 at 6.5 mg/kg showed a statistically significant improvement in antitumor effect compared to the group treated with auristatin E at 0.3 mg/kg dose, both injected five times twice weekly (p<0.01 from day 9 until day 33). Auristatin E showed initial stable disease until day 14 to then grow steadily, while mice in the AE-Keto-Sulf07 treated group registered a complete remission from day 19 until the end of the study on day 37, reaching the minimum tumor volume of 1 mm³ on day 28 (12 day after the last treatment) and ~14 mm³ at the end of the study, resulting in a long-term effect despite of the relative large median starting tumor volume.

AE-Keto-Sulf07 caused a transient body weight loss (13% reached on day 21) and two mice had to be sacrificed for general bad conditions.

Figure 15:
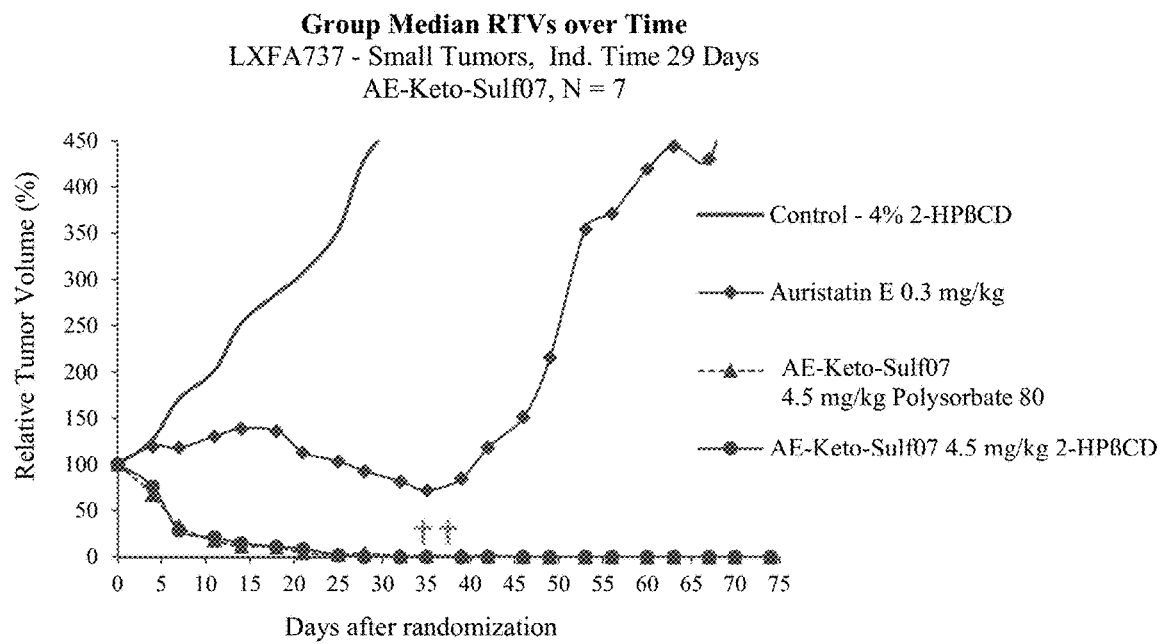
FIG. 15 shows the antitumor effect of auristatin E and AE-Keto-Sulf07, in comparison to control group in the NSCLC xenograft model LXFA737, average median starting tumor volume ~132 mm$^3$.

Evaluation of Auristatin E and the Albumin-Binding Auristatin E Derivative AE-Keto-Sulf07 in a Human Non-Small Cell Lung Cancer Model LXFA737—Small Tumors (FIG. 15).

The evaluation of auristatin E and the albumin-binding auristatin E derivative AE-Keto-Sulf07 in a human non-small cell lung cancer model LXFA737 was carried out as described in the general procedure for patient-derived xenograft models.

Stock solutions were prepared as follows:

1) 7 mice, 27 g average weight, 137 mm³ average median tumor volume on day of randomization: 0.3 mg/kg auristatin E TFA salt (AE equiv.) dosed twice weekly for 4 weeks on day 0, 4, 7, 11, 14, 18, 21, 25≡0.35 mg/kg≡7.1 µg/20 g mouse. Sample preparation: 2 mg weighed in a 30 mL vial dissolved in 28.3 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On day of injection, the lyophilized samples were reconstituted with 1.2 mL of 10 mM sodium phosphate buffer, 20% propylene glycol—pH 7.0.

2) 7 mice, 26 g average weight, 128 mm³ average median tumor volume on day of randomization: 4.5 mg/kg AE-Keto-Sulf07 (AE equiv.) dosed twice weekly for 4 weeks on day 0, 4, 7, 11, 14, 18, 21, 25≡7.98 mg/kg≡159.5 µg/20 g mouse. Sample preparation: 38 mg weighed in a 30 mL vial dissolved in 23.8 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 50 mM sodium phosphate buffer, 2% 2-hydroxypropyl-β-cyclodextrin 2-HPßCD—pH 7.6.

3) 7 mice, 27 g average weight, 130 mm³ average median tumor volume on day of randomization: 4.5 mg/kg AE-Keto-Sulf07 (AE equiv.) dosed twice weekly for 4 weeks on day 0, 4, 7, 11, 14, 18, 21, 25≡7.98 mg/kg≡159.5 µg/20 g mouse. Sample preparation: 38 mg weighed in a 30 mL vial dissolved in 23.8 mL 50/50 tert-butanol/10 mM sodium citrate buffer, 5% sucrose—pH 6; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 50 mM sodium phosphate buffer, 2% polysorbate 80 (Tween® 80)—pH 7.6.

Tumor growth development in the NSCLC xenograft model LXFE737 showed superior antitumor efficacy of compound AE-Keto-Sulf07 at 4.5 mg/kg (both in polysorbate 80 (Tween® 80) and 2-HPßCD buffers) versus auristatin E at 0.3 mg/kg dosed 8 times twice weekly with statistical significance (p<0.01 on day 56 and 63). Tumors in the auristatin E treated group stayed only temporarily in a status of stable disease (from day 21 to day 42) and grew significantly after the end of the therapy. In contrast, mice treated with AE-Keto-Sulf07 reached complete tumor remission on day 28, 3 days after the end of therapy, bringing the tumor volume down to an unmeasurable level until the end of the study on day 74 (independently of the buffer used), resulting in a long term antitumor effect.

Body weight change versus the control showed a partial increase in toxicity in the group treated with AE-Keto-Sulf07. On day 32 a maximum body weight loss was registered (−7%) without other signs of toxicity in the case of 2-HPßCD, while two mice had to be sacrificed for general bad conditions when the drug was administered in polysorbate 80 (Tween® 80).

Figure 16:
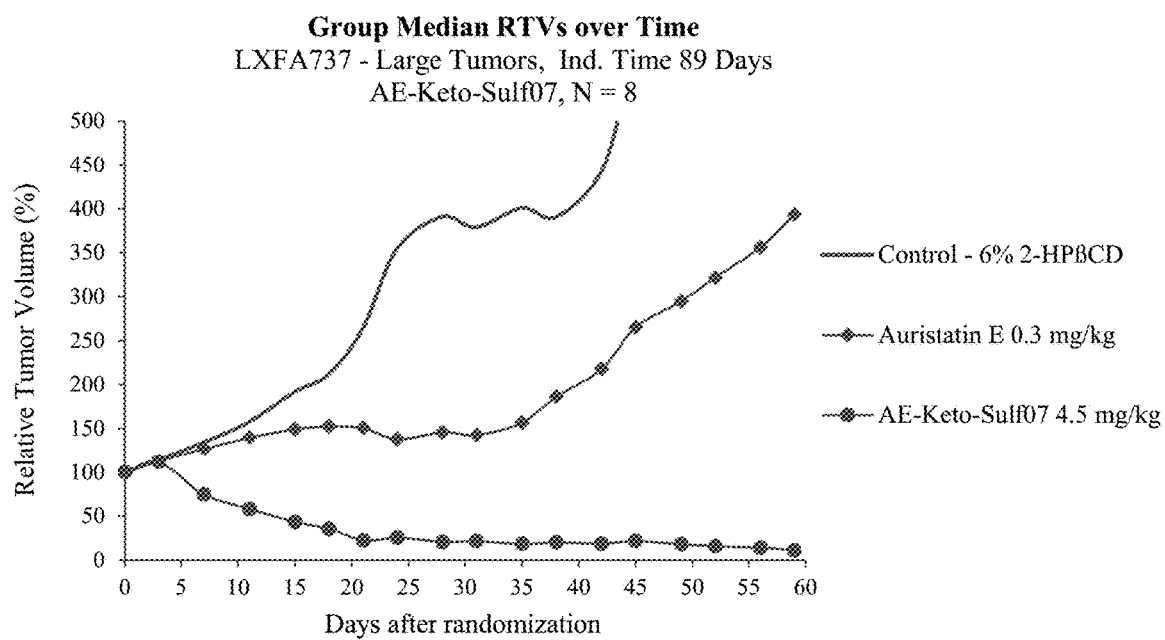
FIG. 16 shows the antitumor effect of auristatin E and AE-Keto-Sulf07, in comparison to control group in the NSCLC xenograft model LXFA737, average median starting tumor volume ~330 mm$^3$.

Evaluation of Auristatin E and the Albumin-Binding Auristatin E Derivative AE-Keto-Sulf07 in a Human Non-Small Cell Lung Cancer Model LXFA737—Large Tumors (FIG. 16).

The evaluation of auristatin E and the albumin-binding auristatin E derivative AE-Keto-Sulf07 in a human non-small cell lung cancer model LXFA737 was carried out as described in the general procedure for patient-derived xenograft models.

Stock solutions were prepared as follows:

1) 8 mice, 26 g average weight, 324 mm³ average median tumor volume on day of randomization: 0.3 mg/kg auristatin E TFA salt (AE equiv.) dosed twice weekly for 4 weeks on day 1, 5, 8, 12, 15, 19, 22, 26≡0.35 mg/kg≡7.1 µg/20 g mouse. Sample preparation: 3 mg weighed in a 100 mL vial dissolved in 43.3 mL 50/50 tert-butanol/10 mM sodium phosphate buffer, 5% sucrose—pH 7.0; 2.4 mL were aliquoted in 4 mL vials. The vials were frozen for 1 h at −40° C. and lyophilized at −20° C. over ~36 h and then stoppered. On day of injection, the lyophilized samples were reconstituted with 2.4 mL of 10 mM sodium phosphate buffer, 20% propylene glycol—pH 7.0.

2) 8 mice, 28 g average weight, 342 mm³ average median tumor volume on day of randomization: 4.5 mg/kg AE-Keto-Sulf07 (AE equiv.) dosed twice weekly for 4 weeks on day 1, 5, 8, 12, 15, 19, 22, 26=6.99 mg/kg≡139.7 µg/20 g mouse. Sample preparation: 51 mg weighed in a 100 mL vial dissolved in 36.5 mL 50/50 tert-butanol/10 mM sodium citrate buffer, 3% 2-HPßCD—pH 6.2; 2.4 mL were aliquoted in 4 mL vials. The vials were frozen for 1 h at −40° C. and lyophilized at −20° C. over ~36 h and then stoppered. On the day of injection, the lyophilized samples were reconstituted with 2.4 mL of 50 mM sodium phosphate buffer, 5% sucrose—pH 7.6.

Tumor growth development in the NSCLC xenograft model LXFE737 showed superior antitumor efficacy of compound AE-Keto-Sulf07 at 4.5 mg/kg versus auristatin E at 0.3 mg/kg, both dosed 8 times twice weekly, with statistical significance ($p<0.01$ on day 28). Tumors in the auristatin E treated group did not show any activity, while mice treated with AE-Keto-Sulf07 reached partial tumor remission on day 15 until the end of the study on day 59, resulting in a long term antitumor effect.

No side effects were registered.

Figure 17:
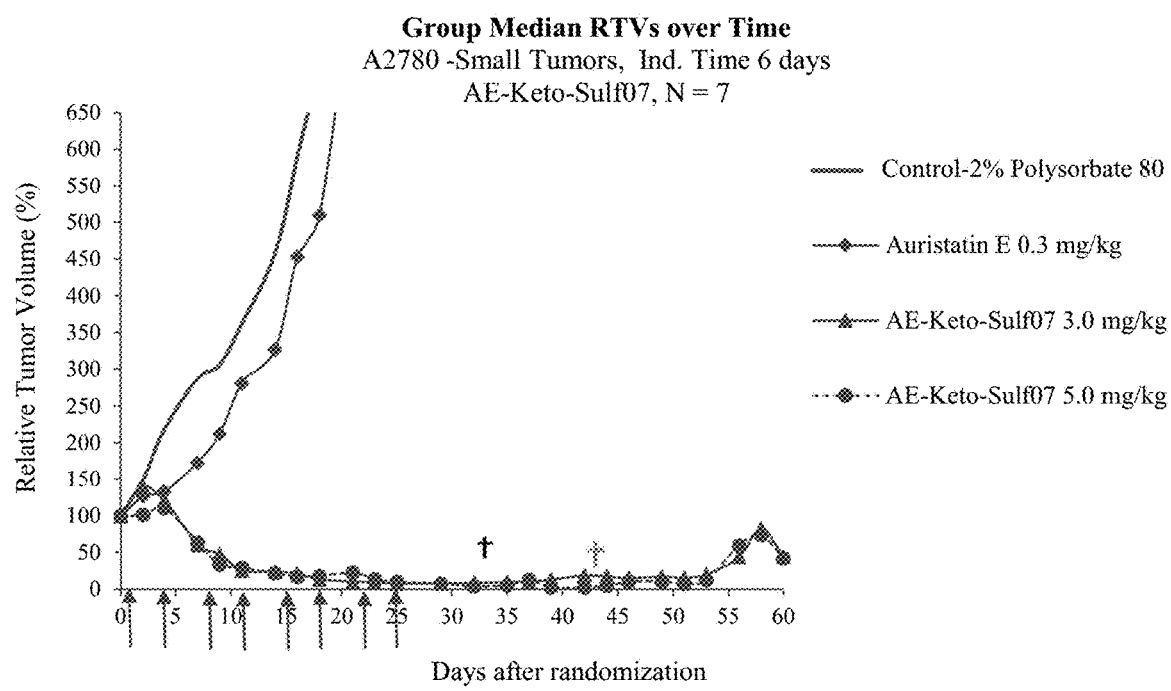
FIG. 17 shows the antitumor effect of auristatin E and AE-Keto-Sulf07, in comparison to control group in the human ovarian carcinoma model A2780, average median starting tumor volume ~148 mm$^3$.

Evaluation of Auristatin E and the Albumin-Binding Auristatin E Derivative AE-Keto-Sulf07 in a Human Ovarian Carcinoma Model A2780—Small Tumors (FIG. 17).

The evaluation of auristatin E and the albumin-binding auristatin E derivative AE-Keto-Sulf07 in a human ovarian carcinoma model A2780 was carried out as described in the general procedure for cell-line-derived xenograft models.

Stock solutions were prepared as follows:

1) 7 mice, 27 g average weight, 147 mm³ average median tumor volume on day of randomization: 0.3 mg/kg auristatin E TFA salt (AE equiv.) dosed twice weekly for 4 weeks on day 1, 4, 8, 11, 15, 18, 22, 25=0.35 mg/kg≡7.1 µg/20 g mouse. Sample preparation: 2 mg weighed in a 30 mL vial dissolved in 28.3 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On day of injection, the lyophilized samples were reconstituted with 1.2 mL of 10 mM sodium phosphate buffer, 20% propylene glycol—pH 7.0.

2) 7 mice, 27 g average weight, 153 mm³ average median tumor volume on day of randomization: 3.0 mg/kg AE-Keto-Sulf07 (AE equiv.) dosed twice weekly for 4 weeks on day 1, 4, 8, 11, 15, 18, 22, 25≡5.32 mg/kg≡106.3 µg/20 g mouse. Sample preparation: 51.0 mg weighed in a 30 mL vial dissolved in 28.8 mL 50/50 tert-butanol/10 mM sodium phosphate buffer, 5% sucrose—pH 7.0; 0.72 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 50 mM sodium phosphate buffer, 2% polysorbate 80 (Tween® 80)—pH 7.6.

3) 7 mice, 25 g average weight, 141 mm³ average median tumor volume on day of randomization: 5.0 mg/kg AE-Keto-Sulf07 (AE equiv.) dosed twice weekly for 4 weeks on day 1, 4, 8, 11, 15, 18, 22, 25≡8.86 mg/kg≡177.2 µg/20 g mouse. Sample preparation: 51.0 mg weighed in a 30 mL vial dissolved in 28.8 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 50 mM sodium phosphate buffer, 2% polysorbate 80 (Tween® 80)—pH 7.6.

Tumor growth development in the ovarian carcinoma model A2780 showed statistically significant superior antitumor efficacy of compound AE-Keto-Sulf07 at 3.0 and 5.0 mg/kg versus auristatin E at 0.3 mg/kg dose, injected eight times twice weekly ($p<0.01$ from day 7 to day 29). Mice treated with auristatin E did not achieve any antitumor effect, and the tumors grew comparably to the ones treated with the control group. Therapy with AE-Keto-Sulf07 however induced partial remission from day 9 until the end of the study on day 60, with a transient complete remission from day 23 to day 35 for the lower dose and from day 25 to day 51 for the higher dose, resulting in long term tumor regression, independently from the dose.

AE-Keto-Sulf07 treated groups caused a transient body weight loss of ~2% after the first treatment. One mouse from the higher dose group was found dead on day 35, and one from the lower dose group had to be sacrificed on day 42 for general bad conditions.

Figure 18:
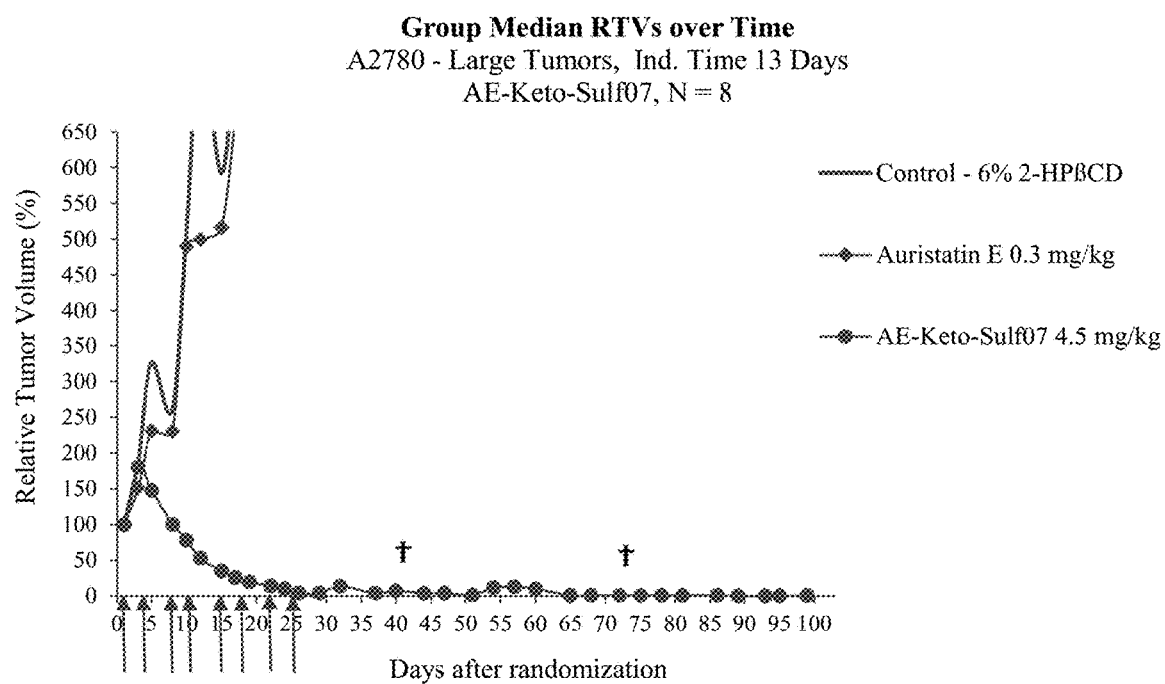
FIG. 18 shows the antitumor effect of auristatin E and AE-Keto-Sulf07, in comparison to control group in the human ovarian carcinoma model A2780, average median starting tumor volume ~351 mm$^3$.

Evaluation of Auristatin E and the Albumin-Binding Auristatin E Derivative AE-Keto-Sulf07 in a Human Ovarian Carcinoma Model A2780—Large Tumors (FIG. 18).

The evaluation of auristatin E and the albumin-binding auristatin E derivative AE-Keto-Sulf07 in a human ovarian carcinoma model A2780 was carried out as described in the general procedure for cell-line-derived xenograft models.

Stock solutions were prepared as follows:

1) 8 mice, 28 g average weight, 341 mm³ average median tumor volume on day of randomization: 0.3 mg/kg auristatin E TFA salt (AE equiv.) dosed twice weekly for 4 weeks on day 1, 4, 8, 11, 15, 18, 22, 25=0.35 mg/kg≡7.1 µg/20 g mouse. Sample preparation: 3.7 mg weighed in a 100 mL vial dissolved in 52.3 mL 50/50 tert-butanol/10 mM sodium phosphate buffer, 5% sucrose—pH 7.0; 1.5 mL were aliquoted in 4 mL vials. The vials were frozen for 1 h at −40° C. and lyophilized at −20° C. over ~36 h and then stoppered. On day of injection, the lyophilized samples were reconstituted with 1.5 mL of 10 mM sodium phosphate buffer, 20% propylene glycol—pH 7.0.

2) 8 mice, 28 g average weight, 378 mm³ average median tumor volume on day of randomization: 4.5 mg/kg AE-Keto-Sulf07 (AE equiv.) dosed twice weekly for 4 weeks on day 1, 4, 8, 11, 15, 18, 22, 25=6.99 mg/kg≡139.7 µg/20 g mouse. Sample preparation: 40.0 mg weighed in a 30 mL vial dissolved in 28.6 mL 50/50 tert-butanol/10 mM sodium phosphate buffer, 5% sucrose—pH 7.0; 1.5 mL were aliquoted in 4 mL vials. The vials were frozen for 1 h at −40° C. and lyophilized at −20° C. over ~36 h and then stoppered. On the day of injection, the lyophilized samples were reconstituted with 1.5 mL of 50 mM sodium phosphate buffer, 2% 2-HPßCD—pH 7.6.

The antitumor efficacy of the compound AE-Keto-Sulf07 was also tested on mice bearing larger tumors (~360 mm³) of the human ovarian carcinoma model A2780. The drug showed statistically significant superior antitumor effect dosed at 4.5 mg/kg versus auristatin E dosed at 0.3 mg/kg, both injected eight times twice weekly ($p<0.001$ from day 22 to day 40). Mice treated with auristatin E did not achieve any antitumor effect, in contrast mice treated with AE-Keto-Sulf07 showed complete remission from day 26 until the end of the study on day 103, reaching a long term tumor regression, as already observed with smaller tumors.

AE-Keto-Sulf07 treated mice had only a slightly reduced body weight growth compared to the control.

Figure 19:
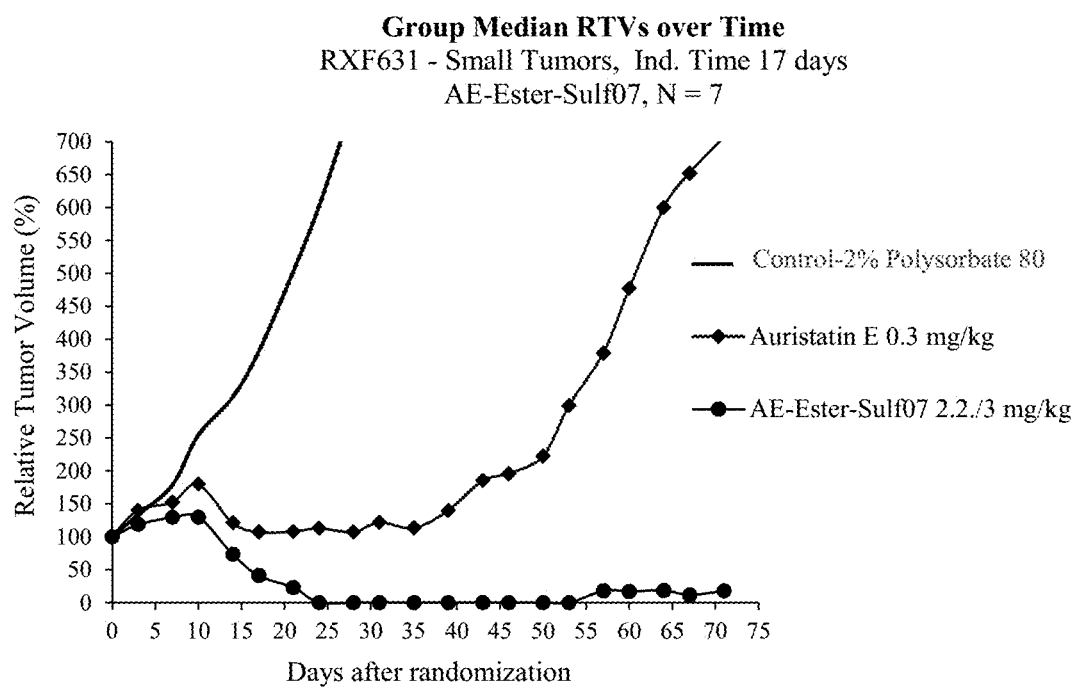
FIG. 19 shows the antitumor effect of auristatin E and AE-Ester-Sulf07, in comparison to control group in the renal cell cancer model RXF631, starting tumor volume ~140 mm$^3$.

Initial Evaluation of Auristatin E and the Albumin-Binding Auristatin E Derivative AE-Ester-Sulf07 in a Human Renal Cell Cancer Model RXF631—Small Tumors (FIG. 19).

The initial evaluation of auristatin E and the albumin-binding auristatin E derivative AE-Ester-Sulf07 in a human renal cell cancer model RXF631 was carried out as described in the general procedure for a patient-derived xenograft model.

For this in vivo experiment stock solutions were prepared as follows:

1) 7 mice, 25 g average weight, 138 mm$^3$ average tumor volume on day of randomization: 0.3 mg/kg auristatin E TFA salt (AE equiv.) dosed twice weekly for 4 weeks on day 1, 5, 8, 12, 15, 19, 22, 26=0.35 mg/kg=7.1 μg/20 g mouse. Sample preparation: 2 mg weighed in a 30 mL vial dissolved in 28.3 mL 50/50 tert-butanol/10 mM sodium phosphate buffer, 5% sucrose—pH 7.0; 1.2 mL were aliquoted in 4 mL vials. Frozen for 1 h at −40° C. and lyophilized at −20° C. over ~36 h and then stoppered. On day of injection, the lyophilized samples were reconstituted with 1.2 mL of 10 mM sodium phosphate buffer, 20% propylene glycol—pH 7.0.
2) 7 mice, 26 g average weight, 141 mm$^3$ average tumor volume on day of randomization: 2.2-3.0 mg/kg AE-Ester-Sulf07 (AE equiv.) dosed twice weekly for 4 weeks on day 1, 5, 8, 12, 15, 19, 26=4.00 mg/kg=80.1 μg/20 g mouse. Sample preparation: 15.7 mg weighed in a 30 mL vial dissolved in 19.6 mL 50/50 tert-butanol/10 mM sodium phosphate buffer, 5% sucrose—pH 7.0; 1.2 mL were aliquoted in 4 mL vials. Frozen for 1 h at −40° C. and lyophilized at −20° C. over ~36 h and then stoppered. On the day of injection, the lyophilized samples were reconstituted with 1.2 mL of 50 mM sodium phosphate buffer, 2% polysorbate 80 (Tween® 80)—pH 7.6.

Tumor growth development in the renal cell cancer model RXF631 shows statistically significant superior antitumor efficacy of compound AE-Ester-Sulf07 dosed at 2.2 mg/kg (dose was temporarily increased to 3.0 mg/kg on injection day 15 and 19) versus auristatin E dosed at 0.3 mg/kg, injected eight and seven times respectively twice weekly ($p<0.05$). Auristatin E achieved a status of stable disease up to day ~40 to then grow steadily until the end of the study. In contrast, AE-Ester-Sulf07 therapy caused complete remission from day 24 to day 53, reaching a minimum of 1 mm$^3$ tumor volume and a long-term effect.

AE-Ester-Sulf07 caused a transient body weight loss with a minimum of 9%, reached on day 31. Wounds due to biting and scratching were also observed starting from day 17. Two mice died, and one had to be sacrificed for general bad conditions (on day 20, 43 and 66).

Figure 20:
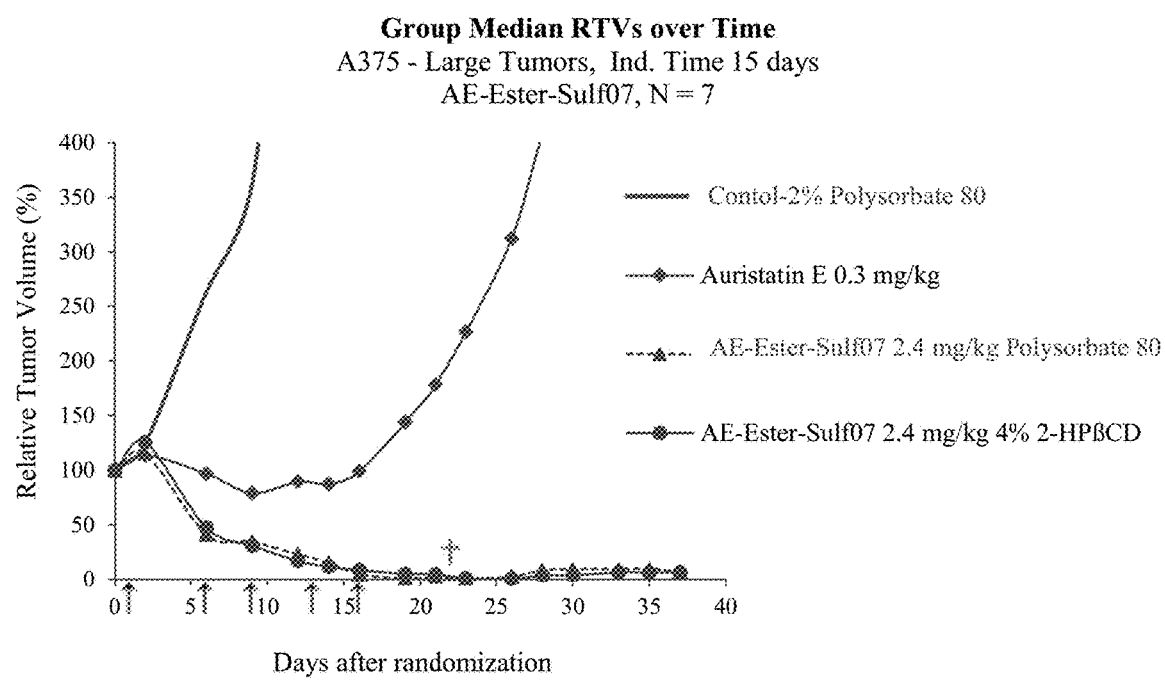
FIG. 20 shows the antitumor effect of auristatin E and AE-Ester-Sulf07, in comparison to control group in the malignant melanoma cancer model A375, average median starting tumor volume ~332 mm$^3$.

Evaluation of Auristatin E and the Albumin-Binding Auristatin E Derivative AE-Ester-Sulf07 in a Human Malignant Melanoma Cancer Model A375—Large Tumors (FIG. 20).

The evaluation of auristatin E and the albumin-binding auristatin E derivative AE-Ester-Sulf07 in a human malignant melanoma cancer model A375 was carried out as described in the general procedure for cell-line-derived xenograft models.

Based on the dosing experience in the RXF631 xenograft model, stock solutions were prepared as follows:

1) 7 mice, 28 g average weight, 310 mm$^3$ average median tumor volume on day of randomization: 0.3 mg/kg auristatin E TFA salt (AE equiv.) dosed twice weekly for 3 weeks on day 1, 6, 9, 13, 16=0.35 mg/kg=7.1 μg/20 g mouse. Sample preparation: 2 mg weighed in a 30 mL vial dissolved in 28.3 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On day of injection, the lyophilized samples were reconstituted with 1.2 mL of 10 mM sodium phosphate buffer, 20% propylene glycol—pH 7.0.
2) 7 mice, 29 g average weight, 371 mm$^3$ average median tumor volume on day of randomization: 2.4 mg/kg AE-Ester-Sulf07 (AE equiv.) dosed twice weekly for 3 weeks on day 1, 6, 9, 13, 16=4.37 mg/kg=87.3 μg/20 g mouse. Sample preparation: 12.6 mg weighed in a 30 mL vial dissolved in 14.4 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 50 mM sodium phosphate buffer, 2% polysorbate 80 (Tween® 80)—pH 7.6.
3) 7 mice, 31 g average weight, 355 mm$^3$ average median tumor volume on day of randomization: 2.4 mg/kg AE-Ester-Sulf07 (AE equiv.) dosed twice weekly for 3 weeks on day 1, 6, 9, 13, 16=4.37 mg/kg=87.3 μg/20 g mouse. Sample preparation: 12.6 mg weighed in a 30 mL vial dissolved in 14.4 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 50 mM sodium phosphate buffer, 4% 2-HPßCD—pH 7.6.

Tumor growth development in the melanoma xenograft model A375 shows statistically significant antitumor improvement of compound AE-Ester-Sulf07 dosed at 2.4 mg/kg (independently from the reconstitution buffer, 2% polysorbate 80 (Tween® 80) or 4% 2-HPßCD) compared to auristatin E dosed at 0.3 mg/kg, injected five times twice weekly ($p<0.01$ from day 9 to 33). Treatment with Auristatin E showed initial stable disease until day 14 after which the tumors grew steadily. Mice treated with AE-Ester-Sulf07 however, achieved almost complete remission from day 16 until the end of the study on day 37, reaching a minimum of 4 mm$^3$ on day 23 and 1 mm$^3$ on day 26 for the AE-Ester-Sulf07 reconstituted with 2% polysorbate 80 (Tween® 80) and 4% 2-HPßCD respectively, despite of the large median tumor volume at the beginning of the experiment.

No significant body weight change compared to the control was registered, but wounds due to biting and scratching were observed starting from day 9. Bepanthen treatment improved the health of wounded mice. Only one mouse in the AE-Ester-Sulf07 2% polysorbate 80 (Tween® 80) treated group had to be sacrificed for general bad conditions.

Figure 21:
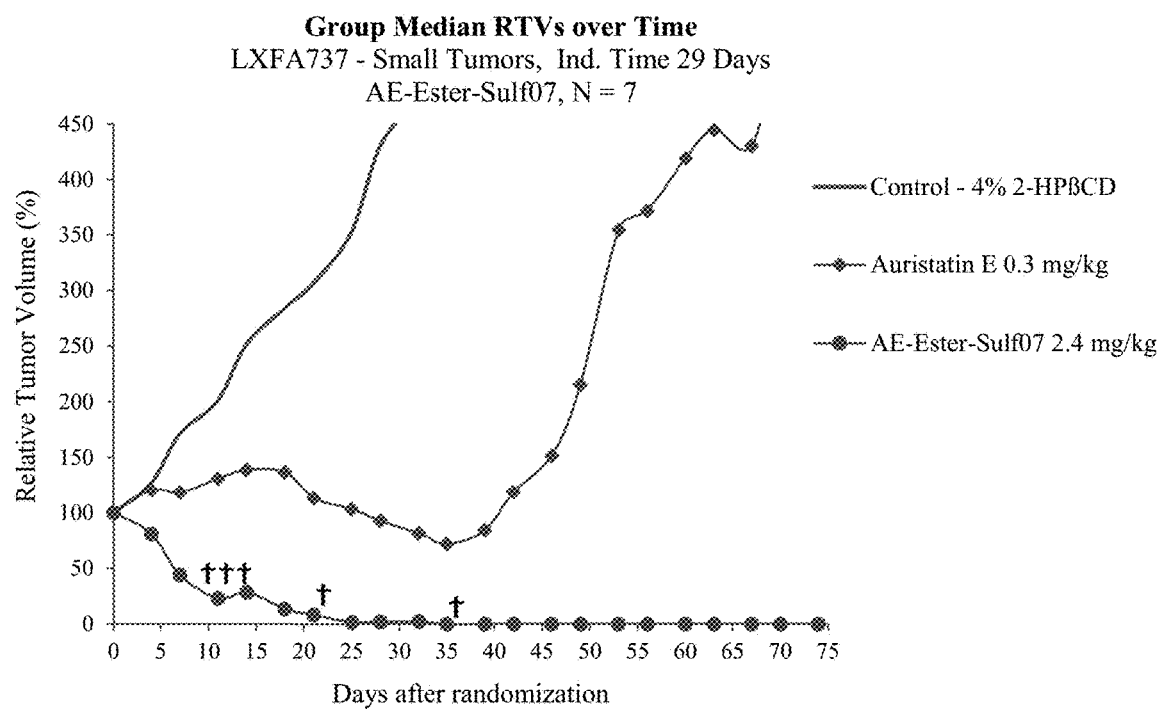
FIG. 21 shows the antitumor effect of auristatin E and AE-Ester-SulfW7, in comparison to control group in the NSCLC xenograft model LXFA737, average median starting tumor volume ~132 mm$^3$.

Evaluation of Auristatin E and the Albumin-Binding Auristatin E Derivative AE-Ester-Sulf07 in a Human Non-Small Cell Lung Cancer Model LXFA737—Small Tumors (FIG. 21).

The evaluation of auristatin E and the albumin-binding auristatin E derivative AE-Ester-Sulf07 in a human non-small cell lung cancer model LXFA737 was carried out as described in the general procedure for patient-derived xenograft models.

Stock solutions were prepared as follows:
1) 7 mice, 27 g average weight, 137 mm³ average median tumor volume on day of randomization: 0.3 mg/kg auristatin E TFA salt (AE equiv.) dosed twice weekly for 4 weeks on day 0, 4, 7, 11, 14, 18, 21, 25≡0.35 mg/kg≡7.1 µg/20 g mouse. Sample preparation: 2 mg weighed in a 30 mL vial dissolved in 28.3 mL 50/50 tert-butanol/10 mM sodium phosphate buffer, 5% sucrose—pH 7.0; 1.2 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 10 mM sodium phosphate buffer, 20% propylene glycol—pH 7.0.
2) 7 mice, 27 g average weight, 126 mm³ average median tumor volume on day of randomization: 2.4 mg/kg AE-Ester-Sulf07 (AE equiv.) dosed twice weekly for 4 weeks on day 0, 4, 7, 11, 14, 18, 21, 25=4.37 mg/kg≡87.3 µg/20 g mouse. Sample preparation: 31 mg weighed in a 30 mL vial dissolved in 28.5 mL 50/50 tert-butanol/10 mM sodium phosphate buffer, 5% sucrose—pH 7.0; 0.96 mL were aliquoted in 4 mL vials. The vials were frozen for 1 h at −40° C. and lyophilized at −20° C. over ~36 h and then stoppered. On the day of injection, the lyophilized samples were reconstituted with 1.2 mL of 50 mM sodium phosphate buffer, 4% 2-HPßCD—pH 7.6.

Tumor growth development in the NSCLC xenograft model LXFE737 showed superior antitumor efficacy of compound AE-Ester-Sulf07 at 2.4 mg/kg versus auristatin E at 0.3 mg/kg, both dosed 8 times twice weekly, with statistical significance (p<0.05 on day 56 and 63). Tumors in the auristatin E treated group stayed only temporarily in a status of stable disease from day 21 to day 42 and grew significantly after the end of the therapy. In contrast, mice treated with AE-Ester-Sulf07 reached complete tumor remission on day 21, bringing the tumor volume down to an unmeasurable level until the end of the study on day 74, resulting in a long term antitumor effect.

During the course of the study five mice had to be euthanized due to a combination of body weight loss and skin lesions.

Figure 22:
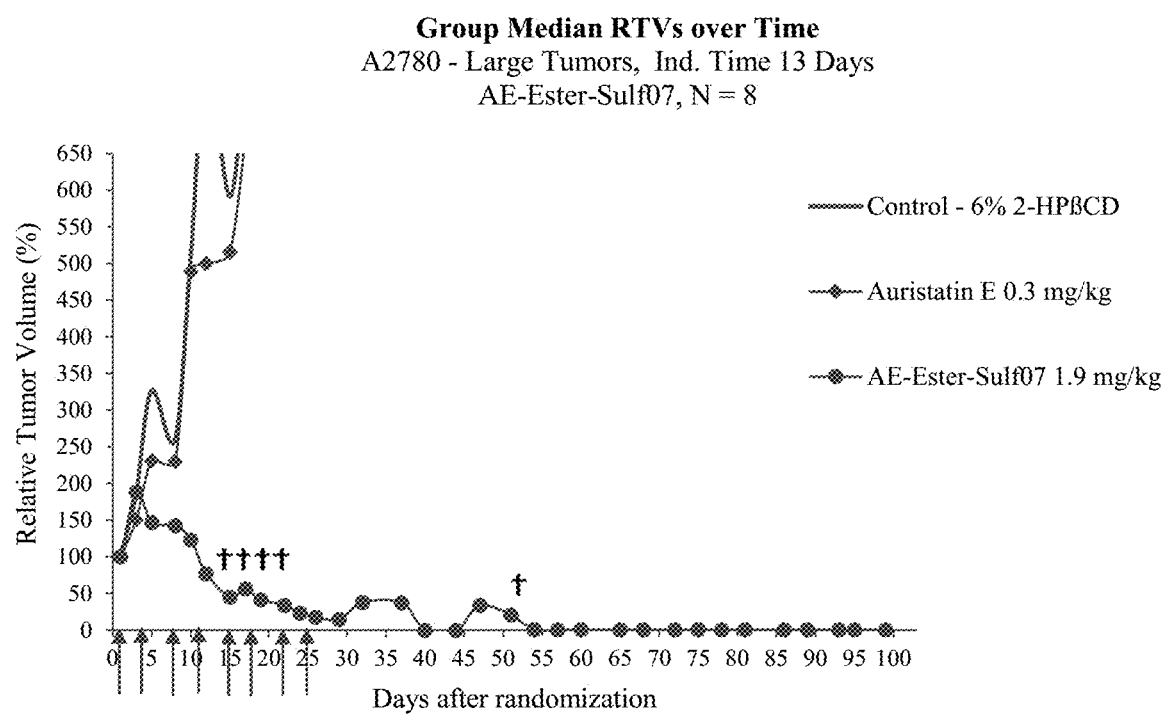
FIG. 22 shows the antitumor effect of auristatin E and AE-Ester-SulfW7, in comparison to control group in the human ovarian carcinoma model A2780, starting tumor volume ~351 mm$^3$.

Evaluation of Auristatin E and the Albumin-Binding Auristatin E Derivative AE-Ester-Sulf07 in a Human Ovarian Carcinoma Model A2780—Large Tumors (FIG. 22).

The evaluation of auristatin E and the albumin-binding auristatin E derivative AE-Ester-Sulf07 in a human ovarian carcinoma model A2780 was carried out as described in the general procedure for cell-line-derived xenograft models.

Stock solutions were prepared as follows:
1) 8 mice, 28 g average weight, 341 mm³ average median tumor volume on day of randomization: 0.3 mg/kg auristatin E TFA salt (AE equiv.) dosed twice weekly for 4 weeks on day 1, 4, 8, 11, 15, 18, 22, 25≡0.35 mg/kg≡7.1 µg/20 g mouse. Sample preparation: 3.7 mg weighed in a 100 mL vial dissolved in 52.3 mL 50/50 tert-butanol/10 mM sodium phosphate buffer, 5% sucrose—pH 7.0; 1.5 mL were aliquoted in 4 mL vials. The vials were frozen for 1 h at −40° C. and lyophilized at −20° C. over ~36 h and then stoppered. On day of injection, the lyophilized samples were reconstituted with 1.5 mL of 10 mM sodium phosphate buffer, 20% propylene glycol—pH 7.0.
2) 8 mice, 27 g average weight, 403 mm³ average median tumor volume on day of randomization: 1.9 mg/kg AE-Ester-Sulf07 (AE equiv.) dosed once weekly for 4 weeks on day 1, 4, 8, 11, 15, 18, 22, 25=3.46 mg/kg≡69.2 µg/20 g mouse. Sample preparation: 36.5 mg weighed in a 30 mL vial dissolved in 26.4 mL 50/50 tert-butanol/10 mM sodium phosphate buffer, 5% sucrose—pH 7.0; 0.75 mL were aliquoted in 4 mL vials. The vials were frozen for 1 h at −40° C. and lyophilized at −20° C. over ~36 h and then stoppered. On the day of injection, the lyophilized samples were reconstituted with 1.5 mL of 50 mM sodium phosphate buffer, 2% 2-HPßCD—pH 7.6.

AE-Ester-Sulf07 dosed at 1.9 mg/kg dose shows superior antitumor efficacy in the ovarian carcinoma model A2780 compared to auristatin E dosed at 0.3 mg/kg, both injected eight times twice weekly (p<0.001 from day 37 to day 40). Mice treated with auristatin E did not achieve any antitumor effect. Mice treated with AE-Ester-Sulf07 however, showed a partial remission from day 19 until day 51 and complete remission from day 54 until the end of the study on day 103, resulting in long term tumor regression.

AE-Ester-Sulf07 treated mice had no sign of body weight loss compared to the control, but four animals had to be removed from the study due to tumor necrosis.

Figure 23:
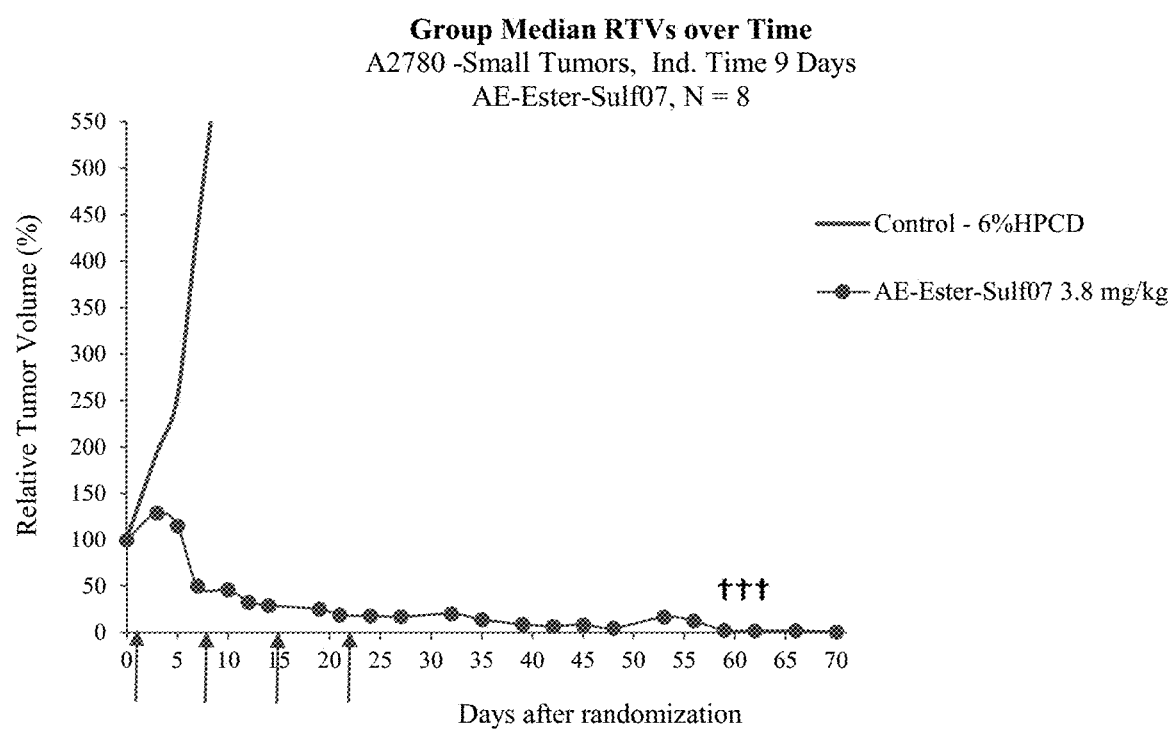
FIG. 23 shows the antitumor effect of AE-Ester-Sulf07, in comparison to control group in the human ovarian carcinoma model A2780, starting tumor volume ~148 mm$^3$.

Evaluation of the Albumin-Binding Auristatin E Derivative Compounds AE-Ester-Sulf07 in a Human Ovarian Carcinoma Model A2780—Small Tumors (FIG. 23).

The evaluation of the albumin-binding auristatin E derivative AE-Ester-Sulf07 in a human ovarian carcinoma model A2780 was carried out as described in the general procedure for cell-line-derived xenograft models.

Stock solutions were prepared as follows:
1) 8 mice, 27 g average weight, 174 mm³ average median tumor volume on day of randomization: 3.8 mg/kg AE-Ester-Sulf07 (AE equiv.) dosed once weekly for 4 weeks on day 1, 8, 15, 22=6.67 mg/kg≡133.4 µg/20 g mouse. Sample preparation: 25.6 mg weighed in a 30 mL vial dissolved in 19.2 mL 50/50 tert-butanol/10 mM sodium phosphate buffer, 5% sucrose—pH 7.0; 1.5 mL were aliquoted in 4 mL vials. The vials were frozen for 1 h at −40° C. and lyophilized at −20° C. over ~36 h and then stoppered. On the day of injection, the lyophilized samples were reconstituted with 1.5 mL of 50 mM sodium phosphate buffer, 6% 2-HPßCD—pH 7.6.

AE-Ester-Sulf07 was also tested in the same ovarian carcinoma model A2780 with smaller tumors and a different dosing scheme to diminish the side effects of the drug on the skin of the mice. AE-Ester-Sulf07 was dosed at 3.8 mg/kg four times once weekly, showing again a statistically significant improved antitumor effect compared to the control (p<0.01 from day 7 to 14). Mice treated with AE-Ester-Sulf07 in the new dosing regimen achieved partial remission from day 12 until day 35 and complete remission from day 39 until the end of the study on day 70. Three AE-Ester-Sulf07 treated mice showed body weight loss and had to be sacrificed on day 59.

The invention claimed is:
1. A compound having the structure of Formula I or II:

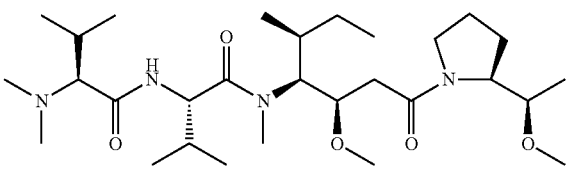

Formula I

-continued

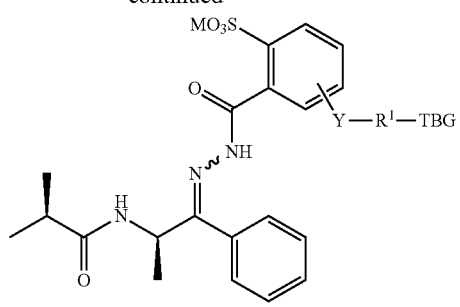

Formula II

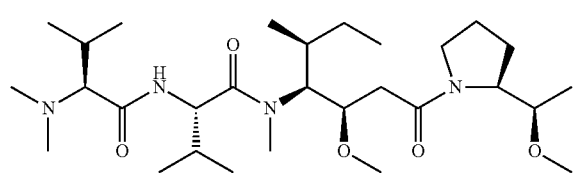

or a pharmaceutically acceptable salt, hydrate, solvate, or isomer thereof;

wherein:
R' is H or —CH$_3$,
M is H or a pharmaceutically acceptable counterion;
Y is absent or selected from an optionally substituted C$_1$-C$_6$ alkyl, —NH—C(O)—, —C(O)—NH—, —NH—C(O)—NH—, —C(O)—O—, and —O—C(O)—;
R$^1$ is absent or an optionally substituted C$_1$-C$_{18}$ alkyl wherein optionally up to six carbon atoms in said C$_1$-C$_{18}$ alkyl are each independently replaced with —OCH$_2$CH$_2$—;
X is H or selected from halogen, —NO$_2$, —NR$^2$R$^3$, —OR$^2$, —NHCOR$^2$ and —OCOR$^2$, wherein R$^2$ and R$^3$ are each independently selected from H and C$_1$-C$_4$ alkyl;
TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, and an optionally substituted acetylene group.

2. The compound according to claim 1, wherein R' is —CH$_3$.

3. The compound according to claim 1, wherein TBG is selected from an optionally substituted maleimide group.

4. The compound according to claim 1, wherein TBG is a maleimide group of the formula:

5. The compound according to claim 1, wherein Y is —NH—C(O)—.

6. The compound according to claim 1, wherein M is H$^+$ or Na$^+$.

7. The compound according to claim 1, wherein R$^1$ is an optionally substituted C$_1$-C$_5$ alkyl.

8. The compound according to claim 1, wherein R$^1$ is C$_1$-C$_5$ alkyl.

9. The compound according to claim 1, having the structure of Formula III:

Formula III

10. The compound according to claim 1, having the structure of Formula IV:

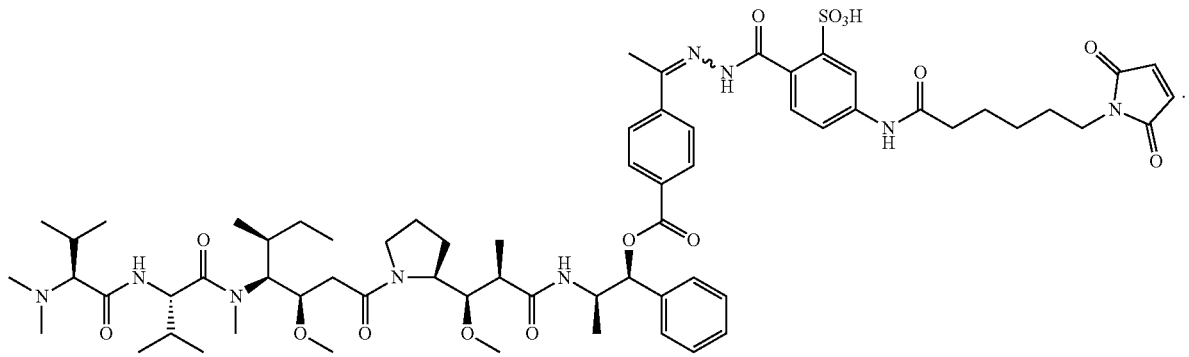

Formula IV

11. A pharmaceutical composition comprising the compound of claim 1, and a pharmaceutically acceptable carrier.

12. The pharmaceutical composition of claim 11, wherein the pharmaceutically acceptable carrier is selected from one or more of a solubilizing agent, an encapsulating agent and a lyoprotectant.

13. The pharmaceutical composition of claim 12, wherein the pharmaceutically acceptable carrier comprises one or more of dimethyl-3-cyclodextrin, hydroxyethyl-3-cyclodextrin, hydroxypropyl-3-cyclodextrin, and trimethyl-3-cyclodextrin.

14. The pharmaceutical composition of claim 11, wherein the pharmaceutical composition is suitable for intravenous administration.

15. The pharmaceutical composition of claim 14, wherein the composition, when administered intravenously to a patient, covalently binds in situ to endogenous albumin in blood circulation.

16. The pharmaceutical composition of claim 15, wherein the composition, when administered intravenously to a patient, covalently binds in situ to a thiol group of cysteine-34 of endogenous albumin in blood circulation.

17. A method for treating a patient suffering from a disease selected from a cancer, a virus disease, autoimmune disease, acute or chronic inflammatory disease, and a disease caused by bacteria, fungi, and other micro-organisms, comprising administering to the patient a therapeutically effective amount of the compound according to claim 1 or the pharmaceutical composition according to claim 11.

18. The method of claim 17, wherein the disease is cancer selected from carcinoma, sarcoma, leukemia, lymphoma, multiple myeloma, and melanoma.

19. The method of claim 17, wherein the administration is intravenous administration.

20. A method of reducing cytotoxicity of a compound comprising administering the compound according to claim 1 or the pharmaceutical composition according to claim 11 to a patient in need thereof, wherein the administration results in a reduction in cytotoxicity when compared to an equivalent dose of unmodified active agent.

21. A method of increasing the concentration of a metabolite of a compound in a tumor, comprising administering the compound according to claim 1 or the pharmaceutical composition according to claim 11 to a patient in need thereof, wherein the increase is compared to an equivalent dose of unmodified active agent.

22. The compound of claim 1, wherein the compound has a structure of Formula I

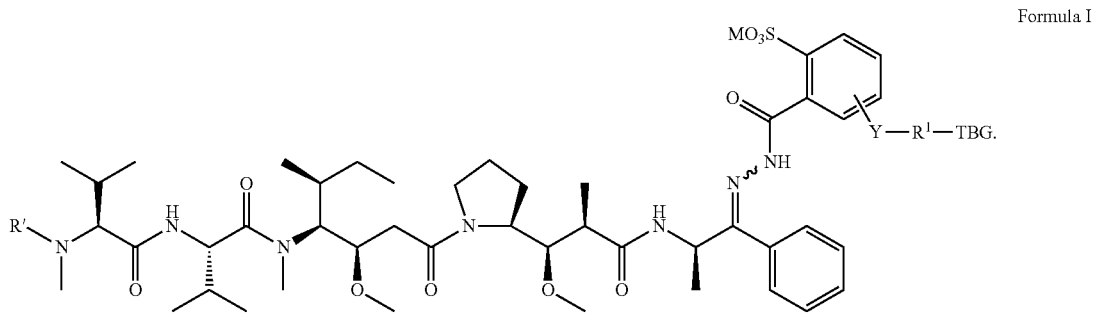

Formula I

23. The compound of claim 1, wherein the compound has a structure of Formula II

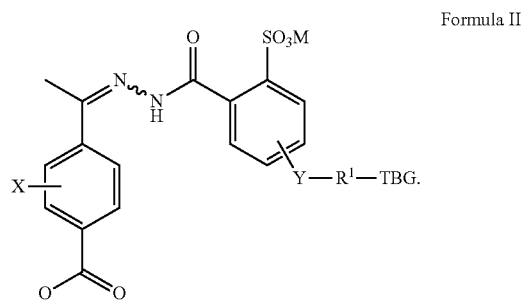

Formula II

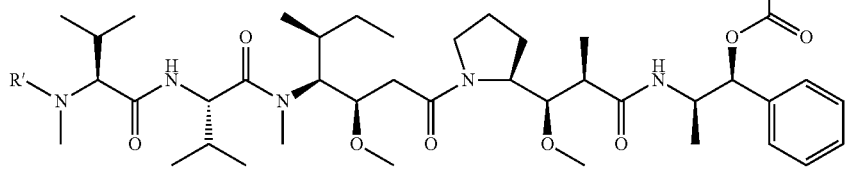

24. The compound of claim 1, wherein X is selected from the group consisting of F, Cl, Br and I.

25. The compound according to claim 22, wherein R' is —CH₃.

26. The compound according to claim 22, wherein TBG is selected from an optionally substituted maleimide group.

27. The compound according to claim 22, wherein TBG is a maleimide group of the formula:

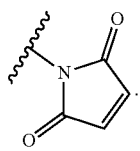

28. The compound according to claim 22, wherein Y is —NH—C(O)—.

29. The compound according to claim 22, wherein M is H⁺ or Na⁺.

30. The compound according to claim 22, wherein $R^1$ is an optionally substituted $C_1$-$C_5$ alkyl.

31. The compound according to claim 22, wherein $R^1$ is $C_1$-$C_5$ alkyl.

32. The compound according to claim 23, wherein R' is —CH₃.

33. The compound according to claim 23, wherein TBG is selected from an optionally substituted maleimide group.

34. The compound according to claim 23, wherein TBG is a maleimide group of the formula:

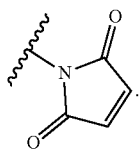 [SMILES: *N1C(=O)C=CC1=O]

35. The compound according to claim 23, wherein Y is —NH—C(O)—.

36. The compound according to claim 23, wherein M is H⁺ or Na⁺.

37. The compound according to claim 23, wherein $R^1$ is an optionally substituted $C_1$-$C_5$ alkyl.

38. The compound according to claim 23, wherein $R^1$ is $C_1$-$C_5$ alkyl.

39. The compound of claim 23, wherein X is selected from the group consisting of F, Cl, Br and I.

40. A pharmaceutical composition comprising the compound of claim 22, and a pharmaceutically acceptable carrier.

41. A pharmaceutical composition comprising the compound of claim 23, and a pharmaceutically acceptable carrier.

42. A method for treating a patient suffering from a disease selected from the group consisting of a cancer, a virus disease, autoimmune disease, acute or chronic inflammatory disease, and a disease caused by bacteria, fungi, and other micro-organisms, comprising administering to the patient a therapeutically effective amount of the compound according to claim 22 or the pharmaceutical composition according to claim 40.

43. The method of claim 42, wherein the disease is cancer selected from the group consisting of carcinoma, sarcoma, leukemia, lymphoma, multiple myeloma, and melanoma.

44. The method of claim 43, wherein the cancer is selected from the group consisting of adenocarcinoma, uveal melanoma, acute leukemia, acoustic neuroma, ampullary carcinoma, anal carcinoma, astrocytoma's, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinomas, uterine cancer, cervical cancer, neck, nose and ear tumors, hematological neoplasia's, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer and lymph gland cancer.

45. A method for treating a patient suffering from a disease selected from the group consisting of a cancer, a virus disease, autoimmune disease, acute or chronic inflammatory disease, and a disease caused by bacteria, fungi, and other micro-organisms, comprising administering to the patient a therapeutically effective amount of the compound according to claim 23 or the pharmaceutical composition according to claim 41.

46. The method of claim 45, wherein the disease is cancer selected from the group consisting of carcinoma, sarcoma, leukemia, lymphoma, multiple myeloma, and melanoma.

47. The method of claim 46, wherein the cancer is selected from the group consisting of adenocarcinoma, uveal melanoma, acute leukemia, acoustic neuroma, ampullary carcinoma, anal carcinoma, astrocytoma's, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinomas, uterine cancer, cervical cancer, neck, nose and ear tumors, hematological neoplasia's, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer and lymph gland cancer.

48. A pharmaceutical composition comprising the compound of claim 9, and a pharmaceutically acceptable carrier.

49. A pharmaceutical composition comprising the compound of claim 10, and a pharmaceutically acceptable carrier.

50. A method for treating a patient suffering from a disease selected from the group consisting of a cancer, a virus disease, autoimmune disease, acute or chronic inflammatory disease, and a disease caused by bacteria, fungi, and other micro-organisms, comprising administering to the patient a therapeutically effective amount of the compound according to claim 9 or the pharmaceutical composition according to claim 48.

51. The method of claim 50, wherein the disease is cancer selected from the group consisting of carcinoma, sarcoma, leukemia, lymphoma, multiple myeloma, and melanoma.

52. The method of claim 51, wherein the cancer is selected from the group consisting of adenocarcinoma, uveal melanoma, acute leukemia, acoustic neuroma, ampullary carcinoma, anal carcinoma, astrocytoma's, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinomas, uterine cancer, cervical cancer, neck, nose and ear tumors, hematological neoplasia's, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer and lymph gland cancer.

53. A method for treating a patient suffering from a disease selected from the group consisting of a cancer, a virus disease, autoimmune disease, acute or chronic inflammatory disease, and a disease caused by bacteria, fungi, and other micro-organisms, comprising administering to the patient a therapeutically effective amount of the compound according to claim 10 or the pharmaceutical composition according to claim 49.

54. The method of claim 53, wherein the disease is cancer selected from the group consisting of carcinoma, sarcoma, leukemia, lymphoma, multiple myeloma, and melanoma.

55. The method of claim 54, wherein the cancer is selected from the group consisting of adenocarcinoma, uveal melanoma, acute leukemia, acoustic neuroma, ampullary carcinoma, anal carcinoma, astrocytoma's, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinomas, uterine cancer, cervical cancer, neck, nose and ear tumors, hematological neoplasia's, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer and lymph gland cancer.

\* \* \* \* \*

UNITED STATES PATENT AND TRADEMARK OFFICE
CERTIFICATE OF CORRECTION

PATENT NO. : 11,377,473 B2
APPLICATION NO. : 16/768436
DATED : July 5, 2022
INVENTOR(S) : Felix Kratz et al.

Page 1 of 2

It is certified that error appears in the above-identified patent and that said Letters Patent is hereby corrected as shown below:

In the Claims

Column 72, Line 59 to Column 73, Line 45, Claim 1, replace:

"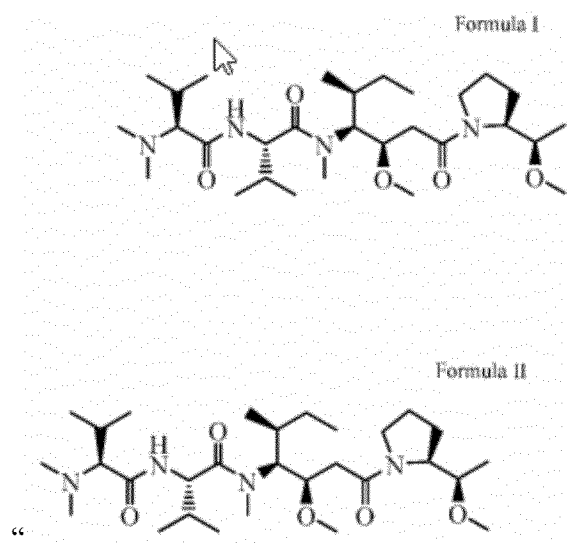 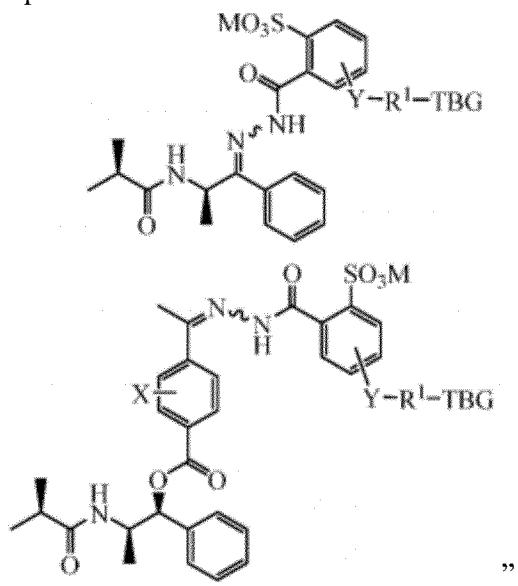"

Signed and Sealed this
Ninth Day of April, 2024

Katherine Kelly Vidal
*Director of the United States Patent and Trademark Office*

CERTIFICATE OF CORRECTION (continued)
U.S. Pat. No. 11,377,473 B2

With:

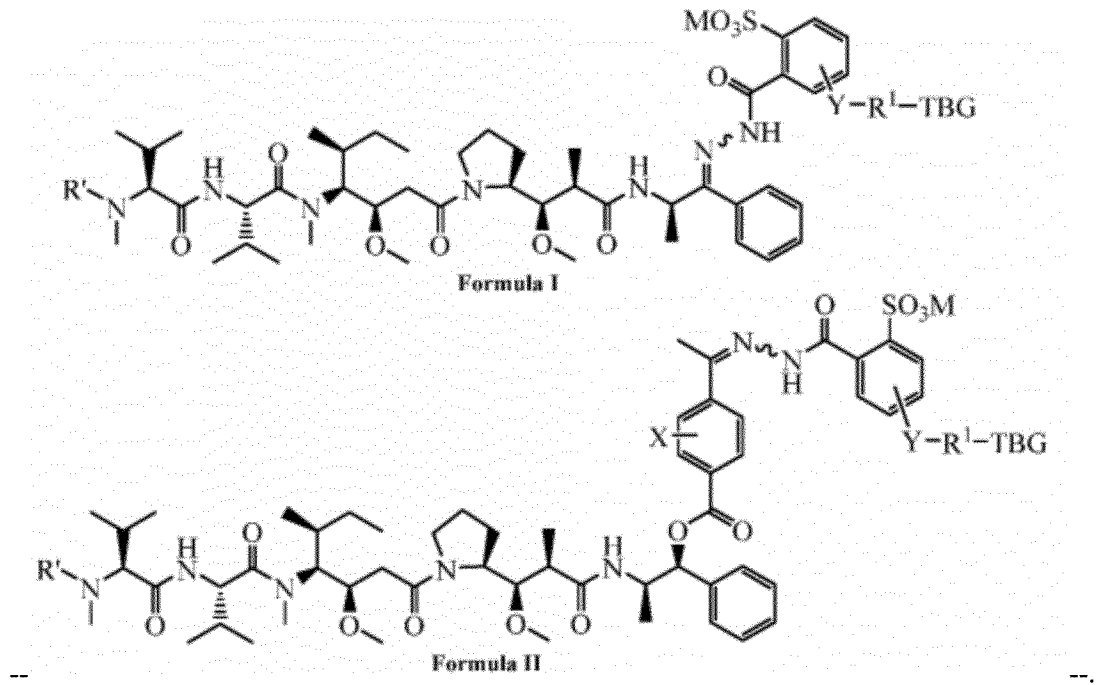

--                                                                                  --.